US009724352B2

(12) United States Patent
Yang et al.

(10) Patent No.: US 9,724,352 B2
(45) Date of Patent: *Aug. 8, 2017

(54) PYRROLO[2,1-F][1,2,4]TRIAZINE COMPOUNDS, PREPARATION METHODS AND APPLICATIONS THEREOF

(71) Applicants: Shanghai Institute of Materia Medica, Chinese Academy of Sciences, Shanghai (CN); Shanghai Haihe Pharmaceutical Co., Ltd., Shanghai (CN)

(72) Inventors: Chunhao Yang, Shanghai (CN); Linghua Meng, Shanghai (CN); Yanhong Chen, Shanghai (CN); Xiang Wang, Shanghai (CN); Cun Tan, Shanghai (CN); Jiapeng Li, Shanghai (CN); Jian Ding, Shaghai (CN); Yi Chen, Shanghai (CN)

(73) Assignees: Shanghai Institute of Materia Medica, Chinese Academy of Sciences, Shanghai (CN); Shanghai Haihe Pharmaceutical Co., Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/269,069

(22) Filed: Sep. 19, 2016

(65) Prior Publication Data
US 2017/0000800 A1 Jan. 5, 2017

Related U.S. Application Data

(63) Continuation-in-part of application No. 14/403,014, filed as application No. PCT/CN2013/074559 on Apr. 23, 2013, now Pat. No. 9,447,101.

(30) Foreign Application Priority Data

May 31, 2012 (CN) .......................... 2012 1 0177980

(51) Int. Cl.
| | |
|---|---|
| *A61K 31/53* | (2006.01) |
| *A61K 31/5377* | (2006.01) |
| *C07D 419/04* | (2006.01) |
| *A61P 35/00* | (2006.01) |
| *A61K 31/5386* | (2006.01) |
| *C07D 419/14* | (2006.01) |

(52) U.S. Cl.
CPC .......... *A61K 31/5377* (2013.01); *A61K 31/53* (2013.01); *A61K 31/5386* (2013.01); *C07D 419/04* (2013.01); *C07D 419/14* (2013.01)

(58) Field of Classification Search
CPC .... C07D 419/04; C07D 419/14; A61K 31/53; A61K 31/5377
USPC ............ 544/112, 183; 514/231.5, 232.8, 242
See application file for complete search history.

(56) References Cited

U.S. PATENT DOCUMENTS

| 9,447,101 B2* | 9/2016 | Yang ................ A61K 31/5377 |
|---|---|---|
| 2006/0084650 A1 | 4/2006 | Dong et al. |
| 2006/0089358 A1 | 4/2006 | Gavai et al. |
| 2008/0009497 A1 | 1/2008 | Wittman et al. |

FOREIGN PATENT DOCUMENTS

| CN | 102675323 A | 9/2012 |
|---|---|---|
| WO | WO 2004/009784 A2 | 1/2004 |
| WO | WO 2004/043912 A2 | 5/2004 |
| WO | WO 2004/054514 A2 | 7/2004 |
| WO | WO 2005/066176 A1 | 7/2005 |
| WO | WO 2006/069395 A2 | 6/2006 |
| WO | WO 2007/005709 A1 | 1/2007 |
| WO | WO 2007/061882 A2 | 5/2007 |
| WO | WO 2008/083398 A2 | 7/2008 |
| WO | WO 2008/131050 A1 | 10/2008 |
| WO | WO 2009/136966 A1 | 11/2009 |
| WO | WO 2010/002472 A1 | 1/2010 |
| WO | WO 2011/089400 A1 | 7/2011 |

OTHER PUBLICATIONS

[No Author Listed] Cecil Textbook of Medicine, edited by Bennet and Plum, 20$^{th}$ Edition, 1996; 1:1004-10.
Abraham et al, Novel series of pyrrolotriazine analogs as highly potent pan-Aurora kinase inhibitors. Bioorg Med Chem Lett. Sep. 15, 2011;21(18):5296-300. doi: 0.1016/j.bmcl.2011.07.027. Epub Jul. 14, 2011.
Banker et al., Modern Pharmaceuticals. Marcel Dekker. 3$^{rd}$ edition, 1996:451-596. Cai et al., Discovery of brivanib alaninate ((S)-((R)-1-(4-(4-fluoro-2-methyl-1H-indol-5-yloxy)-5-methylpyrrolo[2,1-f][1,2,4] triazin-6-yloxy)propan-2-yl)2-aminopropanoate), a novel prodrug of dual vascular endothelial growth factor receptor-2 and fibroblast growth factor receptor-1 kinase inhibitor (BMS-540215). J Med Chem. Mar. 27, 2008;51(6):1976-80. doi: 10.1021/jm7013309. Epub Feb. 21, 2008.
Cohen, The development and therapeutic potential of protein kinase inhibitors. Curr Opin Chem Biol. Aug. 1999;3(4):459-65. Review.
Dermer, Another Anniversary for the War on Cancer. Nature Biotechnology. 1994;12:320.

(Continued)

*Primary Examiner* — Venkataraman Balasubramanian
(74) *Attorney, Agent, or Firm* — Wolf, Greenfield & Sacks, P.C.

(57) ABSTRACT

The present invention relates to a pyrrolo[2,1-f][1,2,4]triazine compound, an isomer thereof or a pharmaceutically acceptable salt, ester or hydrate thereof, and a preparation method and application thereof. The pyrrolo[2,1-f][1,2,4] triazine compound has a structure expressed in general formula (I). The pyrrolo[2,1-f][1,2,4]triazine compound expressed in general formula (I) can inhibit a phosphatidylinositol-3 kinase (PI3K) signal pathway, thereby being used to prepare medicine for treating phosphatidylinositol-3 kinase related diseases such as cancer.

18 Claims, 4 Drawing Sheets

(56) References Cited

OTHER PUBLICATIONS

Engelman et al., Targeting PI3K signalling in cancer: opportunities, challenges and limitations. Nat Rev Cancer. Aug. 2009;9(8):550-62. doi: 10.1038/nrc2664. Review.
Engelman et al., The evolution of phosphatidylinositol 3-kinases as regulators of growth and metabolism. Nat Rev Genet. Aug. 2006;7(8):606-19. Review.
Fabbro et al., Protein kinases as targets for anticancer agents: from inhibitors to useful drugs. Pharmacol Ther. Feb.-Mar. 2002;93(2-3):79-98. Review.
Freshney et al., Culture of Animal Cells, A Manual of Basic Technique. Alan R. Liss, Inc. 1983; 4. 1 page.
Gaullier et al., FYVE finger proteins as effectors of phosphatidylinositol 3-phosphate. Chem Phys Lipids. Apr. 1999;98(1-2):87-94. Review.
Gautschi et al., Aurora kinases as anticancer drug targets. Clin Cancer Res. Mar. 15, 2008;14(6):1639-48. doi: 10.1158/1078-0432. CCR-07-2179. Review.
Gavai et al., Discovery and preclinical evaluation of [4-[[1-(3-fluorophenyl)methyl]-1H-indazol-5-ylamino]-5-methylpyrrolo[2,1-f][1,2,4]triazin-6-yl]carbamic acid, (3S)-3-morpholinylmethyl ester (BMS-599626), a selective and orally efficacious inhibitor of human epidermal growth factor receptor 1 and 2 kinases. J Med Chem. Nov. 12, 2009;52(21):6527-30. doi:10. 1021/jm9010065.
Golub et al., Molecular classification of cancer: class discovery and class prediction by gene expression monitoring. Science. Oct. 15, 1999;286(5439):531-7.
Hayashi et al., C-Nucleosides.17.[1] A Synthesis of 2-Substituted 7(β-D-Ribofuranosyl)- Pyrrolo (2,1-f-1,2,1,2,4-Triazines. A new type of "Purine Like" C-Nucleoside. Heterocycles. 1992; 34(3):569-74.
Hunt et al, Discovery of the pyrrolo[2,1-f][1,2,4]triazine nucleus as a new kinase inhibitor template. J Med Chem. Jul. 29, 2004;47(16):4054-9.
Kamijo et al., Copper- or phosphine-catalyzed reaction of alkynes with isocyanides. Regioselective synthesis of substituted pyrroles controlled by the catalyst. J Am Chem Soc. Jun. 29, 2005;127(25):9260-6.
Klempner et al., What a tangled web we weave: emerging resistance mechanisms to inhibition of the phosphoinositide 3-kinase pathway. Cancer Discov. Dec. 2013;3(12):1345-54. doi: 10.1158/2159-8290. CD-13/0063. Review.
Liu et al., Discovery of 4-(5-(cyclopropylcarbamoyl)-2-methylphenylamino)-5-methyl-N-propylpyrrolo[1,2-f][1,2,4]triazine-6-carboxamide (BMS-582949), a clinical p38α MAP kinase inhibitor for the treatment of inflammatory diseases. J Med Chem. Sep. 23, 2010;53(18):6629-39. doi: 10.1021/jm100540x.
Mass, The HER receptor family: a rich target for therapeutic development. Int J Radiat Oncol Biol Phys. Mar. 1, 2004;58(3):932-40. Review.
Massacesi et al., Challenges in the clinical development of PI3K inhibitors. Ann N Y Acad Sci. Mar. 2013;1280:19-23. doi:10.1111/nyas.12060. Review.
Mesaros et al., Strategies to mitigate the bioactivation of 2-anilino-7-aryl-pyrrolo[2,1-f][1,2,4]triazines: identification of orally bioavailable, efficacious ALK inhibitors. J Med Chem. Jan. 12, 2012;55(1):115-25. doi: 10.1021/jm2010767. Epub Dec. 29, 2011.
Mountzios et al., Aurora kinases as targets for cancer therapy. Cancer Treat Rev. Apr. 2008;34(2):175-82. Review.
Patil et al., 4-Aza-7,9-Dideazaadenosine, a New Cytotoxic Synthesis C-Nucleoside Analogue of Adenosine.Tetrahedron Ltrs.Jul. 25, 1994;v35:p5339-42. doi:10.1016/S0040-4039(00)73494-0.
Schroeder et al., Identification of pyrrolo[2,1-f][1,2,4]triazine-based inhibitors of Met kinase. Bioorg Med Chem Lett. Mar. 15, 2008;18(6):1945-51. doi: 10.1016/j.bmcl.2008.01.121. Epub Feb. 7, 2008.
Thieu et al., Discovery and process synthesis of novel 2,7-pyrrolo[2,1-f][1,2,4]triazines. Org Lett. Aug. 19, 2011;13(16):4204-7. doi: 10.1021/ol12015237. Epub Jul. 26, 2011.
Vanhaesebroeck et al., Synthesis and function of 3-phosphorylated inositol lipids. Annu Rev Biochem. 2001;70:535-602. Review.
Wang et al., Discovery and bioactivity of 4-(2-arylpyrido[3',2':3,4]pyrrolo[1,2-f][1,2,4]triazin-4-yl) morpholine derivatives as novel PI3K inhibitors. Bioorg Med Chem Lett. Jan. 1, 2012;22(1):339-42. doi: 10.1016/j.bmcl.2011.11.003. Epub Nov. 9, 2011.
Weinberg et al., 2,7-Pyrrolo[2,1-f][1,2,4]triazines as JAK2 inhibitors: modification of target structure to minimize reactive metabolite formation. Bioorg Med Chem Lett. Dec. 15, 2011;21(24):7325-30. doi: 10.1016/jbmcl.2011.10.032. Epub Oct. 14, 2011.
Wittman et al., Discovery of a 2,4-disubstituted pyrrolo[1,2-f][1,2,4]triazine inhibitor (BMS-754807) of insulin-like growth factor receptor (IGF-1R) kinase in clinical development. J Med Chem. Dec. 10, 2009;52(23):7360-3. doi: 10.1021/jm900786r.
Wolff, Burger's Medicinal Chemistry, Part 1. John Wiley & Sons. 5th edition, 1995;975-7.

\* cited by examiner

US 9,724,352 B2

PYRROLO[2,1-F][1,2,4]TRIAZINE COMPOUNDS, PREPARATION METHODS AND APPLICATIONS THEREOF

CROSS-REFERENCE TO RELATED APPLICATIONS

This application is a continuation-in-part application of U.S. patent application Ser. No. 14/403,014, filed Nov. 21, 2014, which is a national stage filing under 35 U.S.C. §371 of International Application No. PCT/CN2013/074559," filed Apr. 23, 2013, which claims priority to Chinese Patent Application No. CN201210177980.3, filed May 31, 2012. The entire content of each of the prior applications is herein incorporated by reference in its entirety.

TECHNICAL FIELD

The invention relates to pyrrolo[2,1-f][1,2,4]triazine derivatives as shown in general formula I, isomers thereof or pharmaceutically acceptable salts, esters or hydrates thereof, and preparation method and use thereof. Compounds I as shown in general formula I can inhibit phosphatidylinositol 3-kinase (PI3K) signal pathway, thereby being used to prepare medicaments for treating phosphatidylinositol 3-kinase related diseases, such as cancer.

BACKGROUND

PI3K is a lipid kinase and can phosphorylate 3-position of inositol ring in phosphatidylinositol to form phosphatidylinositol-3-phosphate (PIP), phosphatidylinositol-3,4-diphosphate (PIP2) and phosphatidylinositol-3,4,5-triphosphate (PIP3). PIP, PIP2 and PIP3, as important second messengers, bind and activate various proteins containing PH domain (pleckstrin homology domain), FYVE domain (named after the first letter of Fablp, YOTB, Vaclp and EEA1 proteins containing FYVE domain found originally, see Gaullier, J. M.; Simonsen, A.; D'Arrigo, A.; Bremnes, B.; Stenmark, H., *Chem. Phys. Lipids,* 1999, 98: 87-94.), PX domain (Phox homology domain) and other phospholipid-binding region, to form a signaling cascade complex, and ultimately regulate cell activities such as proliferation, differentiation, survival and migration etc. (see Vanhaesebroeck, B.; Leevers, S. J.; Ahmadi, K.; Timms, J.; Katso, R.; Driscoll, P. C.; Woscholski, R.; Parker, P. J.; Waterfield, M. D., *Annu. Rev. Biochem.,* 2001, 70: 535-602).

Depending on the differences in gene sequence, the substrate specificity and function, PI3K superfamily is grouped into three classes: I, II and III PI3K. Class I PI3Ks are most widely studied class by far. The substrates of PI3Ks are phosphatidylinositol (PI), phosphatidylinositol-4-phosphate (PI(4)P), phosphatidylinositol 4,5-bisphosphate (PI(4,5)P2). Class I PI3Ks are heterodimeric molecules composed of one catalytic subunit and one regulatory subunit. Class I PI3Ks can be further divided into two categories due to the difference in the regulatory subunit and activation mechanism: PI3K IA and PI3K IB. Wherein, PI3K IA comprises PI3Kα, PI3Kβ and PI3Kδ, and is actived by receptor tyrosine kinase; while PI3K IB only consists of PI3Kγ and is actived by G protein-coupled receptors. PI and PI(4)P are substrates of class II PI3Ks. Class II PI3Ks include PI3KC2α, PI3KC2β and PI3KC2γ. They are characterized by a C2 domain at the C terminus, indicating that their activities are regulated by calcium ion. The substrate of class III PI3K is PI. Its activation mechanism remains unclear up to now (see, Engelman, J. A.; Luo, J.; Cantley, L. C., *Nat. Rev. Genet.,* 2006, 7: 606-619).

Hyper-activation of PI3K initiates phosphatidylinositol 3-kinase/protein kinase B/mammalian target protein of rapamycin (PI3K/Akt/mTOR) signal pathway and promotes cell survival and proliferation, which is frequently present in about 60% of human tumors. PTEN (phosphatase and tensin homolog deleted on chromosome 10) acts as a tumor suppressor and dephosphorylate 3-position at inositol ring of phosphatidylinositol and antagonize the activity of PI3K. Such function is lost in many cancers. Active mutation in gene PIK3CA encoding p110α is present in over 30% of cancers. Moreover, gene amplifications of PI3K3CA and protein kinase B (Akt) have been frequently found in other cancers which also contribute to the expression of protein (see Engelman, J. A., *Nat. Rev. Cancer,* 2009, 9: 550-562). These facts indicate that PI3K is closely related to the tumorigenesis and promotion. The target protein of rapamycin (mTOR) is one of important downstream protein of protein kinase B, which is a serine/threonine kinase. Protein kinase B further activates the target protein of rapamycin by directly phosphorylating mTOR; or indirectly enhancing the activation of mTOR by inactivating tumor suppressor gene TSC2 (Tuberous sclerosis protein 2). The active mTOR directly or indirectly takes part in regulations of various processes relating to cell proliferation and growth, such as the initial stage of translation, transcription, microfilament restruction, membrane transport, protein degradation, protein kinase C (PKC) pathway, ribosomal protein synthesis and tRNA synthesis etc by regulating downstream signaling pathways, such as ribosome S6 kinase (S6K1, or P70S6K), eukaryotic cells translation initiation factor 4E (eIF-4 e) binding protein 1 (4E-BP1), signal transduction and transcription activation factor 3 (STAT3), etc. Therefore, mTOR is a center regulatory protein of cell growth and proliferation and has become a new antitumor drug target.

PI3K and downstream signaling protein mTOR inhibitors are a class of promising antitumor drugs. At present, several pan-PI3K inhibitors, such as GDC-0941, XL-147, PX-866, etc. have entered into clinical studies. However, the number and structure diversity need to be expanded to meet the needs of research and development of new anticancer drug. Meanwhile, there are defects existing in known inhibitors. For example, PX-866, which is derived from Wortmannin, is difficult to be synthesized; and the activity of GDC-0941 needs to be improved. Therefore, discovery and development of antitumor drugs targeting PI3K with higher activity, better safety attract increasing interest world wide.

Pyrrolo[2,1-f][1,2,4]triazine is a privileged structure in medicinal chemistry. After this privileged structure was reported as purine analogues (see: Hayashi, M.; Araki, A.; Maeba, J., *Heterocycles,* 1992, 34: 569-574. Patil, S. A.; Otter, B. A.; Klein, R. S., *Tetrahedron Lett.,* 1994, 35: 5339-5342), more and more compounds containing such privileged structure were synthesized and displayed a variety of biological activities, for example, acting as JAK2 inhibitors (see: Weinberg, L. R.; Albom, M. S.; Angeles, T. S. et al., *Bioorg. Med. Chem. Lett.* 2001, 21: 7325-7330), pan-Aurora kinase inhibitors (Abraham, S.; Hadd, M. J.; Tran, L. et al., *Bioorg. Med. Chem. Lett.* 2011, 21: 5296-5300), p38α mitogen-activated protein kinase (p38a MAPK) inhibitors (Liu, C.; Lin, J.; Wrobleski, S. T. et al., *J. Med. Chem.,* 2010, 53: 6629-6639), lymphoma kinase ALK inhibitors (Mesaros, E. F.; Thieu, T. V.; Wells, G. J. et al., *J. Med. Chem.,* 2012, 55: 115-125), VEGFR-2/FGFR-1 dual inhibitors (Cai, Z.-w.; Zhang, Y.; Borzilleri, R. M. et al., *J. Med. Chem.,* 2008, 5: 1976-1980), VEGFR-2 inhibitors (Hunt, J. T.; Mitt, T.; Borzilleri, R. et al., *J. Med. Chem.,* 2004, 47: 4054-4059), EGFR1/2 inhibitors (Gavai, A. V.; Fink, B. E.; Fairfax, D. J. et al., *J. Med. Chem.,* 2009, 52: 6527-6530), IGF-1R inhibitors (see: Wittman, M. D.; Carboni, J. M.; Yang, Z. et al. *J. Med. Chem.,* 2009, 52: 7360-7363), or Met kinase inhibitors (see: Schroeder, G. M.; Chen, X.-T.; Williams, D. K. et al., *Bioorg. Med. Chem.*

Lett., 2007, 18: 1945-1951). Moreover, compounds containing this pyrrolo[2,1-f][1,2,4]triazine privileged structure such as EGFR inhibitor AC-480 (WO-2004054514), VEGF-2 receptor antagonist BMS-690514 (WO2005/066176A1), and IGF-1R antagonist BMS-754807 (US2008/0009497 A1) etc. have entered into the clinical studies. The synthetic methods for the core structure of pyrrolo[2,1-f][1,2,4]triazine have also been reported, for example, Thieu, T; Sclafani, J. A.; Levy, D. V. et al., Org. Lett., 2011, 13: 4204-4207. In addition to above mentioned literatures, there are many patent applications related to the core structure of pyrrolo[2,1-f][1,2,4]triazine, for example, acting as kinase inhibitors (publication No.: US2006/0084650A1), EGFR kinase inhibitors (Publication No.: US2006/0089358A1, WO2006/069395), VEGFR-2 and FGFR-1 inhibitors (Publication No.: WO2004/009784, WO2004/043912), and patent applications related to the synthetic methods for intermediates (WO2007/005709, WO2008/083398), tyrosine receptor kinase inhibitors (WO2007/061882, WO2008/131050), Aurora kinase inhibitors (Publication Number: WO2009/136966), JAK kinase inhibitors (Publication No.: WO2010/002472). The reported pyrrolo[2,1-f][1,2,4]triazines mentioned above do not cover and relate to the compounds of the present invention and use thereof as PI3K inhibitors.

Based on the aforementioned reasons, the inventors designed and synthesized a series of PI3K inhibitors with pyrrole[2,1-f][1,2,4]triazine as core structure. The compounds in the present invention have demonstrated excellent bioactivity both in vitro and in vivo, and are expected to be developed into a novel anti-cancer medicament.

SUMMARY OF THE INVENTION

The object of the present invention is to provide a novel type of pyrrolo[2,1-f][1,2,4]triazine derivatives as shown in general formula I.

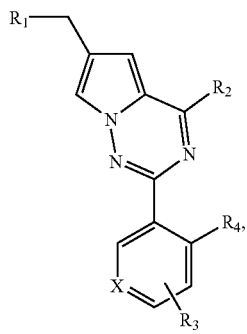

I wherein,
X=CH or N;
$R_1$ is —$NR_5R_6$;
$R_2$ is

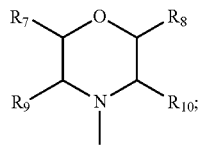

$R_3$ is —$NH_2$, —$NHC(O)NHR_{11}$, —$NHC(O)OR_{11}$, —$CH_2OH$, —$CH_2S(O)_2R_{12}$, —$CH_2OS(O)_2R_{12}$ or —$CH_2NHS(O)_2R_{12}$;
$R_4$ is H or $CF_3$;
$R_5$ and $R_6$ are each independently a C1-C4 alkyl, or combined with the nitrogen atom to which they are attached to form an unsubstituted saturated heterocycle or a saturated heterocycle substituted by substituent(s), preferably a pyrrolidyl, a piperidinyl and a piperazinyl, most preferably a piperazinyl; the substituent is —$S(O)_2R_{12}$;
$R_7$, $R_8$, $R_9$ and $R_{10}$ are each independently H or C1-C3 alkyl; alternatively, $R_7$ and $R_8$, or $R_9$ and $R_{10}$ are combined with the carbon atom to which they are attached to form a 5-8 membered saturated ring; preferably, $R_7$ and $R_8$, or $R_9$ and $R_{10}$, with the carbon atoms to which they are attached as bridge carbon atoms, form bridged bicylco-heterocycle with morpholine ring;
$R_{11}$ is a C1-C4 alkyl, an unsubstituted C3-C6 cycloalkyl or a C3-C6 cycloalkyl substituted by one or more substituents, an unsubstituted benzyl or a benzyl substituted by one or more substituents, an unsubstituted phenyl or a phenyl substituted by one or more substituents, an unsubstituted isoxazolyl or an isoxazolyl substituted by one or more substituents, or an unsubstituted pyridyl or a pyridyl substituted by one or more substituents, the one or more substituents are selected from a halogen, a C1-C3 alkyl, or a C1-C3 alkoxyl, —$CF_3$, —$C(O)O_{12}$, —$C(O)NR_{12}R_{15}$,

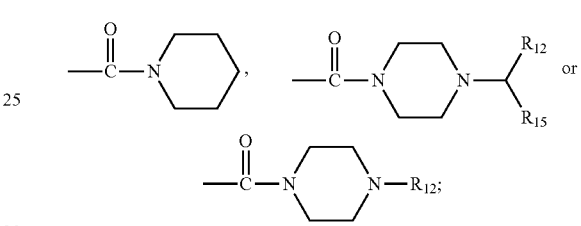

$R_{12}$ and $R_{15}$ are each independently C1-C3 alkyl.
Preferably, the structure of general formula I is shown as follows:

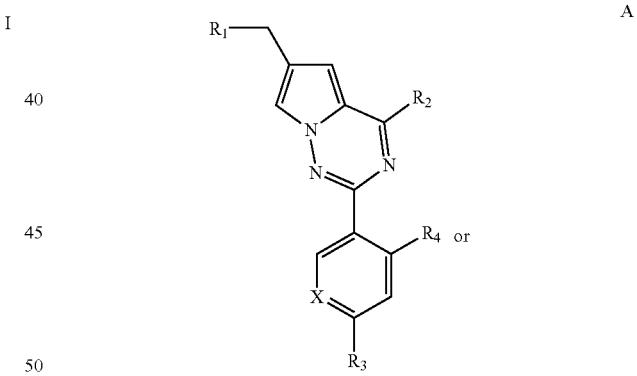

A

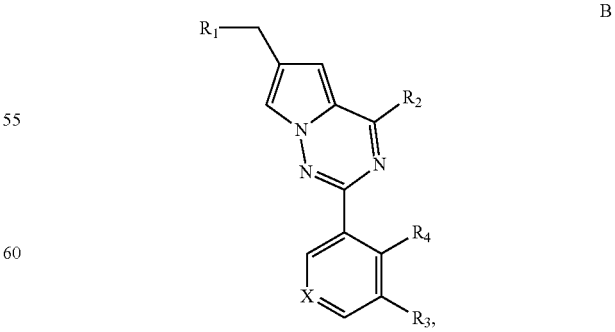

B wherein X, $R_1$, $R_2$, $R_3$ and $R_4$ are defined as above.
More preferably, $R_1$ is dimethylamino or 1-methylsulfonyl piperazinyl;

R$_2$ is morpholinyl, (S)-3-methylmorpholinyl, or 8-oxa-3-azabicyclo[3.2.1]octan-3-yl;

R$_3$ is —NH$_2$, —NHC(O)NHR$_{11}$, —NHC(O)OR$_{11}$, —CH$_2$OH, —CH$_2$S(O)$_2$Me, or —CH$_2$NHS(O)$_2$Me;

R$_4$ is H or —CF$_3$;

R$_{11}$ is a methyl, an ethyl, a propyl, a cyclopropyl, a tert-butyl, an iso-butyl, a 4-fluorobenzyl, an unsubstituted phenyl or a phenyl substituted by one or more substituents, an unsubstituted isoxazolyl or an isoxazolyl substituted by one or more substituents, or an unsubstituted pyridine ring or a pyridine ring substituted by one or more substituents, and the substituent is selected from a fluorine, a chlorine, a trifluoromethyl, a methyl, a methoxy, an ethoxycarbonyl, a dimethylaminocarbonyl, a 4-methyl-piperazine-1-carbonyl, a piperidine-1-carbonyl and a 4-dimethylaminopiperidine-1-carbonyl.

More preferably, the compounds represented by general formula I have the following structures:

Ia

Ib

Ic

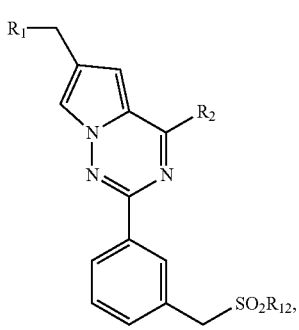
Id

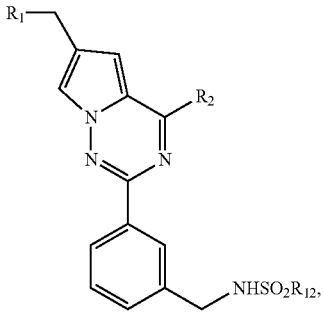
Ie

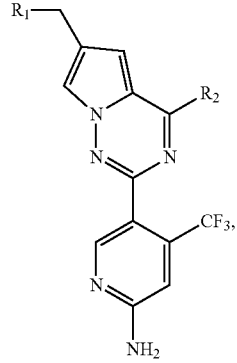
If

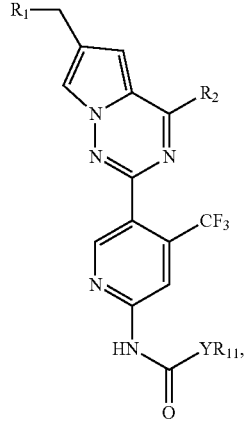
Ig

Y = NH or O wherein R$_1$, R$_2$, R$_{11}$ and R$_{12}$ are defined as above,

R$_{16}$ and R$_{17}$ are identical or different, and each independently selected from C1-C4 alkyl, or R$_{16}$ and R$_{17}$ are combined with the nitrogen atom to which they are attached to form a 4-methyl-piperazinyl, a 4-dimethylamino-piperidyl or piperidin-1-yl.

Most preferably, the present invention provides the compounds as shown in table 1.

TABLE 1
The structures of representative compounds of general formula I
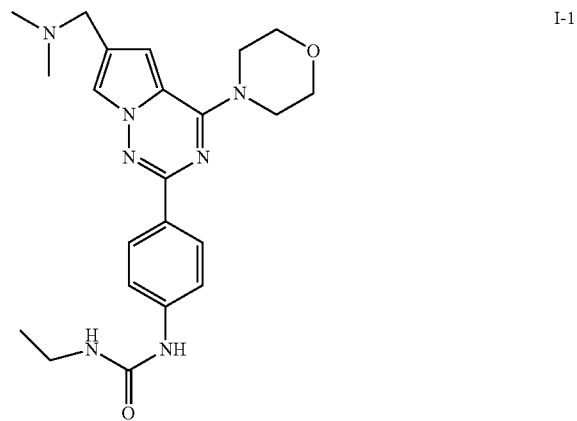
I-1
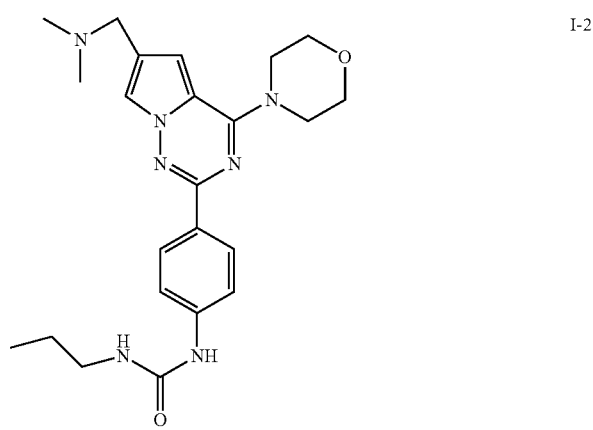
I-2
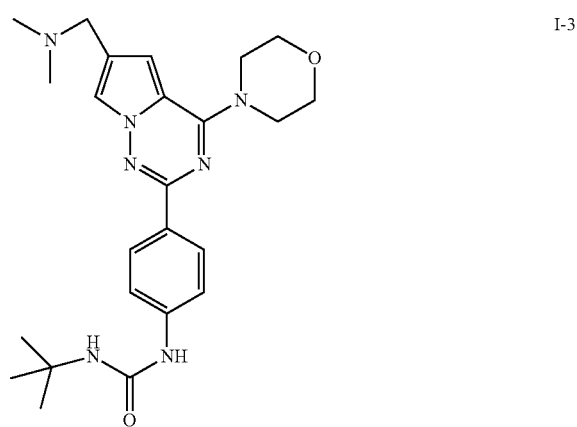
I-3

TABLE 1-continued
The structures of representative compounds of general formula I
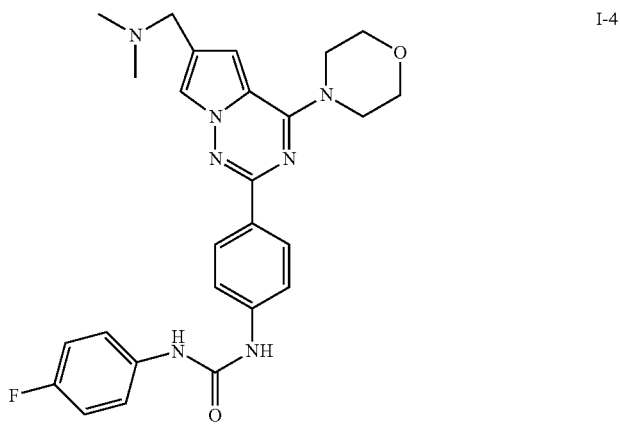
I-4
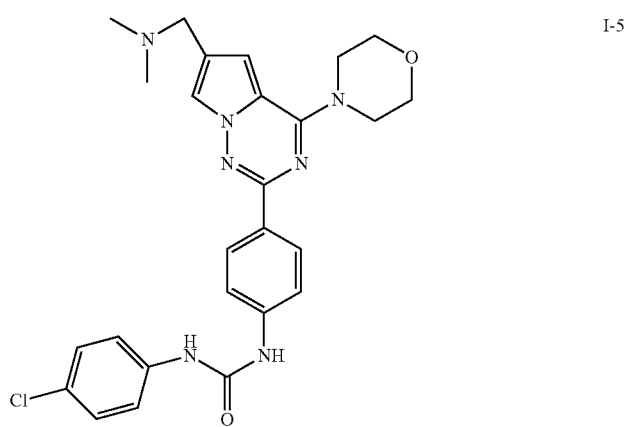
I-5
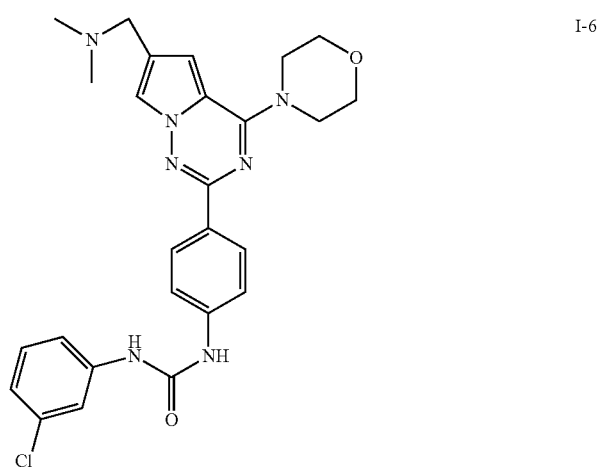
I-6

TABLE 1-continued
The structures of representative compounds of general formula I
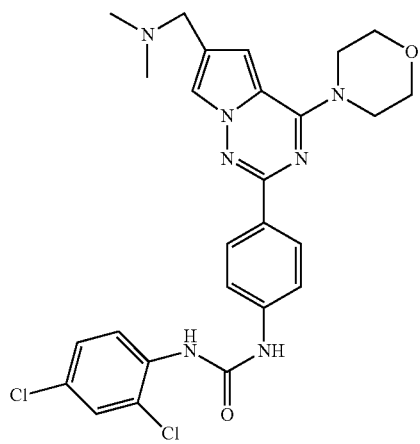
I-7
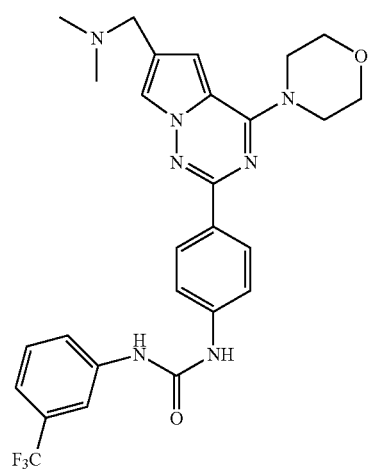 [SMILES: CN(C)Cc1cc2c(N3CCOCC3)nc(-c3ccc(NC(=O)Nc4cccc(C(F)(F)F)c4)cc3)nn2c1]
I-8
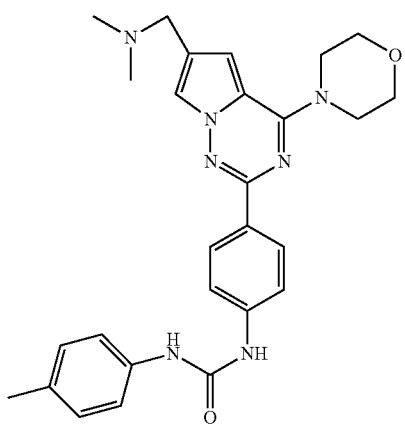 [SMILES: Cc1ccc(NC(=O)Nc2ccc(-c3nc(N4CCOCC4)c4cc(CN(C)C)cn4n3)cc2)cc1]
I-9

TABLE 1-continued
The structures of representative compounds of general formula I
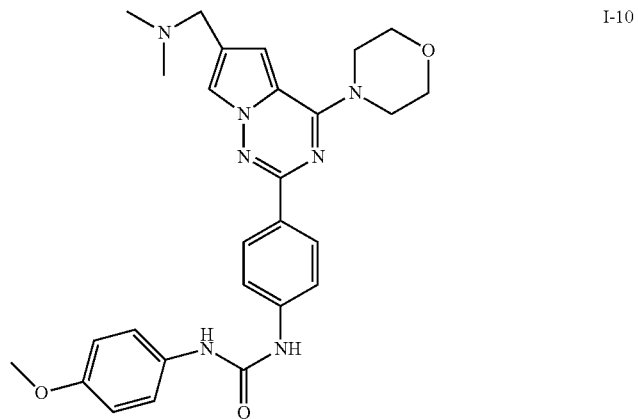
I-10
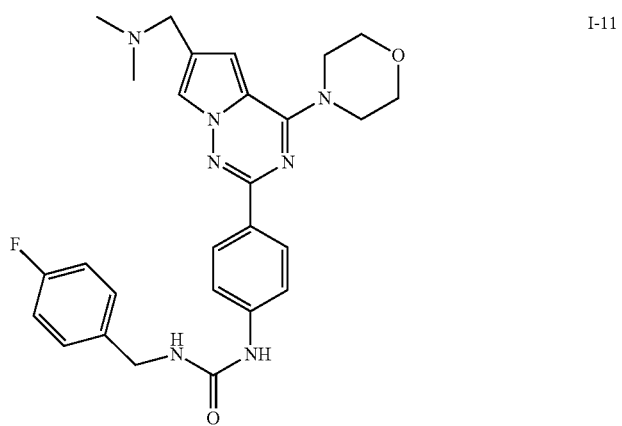
I-11
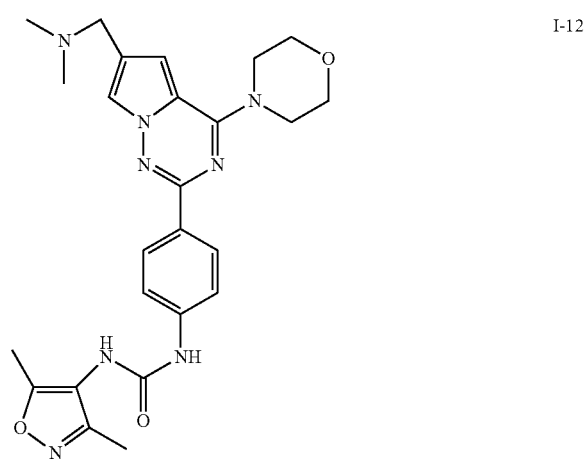
I-12

15 16
TABLE 1-continued
The structures of representative compounds of general formula I
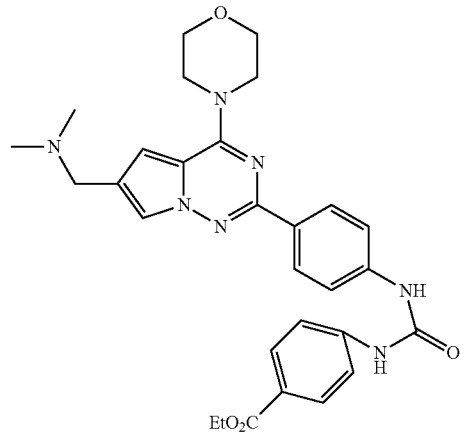
I-13
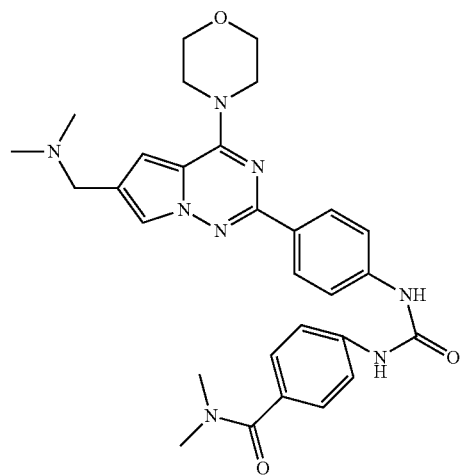 [SMILES: CN(C)Cc1cc2c(N3CCOCC3)nc(-c3ccc(NC(=O)Nc4ccc(C(=O)N(C)C)cc4)cc3)nn2c1]
I-14
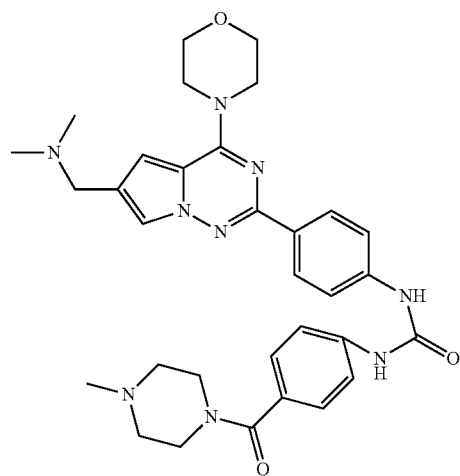 [SMILES: CN(C)Cc1cc2c(N3CCOCC3)nc(-c3ccc(NC(=O)Nc4ccc(C(=O)N5CCN(C)CC5)cc4)cc3)nn2c1]
I-15

TABLE 1-continued
The structures of representative compounds of general formula I
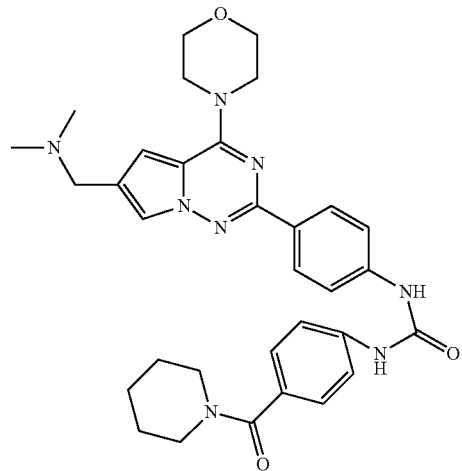
I-16
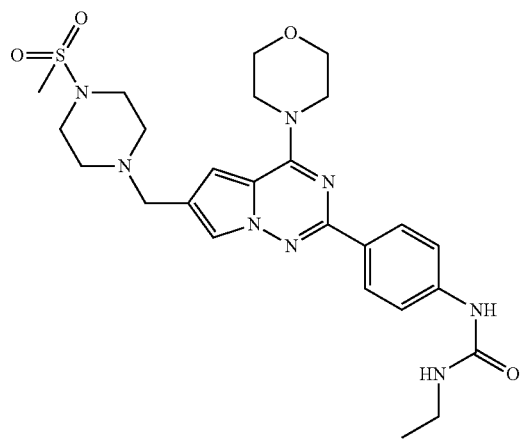 [SMILES: CCNC(=O)Nc1ccc(-c2nc(N3CCOCC3)c3cc(CN4CCN(S(C)(=O)=O)CC4)cn3n2)cc1]
I-17
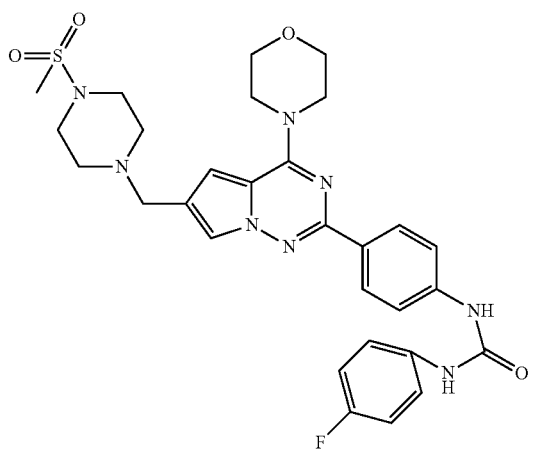 [SMILES: CS(=O)(=O)N1CCN(Cc2cc3c(N4CCOCC4)nc(-c4ccc(NC(=O)Nc5ccc(F)cc5)cc4)nn3c2)CC1]
I-18

TABLE 1-continued
The structures of representative compounds of general formula I
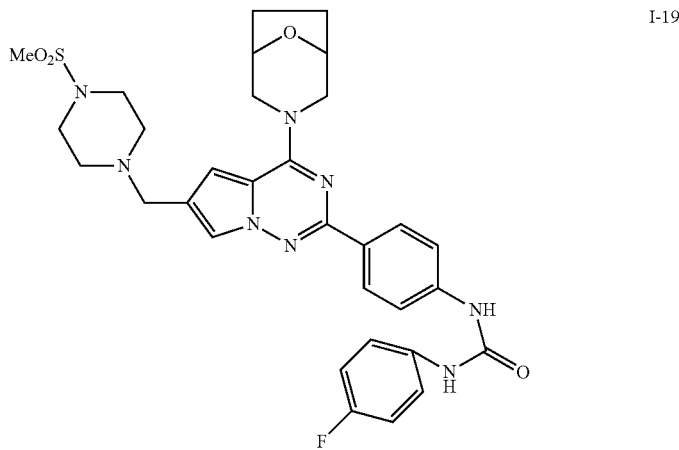
I-19
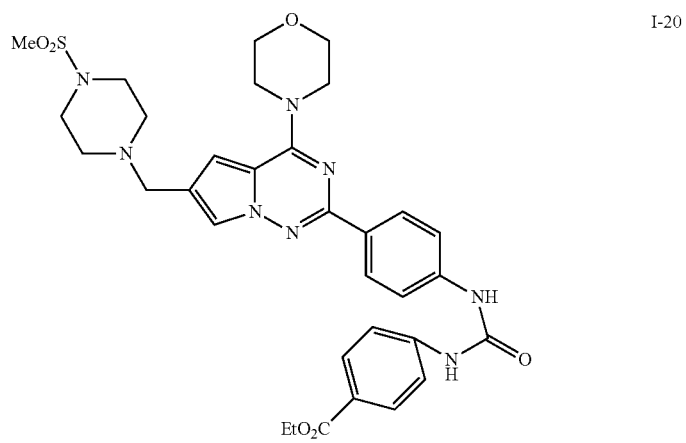
I-20
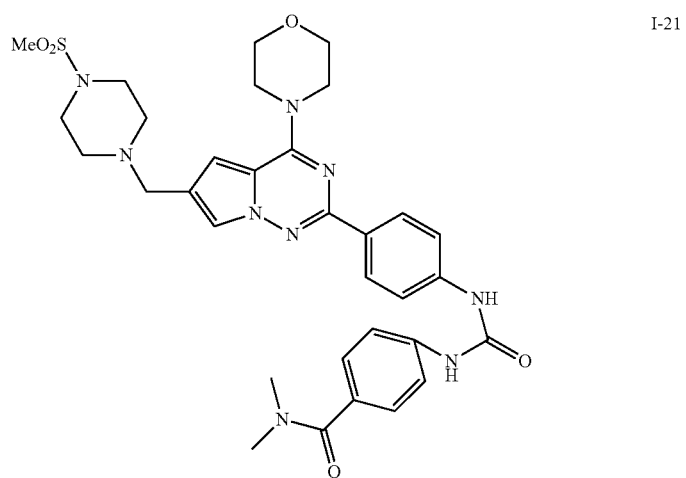
I-21

TABLE 1-continued
The structures of representative compounds of general formula I
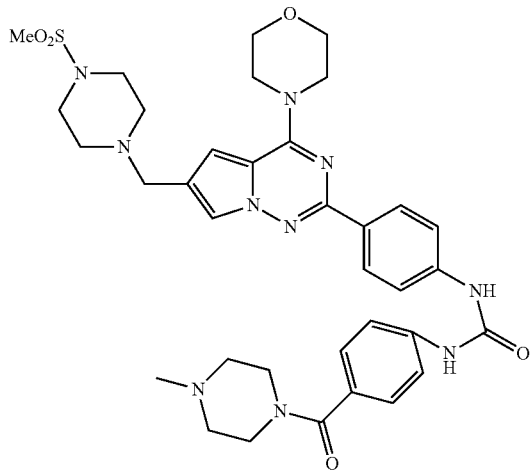
I-22
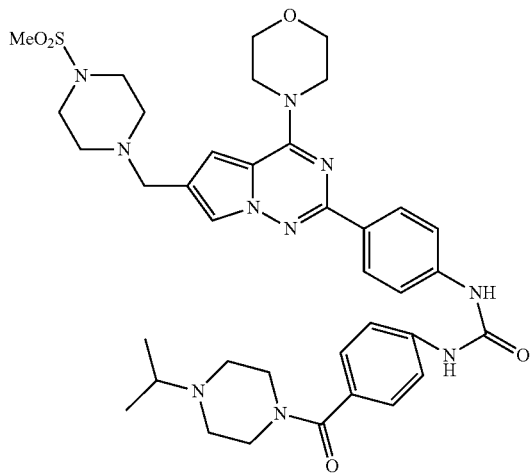 [SMILES: CC(C)N1CCN(C(=O)c2ccc(NC(=O)Nc3ccc(-c4nc(N5CCOCC5)c5cc(CN6CCN(S(C)(=O)=O)CC6)cn5n4)cc3)cc2)CC1]
I-23
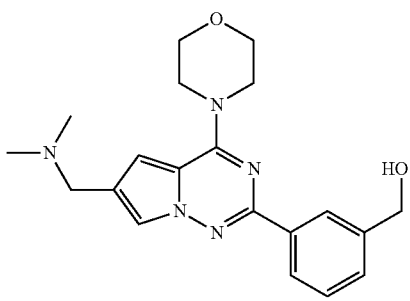 [SMILES: CN(C)Cc1cc2c(N3CCOCC3)nc(-c3cccc(CO)c3)nn2c1]
I-24
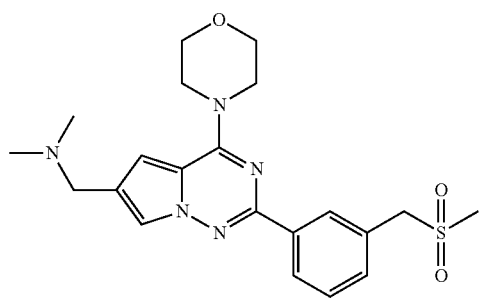
I-25

TABLE 1-continued
The structures of representative compounds of general formula I
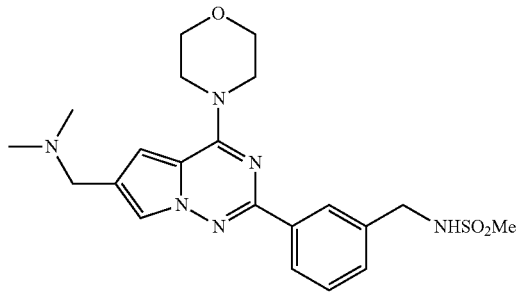
I-26
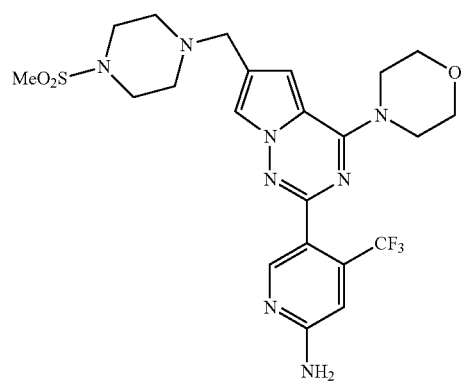 [SMILES: CS(=O)(=O)N1CCN(Cc2cc3c(N4CCOCC4)nc(-c4cnc(N)cc4C(F)(F)F)nn3c2)CC1]
I-27
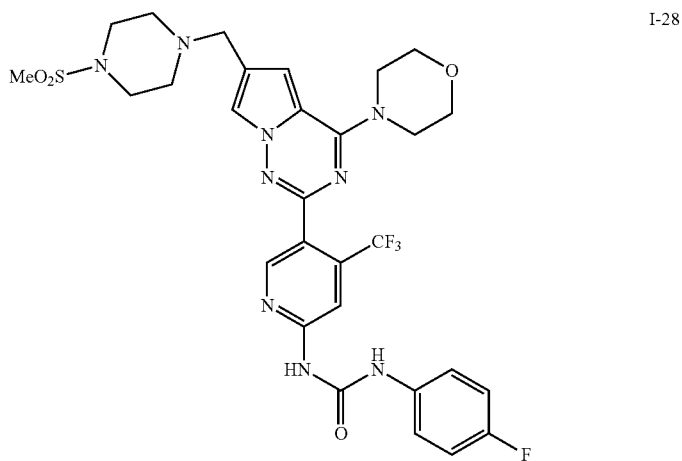
I-28
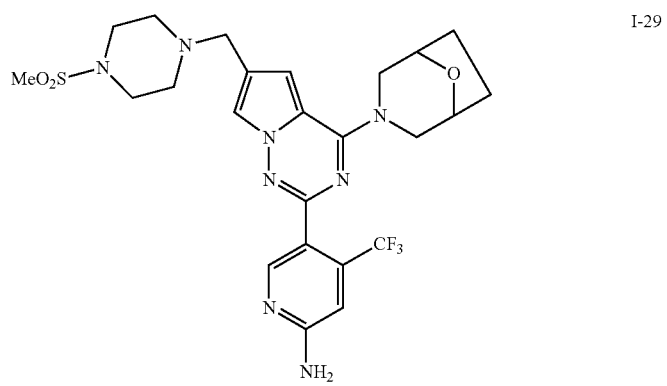
I-29

TABLE 1-continued
The structures of representative compounds of general formula I
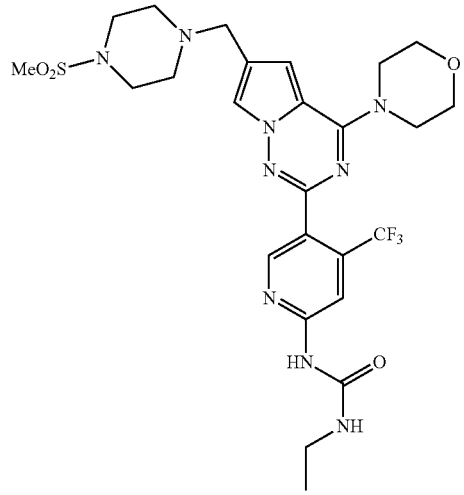
I-30
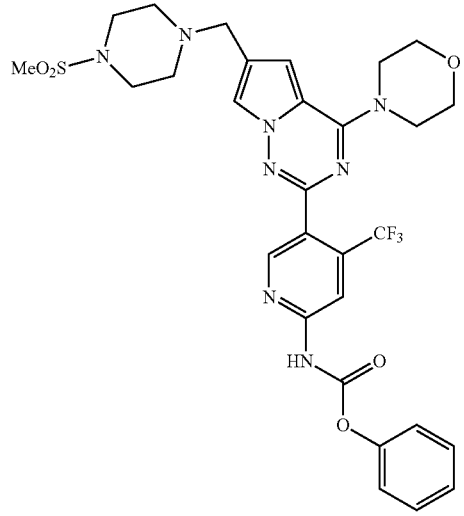 [SMILES: CS(=O)(=O)N1CCN(Cc2cc3c(N4CCOCC4)nc(-c4cnc(NC(=O)Oc5ccccc5)cc4C(F)(F)F)nn3c2)CC1]
I-31
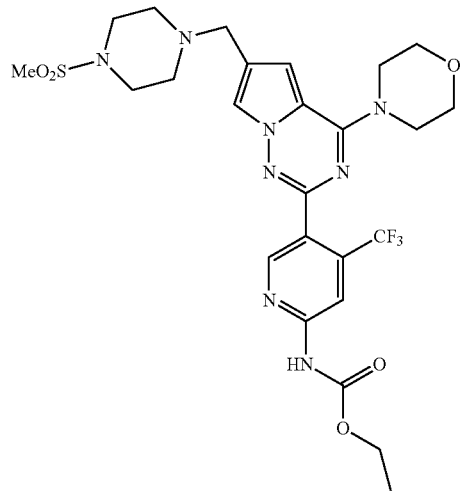 [SMILES: CCOC(=O)Nc1cc(C(F)(F)F)c(-c2nc(N3CCOCC3)c3cc(CN4CCN(S(C)(=O)=O)CC4)cn3n2)cn1]
I-32

TABLE 1-continued
The structures of representative compounds of general formula I
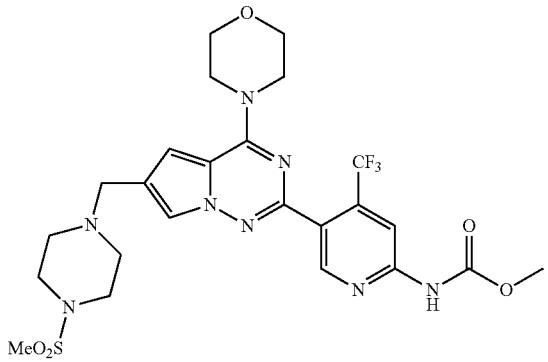
I-33
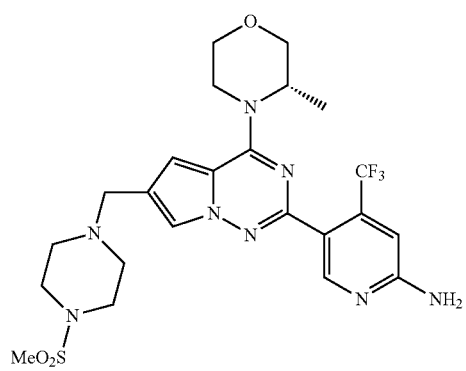 [SMILES: C[C@H]1COCCN1c1nc(-c2cnc(N)cc2C(F)(F)F)nn2cc(CN3CCN(S(C)(=O)=O)CC3)cc12]
I-34
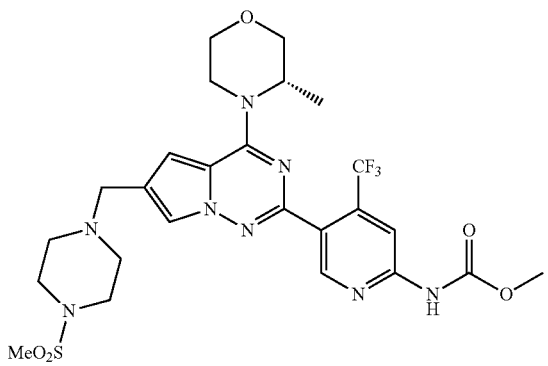 [SMILES: COC(=O)Nc1cc(C(F)(F)F)c(-c2nc(N3CCOC[C@@H]3C)c3cc(CN4CCN(S(C)(=O)=O)CC4)cn3n2)cn1]
I-35
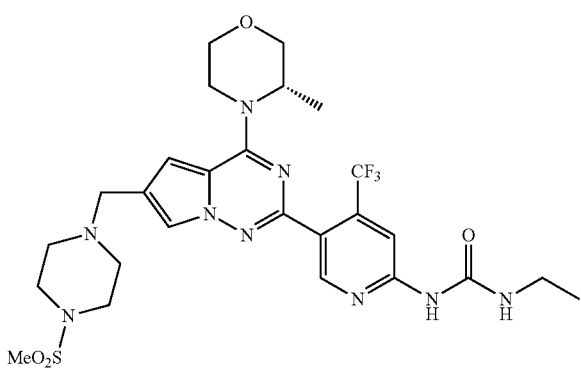 [SMILES: CCNC(=O)Nc1cc(C(F)(F)F)c(-c2nc(N3CCOC[C@@H]3C)c3cc(CN4CCN(S(C)(=O)=O)CC4)cn3n2)cn1]
I-36

TABLE 1-continued
The structures of representative compounds of general formula I
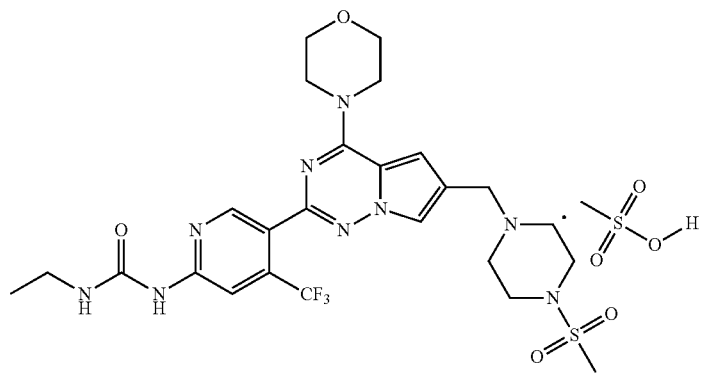
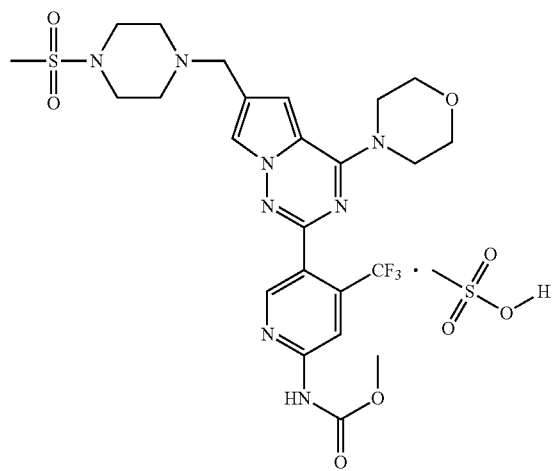
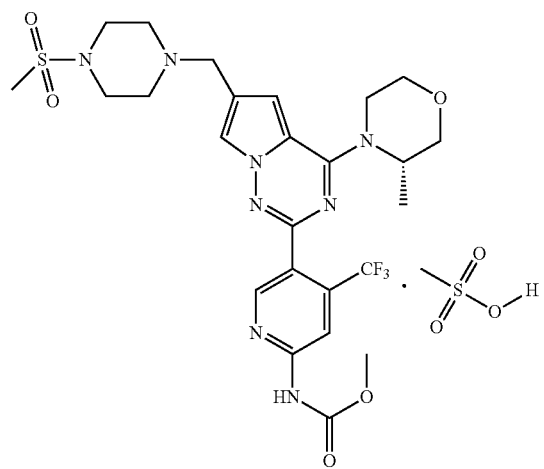

Another object of the present invention is to provide a preparation method for the compounds represented by general formula I, the preparation method comprising the following steps:

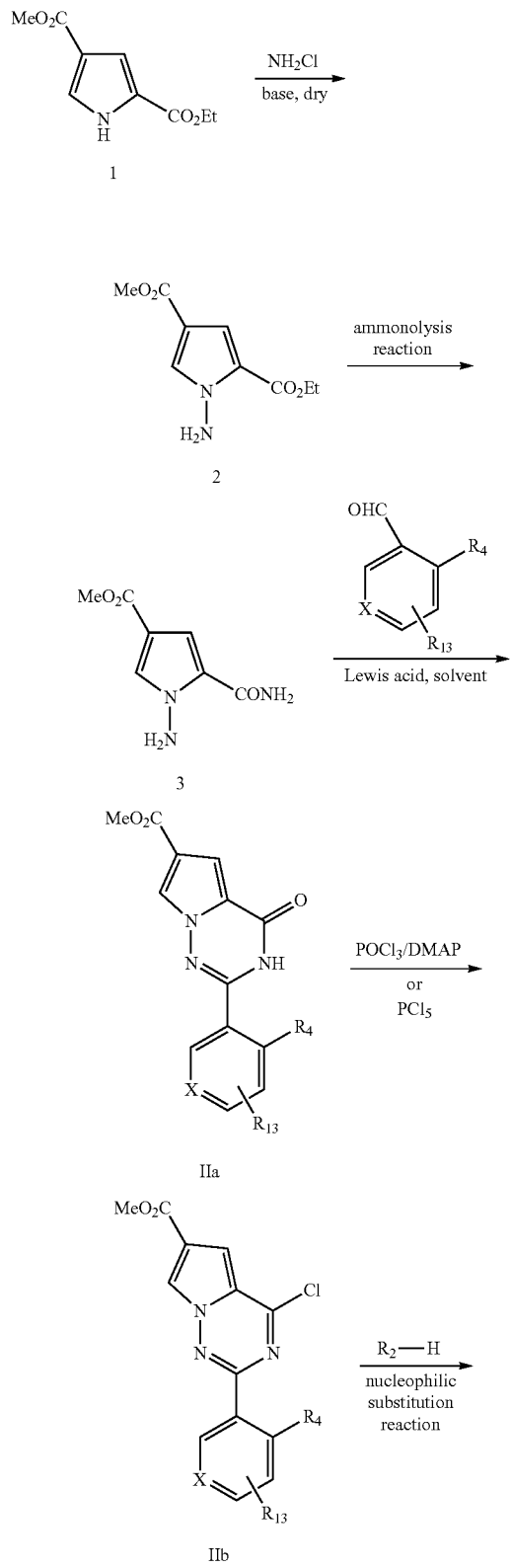

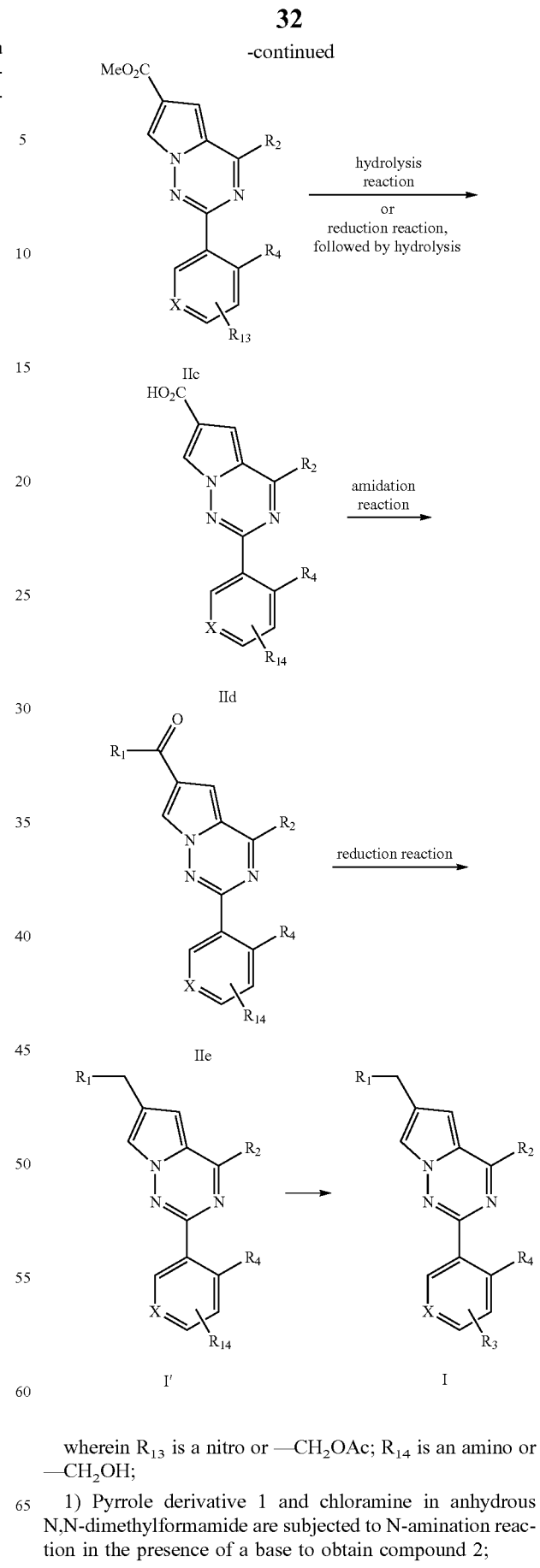

wherein $R_{13}$ is a nitro or —$CH_2OAc$; $R_{14}$ is an amino or —$CH_2OH$;

1) Pyrrole derivative 1 and chloramine in anhydrous N,N-dimethylformamide are subjected to N-amination reaction in the presence of a base to obtain compound 2;

The base may be sodium hydride, potassium carbonate or potassium tert-butoxide;

2) The compound represented by Formula 2 without being further purified is subjected to ammonolysis to give compound 3;

3) compound 3 reacts with an aromatic aldehyde under the action of metal Lewis acid to give compound IIa, or compound 3 and an aldehyde, under catalysis by Lewis acid such as a solution of boron trifluoride in diethyl ether, are subjected to condensation to give a Schiff base, and then oxidative cyclization to give compound IIa;

The metal Lewis acid can be a monovalent or divalent copper reagent, such as cuprous bromide, cuprous chloride, copper acetate monohydrate, copper bromide, anhydrous copper chloride, copper chloride dihydrate and the like. Preferably copper chloride dihydrate is used for its higher yield and easy post-processing compared with other copper reagents. The reaction solvent is dimethyl sulfoxide or N,N-dimethylformamide, N,N-dimethylacetamide, and the reaction temperature is 80-150° C.;

4) Compound IIa is subjected to chlorination to give compound IIb;

The chlorination agent is phosphorus oxychloride or phosphorus pentachloride, and the base used is N,N-dimethylaniline or 4-dimethylaminopyridine (DMAP);

5) Compound IIb and morpholine or a morpholine derivative are subjected to nucleophilic substitution reaction to give compound IIc;

6) The ester of compound IIc is subjected to hydrolysis reaction; or the nitro of compound IIc is subjected to reduction first, and then the ester group of IIc is hydrolyzed;

7) Compound IId reacts with an amine or a substituted/unsubstituted saturated heterocycle containing one nitrogen atom to give compound IIe;

the amine here is dimethylamine or methylsulfonyl piperazine;

8) Compound IIe is reduced by a reducing agent to give compound I';

the reducing agent here is borane-tetrahydrofuran complex or borane-dimethyl sulfide complex;

9) compound I' is further subjected to (addition reaction with $R_{11}NCO$, to esterification or amidation with $R_{11}OC(O)Cl$, to esterification or amidation with $R_{11}C(O)OH$ or $R_{11}C(O)Cl$, or to esterification reaction or amidation reaction with $R_{12}S(O)_2Cl$), to form the compounds represented by general formula I.

Particularly, the compounds represented by general formula Ia-If can be prepared by the following steps:

(1) Synthesis of the compounds represented by general formula IIIa-IIIc and synthesis of N-(5-formyl-4-(trifluoromethyl)pyridin-2-yl)pivalamide (7)

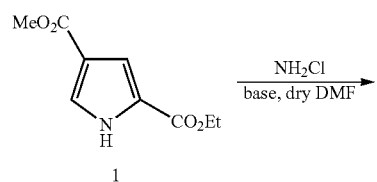

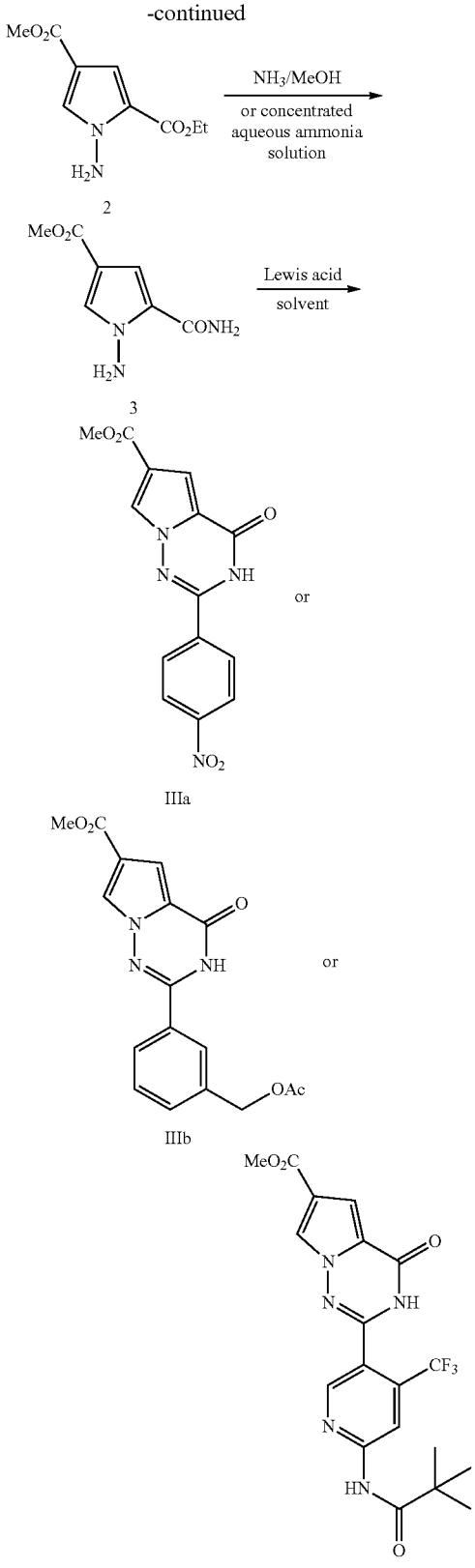

pyrrole derivative 1 and chloramine in dry N,N-dimethylformamide are subjected to N-amination reaction in the presence of a base to obtain compound 2, wherein the base may be sodium hydride, potassium carbonate or potassium tert-butoxide. Without further being purified, the crude product 2 is directly ammonolyzed in a sealed tube by using saturated solution of ammonia in methanol or commercially available concentrated aqueous ammonia solution to give compound 3. Compound 3 reacts with the corresponding aromatic aldehyde (eg. p-nitrobenzaldehyde, 3-formyl-benzyl acetate, N-(5-formyl-4-(trifluoromethyl)pyridin-2-yl) pivalamide) in the presence of a suitable metal Lewis acid to give compounds IIIa, IIIb, or IIIc. compounds IIIa, IIIb, or IIIc are also obtained by the condensation of compound 3 and various aldehydes in the presence of Lewis acid such as boron trifluoride solution in diethyl ether to give a Schiff base, and followed by oxidative cylclization. Wherein the metal Lewis acid can be a monovalent or divalent copper reagent, such as cuprous bromide, cuprous chloride, copper acetate monohydrate, copper bromide, anhydrous copper chloride, copper chloride dihydrate and the like. Compared with other copper reagent, higher yields can be obtained by using copper chloride dihydrate, and post-processing is easier. The reaction solvent is dimethyl sulfoxide or N,N-dimethylformamide, N,N-dimethylacetamide, and the reaction temperature is 80-150° C.

pound 10, the ester group of which is hydrolyzed under a basic condition to give acid 11. Compound 11 and an amine, such as dimethylamine or methylsulfonyl piperazine, etc., are subjected to a condensation to give compound 12. Then 12 is reduced by a reducing agent to give compound 13, wherein the reducing agent can be borane-tetrahydrofuran complex or borane-dimethyl sulfide complex. The reductive product 13 reacts with a series of isocyanates in anhydrous dichloromethane at room temperature, or with the corresponding acyl azide in dioxane at reflux to give Ia. When $R_{11}$ is 4-ethoxycarbonyl-phenyl, Ia is hydrolyzed to give compound 14. Compound 14 and dimethylamine, N-methylpiperazine or 4-dimethylaminopiperidine are subjected to condensation to give Ib.

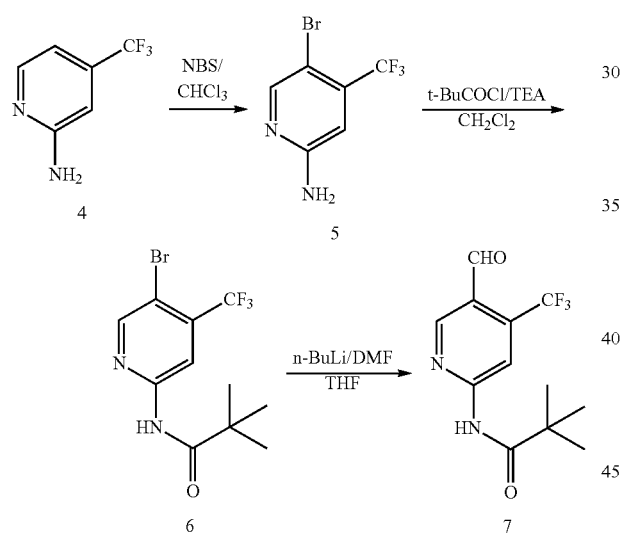

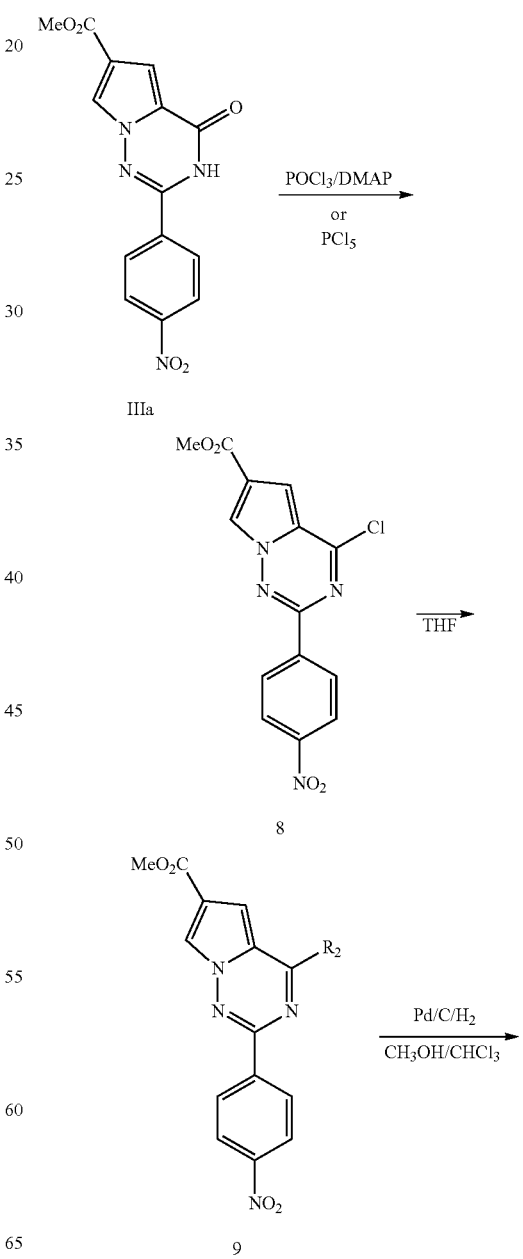

Wherein, aldehyde 7 is obtained by a three-step procedure. 2-amino-4-trifluoromethyl-pyridine (4) is brominated by N-bromosuccinimide in chloroform to give compound 5. The amino group of compound 5 is protected with a pivaloyl group, and then compound 7 is obtained using n-butyl lithium and N,N-dimethylformamide in anhydrous tetrahydrofuran.

(2) synthesis of pyrrolo[2,1-f][1,2,4]triazine derivatives Ia and Ib wherein X=CH and $R_3$ is NHC(O)NHR$_{11}$ Compound IIIa is chlorinated by phosphorus oxychloride or phosphorus pentachloride to give product 8, which reacts with morpholine or its analogue at room temperature in tetrahydrofuran to obtain compound 9. Compound 9 is reduced by 5% or 10% palladium on carbon to give com-

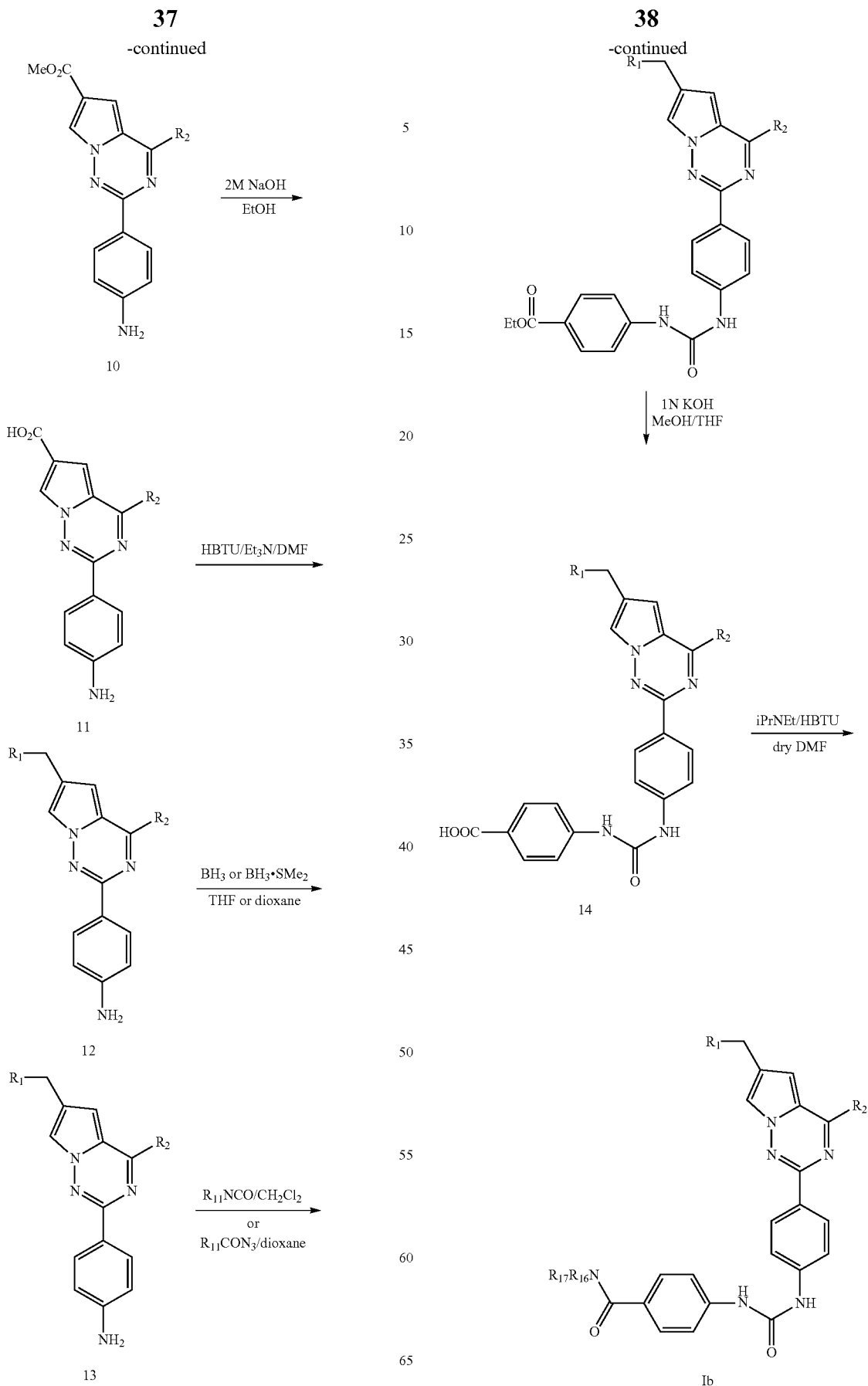

(3) synthesis of pyrrolo[2,1-f][1,2,4]triazine derivatives Ic-e wherein X=CH and $R_3$ is $CH_2OH$, $CH_2S(O)_2R_{12}$ or $CH_2NHS(O)_2R_{12}$
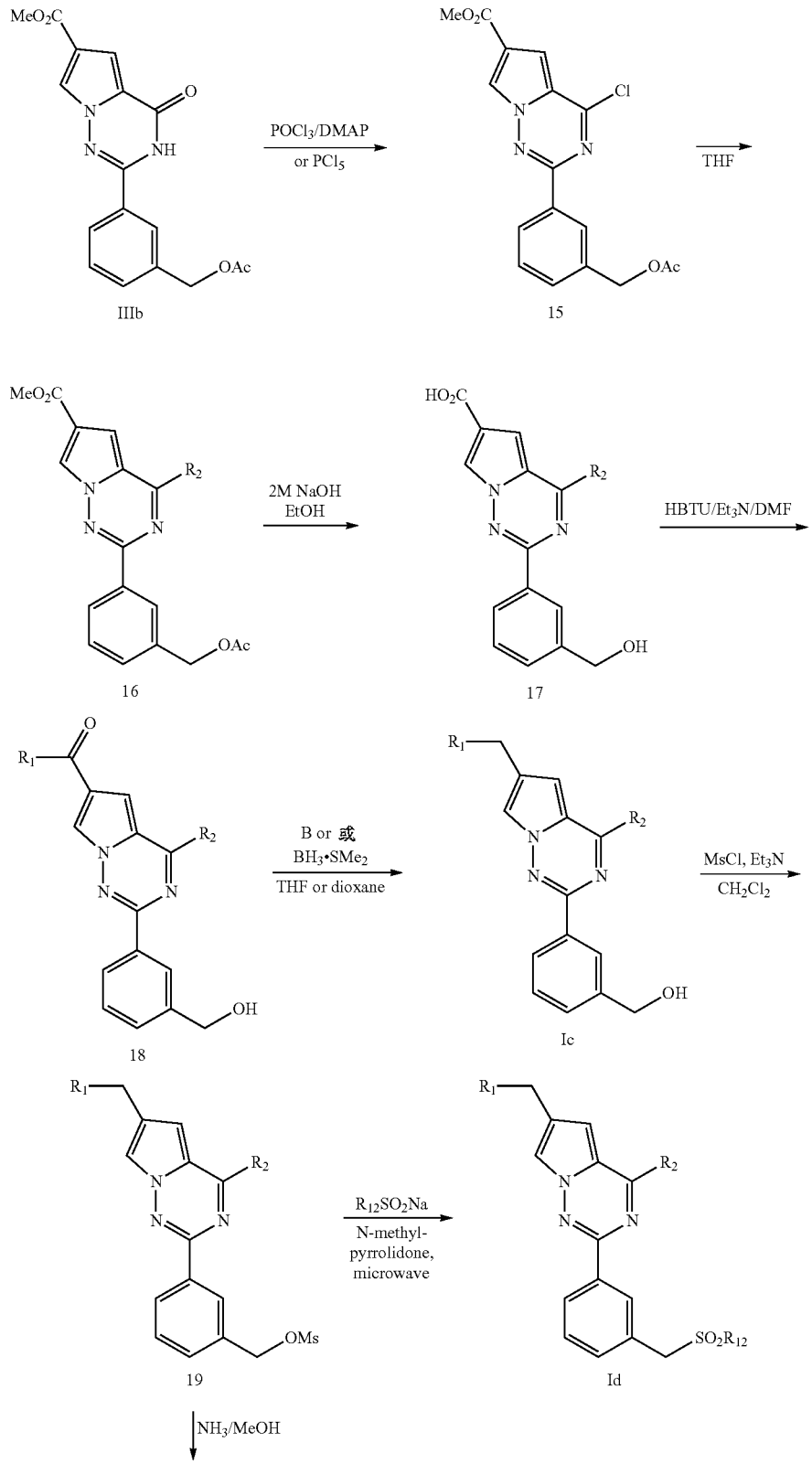

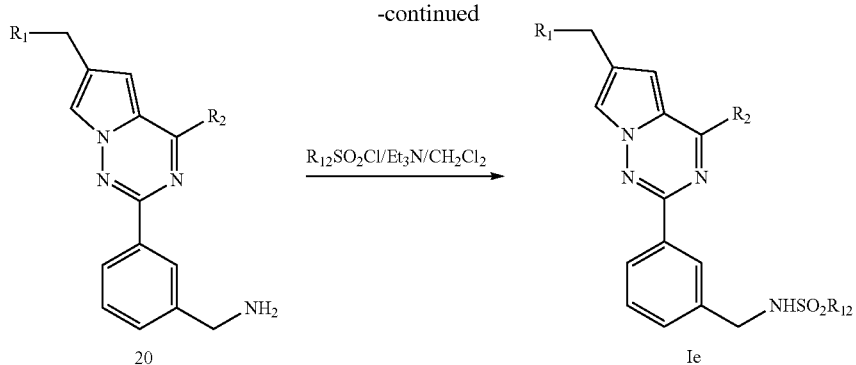

Chlorinated compound IIIb reacts with morpholine or its analogue thereof at room temperature in tetrahydrofuran to obtain compound 16. The ester group of compound 16 is hydrolyzed to give compound 17. 17 and amine, such as dimethylamine or methylsulfonyl piperazine, etc., are subjected to condensation to give compound 18, and then 18 is reduced by a borane-tetrahydrofuran solution or borane-dimethyl sulfide solution to give Ic. With the methylsulfonyl chloride, the hydroxyl of Ic is converted to good leaving group methanesulfonate, and turned to be compound 19. Compound 19 reacts with sodium alkyl sulfonate under microwave irradiation in N-methylpyrrolidone at 120° C. for 30 mins to give compound Id. Furthermore, compound 19 is subjected to ammonolysis to give compound 20, which then reacts with alkyl sulfonyl chloride to give compound Ie.

(4) synthesis of pyrrolo[2,1-f][1,2,4]triazine derivatives If-Ig wherein X=N, $R_3$ is $NH_2$, $NHC(O)NHR_{11}$, or $NHC(O)OR_{11}$, and $R_4$ is $CF_3$

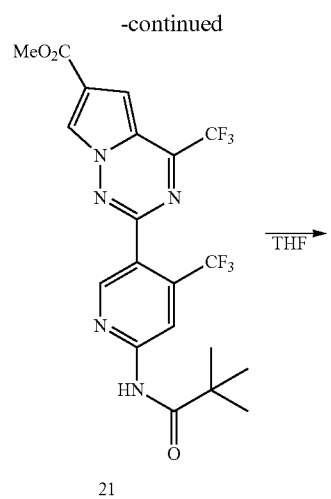

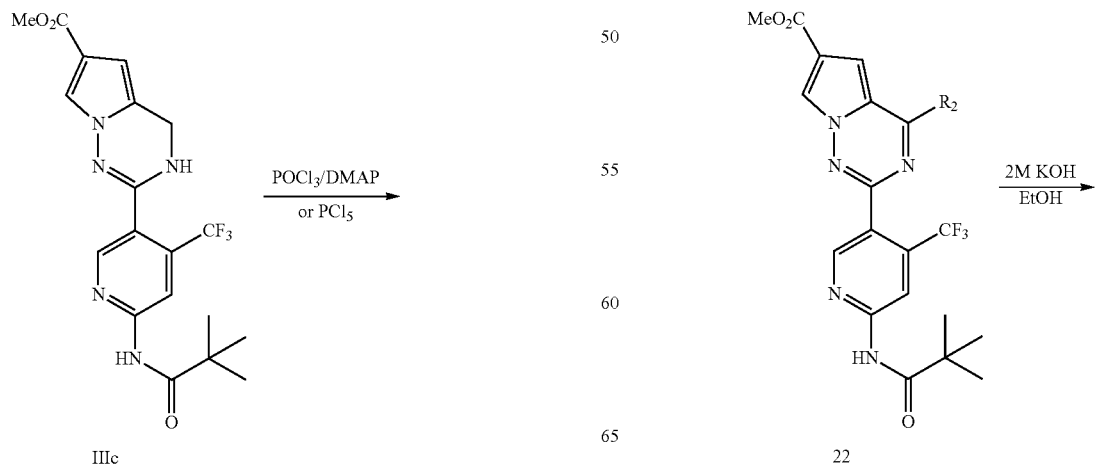

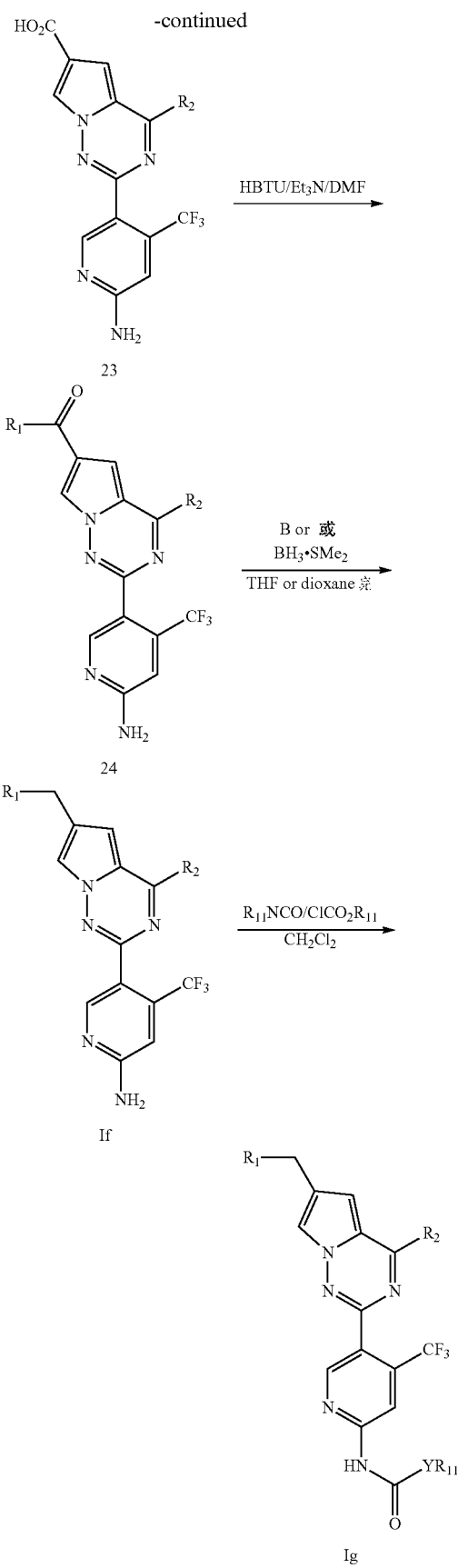

Chlorinated compound IIIc reacts with morpholine or its analogue in tetrahydrofuran at room temperature to obtain compound 22. The ester group of compound 22 is hydrolyzed to give product 23. 23 and an amine or a substituted or unsubstituted saturated heterocycle are subjected to condensation to give compound 24, which is then reduced by a borane-tetrahydrofuran solution or borane-dimethyl sulfide solution to give If. Compound If reacts with isocyanate or chloroformate in anhydrous dichloromethane at room temperature to obtain Ig.

The compounds according to the present invention can efficiently inhibit the activity of PI3K kinase. Therefore, these compounds can be used in the treatment of diseases associated with PI3K pathway, in particular for the treatment of tumors. Further, the present invention provides a use of the compounds of general formula I or pharmaceutically acceptable salts thereof for the preparation of phosphatidylinositol 3-kinase and the mammalian target protein of rapamycin inhibitor medicaments, i.e., for the preparation of medicaments for treating phosphatidylinositol 3-kinase-related diseases. The phosphatidylinositol 3-kinase-related diseases include tumors. The tumors include human rhabdomyosarcoma, non-small cell lung cancer, human glioma, prostate cancer, ovarian cancer, liver cancer, colon cancer, breast cancer and so on.

Moreover, the present invention provides a pharmaceutical composition comprising any of the compounds of formula I described herein, an isoformer, a pharmaceutically acceptable salt, ester, or hydrate thereof. In some embodiments, the amount of the compound of formula I in the pharmaceutical composition is 1-1,000 mg (e.g., 10-500 mg). Any of the pharmaceutical compositions described herein may further comprises a pharmaceutically acceptable carrier, which may be cellulose (including derivatives thereof such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, or a combination thereof. In some examples, the pharmaceutical composition may be in the form of capsule, tablet, pill, powder, granule, emulsion, solution, suspension, syrup or tincture.

Further, the present invention provides a method for a phosphatidylinositol 3-kinase-related disease (such as cancer), the method comprising administering to a subject in need thereof (e.g., a human cancer patient) an effective amount of any of the pharmaceutically acceptable compositions described herein, which comprise one or more of the compounds of formula I also described herein. In some embodiments, the subject may be administered with 1-1000 mg (e.g., 10-500 mg) of the compound daily. In some embodiments, the subject is a human patient having rhabdomyosarcoma, non-small cell lung cancer, glioma, prostate cancer, ovarian cancer, liver cancer, colon cancer, breast cancer, or esophageal cancer.

The details of one or more embodiments of the invention are set forth in the description below. Other features or advantages of the present invention will be apparent from the following drawings and detailed description of several embodiments, and also from the appended claims.

DETAILED DESCRIPTIONS

Figure 1:
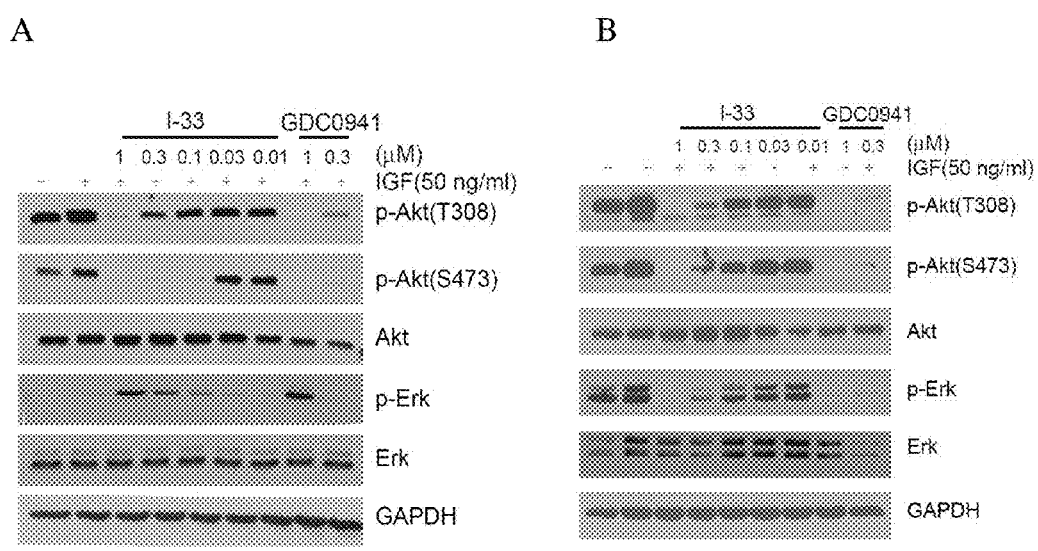
FIG. 1 shows the effects of I-33 on the PI3K signal pathway of human rhabdomyosarcoma Rh30 cells and human glioma U87MG cells.

The present disclosure is based on the development of pyrrolo[2,1-f][1,2,4]triazine compounds, which showed strong inhibitory activity against PI3K. PI3K was known to be involved in various diseases and disorders, such as various types of cancers. Accordingly, such compounds are expected to be effective in cancer treatment. Indeed, the present studies demonstrated that exemplary pyrrolo[2,1-f][1,2,4]triazine compounds successfully inhibited growth of various types of cancers, either in vitro or in vivo.

Accordingly, the present disclosure provides pyrrolo[2,1-f][1,2,4]triazine compounds, pharmaceutical compositions comprising such, and methods of using such for treating diseases and disorders associated with PI3K, including cancer Pharmaceutical Compositions One or more of the pyrrolo[2,1-f][1,2,4]triazine compound as described herein can be mixed with a pharmaceutically acceptable carrier (e.g., excipient) to form a pharmaceutical composition for use in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The pharmaceutical compositions to be used in the present methods can comprise pharmaceutically acceptable carriers, excipients, or stabilizers in the form of lyophilized formulations or aqueous solutions. See, e.g., Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In some examples, the pharmaceutical composition described herein comprises liposomes containing the pyrrolo[2,1-f][1,2,4]triazine compound, which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The pyrrolo[2,1-f][1,2,4]triazine compounds as described herein may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the pyrrolo[2,1-f][1,2,4]triazine compound, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic pyrrolo[2,1-f][1,2,4]triazine compound-containing compositions may be placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets having a suitable size and can have a pH in the range of 5.5 to 8.0.

The emulsion compositions can be those prepared by mixing a pyrrolo[2,1-f][1,2,4]triazine compound with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulized by use of gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

In some embodiments, the pharmaceutical composition comprises 1-1000 mg of a pyrrolo[2,1-f][1,2,4]triazine compound. In some embodiments, the pharmaceutical composition comprises 1-900 mg, 1-800 mg, 1-700 mg, 1-600 mg, 1-500 mg, 1-400 mg, 1-300 mg, 1-200 mg, or 1-100 mg of the pyrrolo[2,1-f][1,2,4]triazine compound. In some embodiments, the pharmaceutical composition comprises 100-900 mg, 200-900 mg, 300-900 mg, 400-900 mg, 500-900 mg, 600-900 mg, 700-900 mg, or 800-900 mg of the pyrrolo[2,1-f][1,2,4]triazine compound.

In some embodiments, the pharmaceutical composition comprises 10-500 mg of a pyrrolo[2,1-f][1,2,4]triazine compound. In some embodiments, the pharmaceutical composition comprises 10-400 mg, 10-300 mg, 10-200 mg, 10-100 mg, 10-50 mg, or 10-25 mg of the pyrrolo[2,1-f][1,2,4]triazine compound. In some embodiments, the pharmaceutical composition comprises 10-500 mg, 25-500 mg, 50-500 mg, 100-500 mg, 200-500 mg, 300-500 mg, or 400-500 mg of the pyrrolo[2,1-f][1,2,4]triazine compound.

Methods of Treatment

Any of the pyrrolo[2,1-f][1,2,4]triazine compounds as described herein can be used in treating a disease or disorder associated with PI3K. In some instances, the disease is a cancer. Examples include, but are not limited to, human rhabdomyosarcoma, non-small cell lung cancer, human glioma, prostate cancer, ovarian cancer, liver cancer, colon cancer, breast cancer, or esophageal cancer.

To practice the method disclosed herein, an effective amount of the pharmaceutical composition described herein that contains at least one of the pyrrolo[2,1-f][1,2,4]triazine compounds can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, the pyrrolo[2,1-f][1,2,4]triazine compound as described herein can be aerosolized using a fluorocarbon formulation and a metered dose inhaler, or inhaled as a lyophilized and milled powder.

As used herein, "an effective amount" refers to the amount of each active agent required to confer therapeutic effect on the subject, either alone or in combination with one or more other active agents. In some embodiments, the therapeutic effect is reduced tumor burden, reduction of cancer cells, or decreased activity of PI3K. Determination of whether an amount of the pyrrolo[2,1-f][1,2,4]triazine compound achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. Frequency of administration may be determined and adjusted over the course of therapy, and is generally, but not necessarily, based on treatment and/or suppression and/or amelioration and/or delay of a target disease/disorder. Alternatively, sustained continuous release formulations of a pyrrolo[2,1-f][1,2,4]triazine compound may be appropriate. Various formulations and devices for achieving sustained release are known in the art.

In one example, dosages for a pyrrolo[2,1-f][1,2,4]triazine compound as described herein may be determined empirically in individuals who have been given one or more administration(s) of the pyrrolo[2,1-f][1,2,4]triazine compound. Individuals are given incremental dosages of the pyrrolo[2,1-f][1,2,4]triazine compound. To assess efficacy of the pyrrolo[2,1-f][1,2,4]triazine compound, an indicator of the disease/disorder can be followed.

Generally, for administration of any of the pyrrolo[2,1-f][1,2,4]triazine compounds described herein, an initial candidate dosage can be about 2 mg/kg. For the purpose of the present disclosure, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate a target disease or disorder, or a symptom thereof. An exemplary dosing regimen comprises administering an initial dose of about 2 mg/kg, followed by a weekly maintenance dose of about 1 mg/kg of the pyrrolo[2,1-f][1,2,4]triazine compound, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the pyrrolo[2,1-f][1,2,4]triazine compound used) can vary over time.

In some embodiments, for an adult patient of normal weight, doses ranging from about 0.3 to 5.00 mg/kg may be administered. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of a pyrrolo[2,1-f][1,2,4]triazine compound as described herein will depend on the specific pyrrolo[2,1-f][1,2,4]triazine compound, the type and severity of the disease/disorder, whether the pyrrolo[2,1-f][1,2,4]triazine compound is administered for preventive or therapeutic purposes, previous therapy, the patient's clinical history and response to the pyrrolo[2,1-f][1,2,4]triazine compound, and the discretion of the attending physician. A clinician may administer a pyrrolo[2,1-f][1,2,4]triazine compound, until a dosage is reached that achieves the desired result. In some embodiments, the desired result is a decrease in tumor burden, a decrease in cancer cells, or decreased activity of PI3K. Methods of determining whether a dosage resulted in the desired result would be evident to one of skill in the art. Administration of one or more pyrrolo[2,1-f][1,2,4]triazine compounds can be continuous or intermittent, depending, for example, upon the recipient's physiological condition, whether the purpose of the administration is therapeutic or prophylactic, and other factors known to skilled practitioners. The administration of a pyrrolo[2,1-f][1,2,4]triazine compound may be essentially continuous over a preselected period of time or may be in a series of spaced dose, e.g., either before, during, or after developing a target disease or disorder.

As used herein, the term "treating" refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity. Alleviating the disease does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

In some embodiments, the pyrrolo[2,1-f][1,2,4]triazine compounds described herein are administered to a subject in need of the treatment at an amount sufficient to reduce tumor burden or cancer cell growth, by at least 5% (e.g., 10%, 20%, 30%, 40%, 50%, 60%, 70%, 80%, 90% or greater) in vivo. In other embodiments, the pyrrolo[2,1-f][1,2,4]triazine compounds are administered in an amount effective in reducing the activity level of PI3K by at least 5% (e.g., 10%, 20%, 30%, 40%, 50%, 60%, 70%, 80%, 90% or greater).

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods. In some examples, the pharmaceutical composition is administered intraocularlly or intravitreally.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble pyrrolo[2,1-f][1,2,4]triazine compounds can be administered by the drip method, whereby a pharmaceutical formulation containing the pyrrolo[2,1-f][1,2,4]triazine compound and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the PDL1 binding aptamer, can be dissolved and administered in a pharmaceutical excipient such as Water-for-Injection, 0.9% saline, or 5% glucose solution.

In one embodiment, a pyrrolo[2,1-f][1,2,4]triazine compound is administered via site-specific or targeted local delivery techniques. Examples of site-specific or targeted local delivery techniques include various implantable depot sources of the pyrrolo[2,1-f][1,2,4]triazine compound or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

The subject to be treated by the methods described herein can be a mammal, such as a farm animals, sport animals, pets, primates, horses, dogs, cats, mice and rats. In one example, the subject is a human. The pyrrolo[2,1-f][1,2,4]triazine compound-containing composition may be used for treating cancer, for example, esophageal cancer, in a subject in need of the treatment. In some examples, the subject may be a human patient having, suspected of having, or at risk for a cancer, such as esophageal cancer, human rhabdomyosarcoma, non-small cell lung cancer, human glioma, prostate cancer, ovarian cancer, liver cancer, colon cancer, or breast cancer. Such a patient can also be identified by routine medical practices.

A subject having a target disease or disorder (e.g., cancer such as esophageal cancer) can be identified by routine medical examination, e.g., laboratory tests, organ functional tests, CT scans, or ultrasounds. A subject suspected of having any of such target disease/disorder might show one or more symptoms of the disease/disorder. A subject at risk for the disease/disorder can be a subject having one or more of the risk factors associated with that disease/disorder. Such a subject can also be identified by routine medical practices.

The particular dosage regimen, i.e., dose, timing and repetition, used in the method described herein will depend on the particular subject (e.g., a human patient) and that subject's medical history.

In some embodiments, the pyrrolo[2,1-f][1,2,4]triazine compound may be co-used with another suitable therapeutic agent (e.g., an anti-cancer agent). Alternatively or in addition, the pyrrolo[2,1-f][1,2,4]triazine compound may also be used in conjunction with other agents that serve to enhance and/or complement the effectiveness of the agents.

Treatment efficacy for a target disease/disorder can be assessed by, e.g., a method described in the Examples below.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

The present invention will be further illustrated by the following examples, but these examples do not limit the invention in any way. In all examples, $^1$H NMR was recorded with Brucher AM-400 or GEMINI-300 nuclear magnetic resonance spectrometers, wherein the chemical shift is represented by δ (ppm). Mass spectrum was recorded with MAT-95 mass spectrometer. The 200-300 mesh of silica gels were used for separation.

Example 1

Synthesis of exemplary pyrrolo[2,1-f][1,2,4]triazine compounds

1. Preparation of methyl 1-amino-5-carbamoyl-1H-pyrrole-3-carboxylate (3)

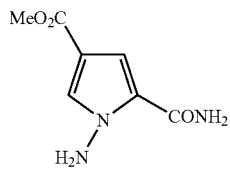

The mixture of 9 g ammonium chloride and 330 mL diethyl ether was cooled to −20° C. and 15 mL of concentrated aqueous ammonia solution was added with a dropper. 216 mL of 5% (mass percentage) of sodium hypochlorite solution was dropped via a constant pressure dropping funnel. The mixture was stirred at −10° C. for 30 minutes. After separation, the organic layer was washed with saturated brine (chloramine is unstable and the brine should be pre-cooled). Anhydrous calcium chloride was added into the organic layer and the mixture was dried at −40° C. for 1 hour before use.

The compound pyrrole-1,3-dicarboxylate 1 (5 g, 25.4 mmol, prepared according to Kamijo, S., Kanazawa, C., and Yamamoto Y. *J. AM. CHEM. SOC.* 2005, 127, 9260-9266, wherein the starting materials methyl propiolate and ethyl isocyanoacetate were purchased from Darui chemical Co., Ltd) was dissolved in 25 mL of anhydrous N,N-dimethylformamide, and cooled in an ice bath to 0° C. Sodium hydride (60%, dispensed in mineral oil, 1.22 g, 30.5 mmol) was added in batches. The mixture was stirred for 1 hour at room temperature. Then 300 mL of chloramine solution in diethyl ether prepared in advance was added in one portion and stirred overnight at room temperature under nitrogen atmosphere. The reaction mixture was quenched with saturated sodium thiosulfate solution and diluted with water. The diethyl ether layer was separated and the aqueous layer was extracted once with ethyl acetate. The organic layers were combined and washed with water for three times, dried over anhydrous sodium sulfate, and concentrated under reduced pressure to give 6.2 g of crude product which is directly subjected to ammonolysis without purification. To each 3 g of crude product was added 80 mL of saturated solution of ammonia in methanol and the reaction was carried out at 80° C. in a sealed tube for 2 days. The reaction mixture was concentrated to precipitate solid, then allowed to settle for about 1 hour, and filtered to obtain 3 g product as white solid. The yield of two ste
was 64.6%. m.p. 222-224° C.
$^1$H NMR (300 MHz, DMSO-d$_6$): δ 7.95 (br s, 1H), 7.38 (s, 1H), 7.33 (br s, 1H), 7.15 (s, 1H), 6.87 (s, 2H), 3.70 (s, 3H). MS (EI) m/z (%): 183 (M$^+$, 100).

2. Preparation of 2-amino-4-trifluoromethyl-5-bromopyridine (5)

2-amino-4-trifluoromethylpyridine (5 g, 30.8 mmol, Langfang Beixin Chemical Co., Hebei) was dissolved in 100 mL of chloroform and N-bromosuccinimide (5.92 g, 33.3 mmol) was added in batches. The mixture was stirred in darkness or away from light at room temperature for 3 hours. The reaction mixture was concentrated and purified by column chromatography with gradient elution (petroleum ether:ethyl acetate=10:1 and dichloromethane), so as to give 4.33 g of red solid. Yield: 58.2%. LC-MS: 240 (M+1), 242 (M+2+1).

3. Preparation of N-(5-bromo-4-(trifluoromethyl) pyridin-2-yl) pivalamide (6)

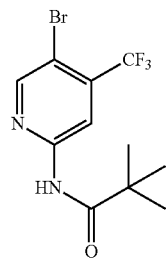 [SMILES: CC(C)(C)C(=O)Nc1cc(C(F)(F)F)c(Br)cn1]

In an ice bath, 29.8 g of pivaloyl chloride (226 mmol) was added dropwise to a solution of compound 5 (50.0 g, 207 mmol) and triethylamine (37.9 mL) in dichloromethane (300.0 mL) within one hour and then stirred for 2 hours until the starting materials disappeared. 150 mL of water was added into the reaction solution and stirred at room temperature for 10 minutes. The organic layer was separated, dried over anhydrous sodium sulfate, concentrated, and separated through a short column with ethyl acetate to give white solid (57.7 g, 85.6%).
m.p. 126-128° C. $^1$H NMR (300 MHz, CDCl$_3$): δ 8.67 (s, 1H), 8.50 (s, 1H), 8.14 (brs, 1H), 1.33 (s, 9H).

4. Preparation of N-(5-formyl-4-(trifluoromethyl) pyridin-2-yl) pivalamide (7)

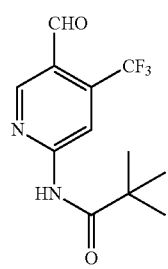 [SMILES: CC(C)(C)C(=O)Nc1cc(C(F)(F)F)c(C=O)cn1]

Compound 6 (15.0 g, 46.2 mmol) was dissolved in 350 mL of anhydrous tetrahydrofuran and cooled to −78° C. under nitrogen. 45 mL of 2.5 M n-butyl lithium solution in tetrahydrofuran was slowly added to the reaction solution within one hour. The reaction solution was stirred at −78° C. for 1 hour, and then 15 mL of anhydrous N,N-dimethylformamide was slowly added dropwise and stirred for another 2.5 h at −78° C. To the reaction solution was added 120 mL of 1 M diluted hydrochloric acid to quench the reaction. The reaction mixture was extracted with ethyl acetate (200 mL×3). The organic layers were combined and washed with water (200 mL×3), saturated brine (200 mL) respectively, then dried over anhydrous sodium sulfate and filtered. The filtrate was concentrated and purified by column chromatography (petroleum ether:dichloromethane: ethyl acetate=60:10:1) to give 7.1 g of white solid (56.1%). m.p. 96-98° C. $^1$H NMR (300 MHz, CDCl$_3$): δ 10.32 (br s, 1 H), 9.01 (s, 1 H), 8.73 (s, 1 H), 8.40 (s, 1 H), 1.38 (s, 9 H).

5. General Preparation Method for Compounds IIIa-IIIc 5 mL of dimethylsulfoxide was added to a mixture of compound 3 (55 mg, 0.3 mmol), corresponding aldehyde (0.3 mmol) and copper chloride dihydrate (51 mg, 0.3 mmol) and the reaction was performed at 80-150° C. After the reaction was finished, the reaction mixture was cooled and poured into water, the precipitated solids were filtered. If the crude product has poor solubility, it is washed with methanol. If it has good solubility, it is purified through column chromatography (dichloromethane:methanol=50:1).

Preparation of methyl 2-p-nitrophenyl-4-oxo-3,4-dihydropyrrolo[2,1-f][1,2,4]triazine-6-formate (IIIa)

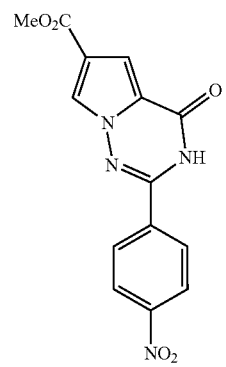 [SMILES: COC(=O)c1cc2c(=O)[nH]c(-c3ccc([N+](=O)[O-])cc3)nn2c1]

According to the general preparation method described in example 5 above, p-nitrobenzaldehyde reacts with compound 3 to give compound IIIa as light yellow solid in 72.0% yield. m.p.>300° C. $^1$H NMR (300 MHz, DMSO-d$_6$): δ 12.52 (s, 1H), 8.38 (d, J=8.5 Hz, 2H), 8.22 (s, 1H), 8.21 (d, J=8.5 Hz, 2H), 7.26 (s, 1H), 3.80 (s, 3H). LRMS (EI) m/z (%): 314 (M$^+$, 85), 283 (100). HRMS calcd. C$_{14}$H$_{10}$N$_4$O$_5$: 314.0651. found: 314.0659.

Preparation of methyl 2-(3-(acetoxylmethyl)phenyl)-4-oxo-3,4-dihydropyrrolo[2,1-f][1,2,4]triazine-6-carboxylate (IIIb)

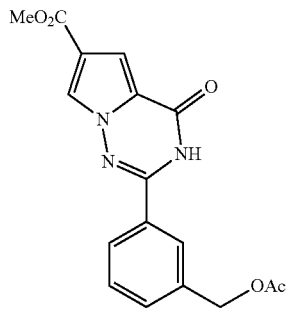 [SMILES: COC(=O)c1cc2c(=O)[nH]c(-c3cccc(COC(C)=O)c3)nn2c1]

According to the general preparation methods described in example 5 above, 3-formylbenzyl acetate reacts with compound 3 to give compound IIIb as offwhite solid in 39.0% yield. m.p. 202-203° C. ¹H NMR (300 MHz, DMSO-d₆): δ 12.29 (s, 1H), 8.19 (d, J=1.7 Hz, 1H), 7.96 (s, 1H), 7.92 (dt, J=1.7, 7.2 Hz, 1H), 7.58-7.53 (m, 2H), 7.24 (d, J=1.7 Hz, 1H), 5.16 (s, 2H), 3.81 (s, 3H), 2.10 (s, 3H). LC-MS: 342 (M+1).

Preparation of methyl 4-oxo-2-(6-pivalamido-4-(trifluoromethyl)-pyridin-3-yl)-3,4-dihydro pyrrolo[2,1-f][1,2,4]triazine-6-carboxylate (IIIc)

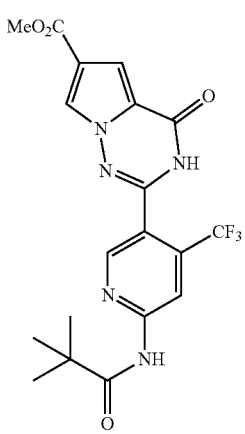 [SMILES: COC(=O)c1cc2c(=O)[nH]c(-c3cnc(NC(=O)C(C)(C)C)cc3C(F)(F)F)nn2c1]

According to the general preparation method described in example 5 above, compound 7 reacts with compound 3 to give compound IIIc as light yellow solid in 25.9% yield. m.p. 244-245° C. ¹H NMR (300 MHz, DMSO-d₆): δ 12.47 (s, 1H), 10.68 (s, 1H), 8.86 (s, 1H), 8.57 (s, 1H), 8.20 (d, J=1.7 Hz, 1H), 7.29 (d, J=1.7 Hz, 1H), 3.81 (s, 3H), 1.28 (s, 9H). LC-MS: 438 (M+1).

6. Preparation of methyl 2-p-nitrophenyl-4-chloropyrrolo[2,1-f][1,2,4]triazine-6-carboxylate (8)

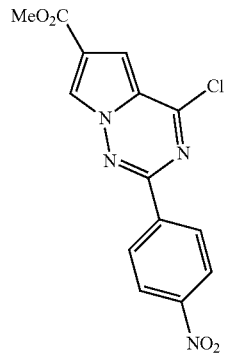 [SMILES: COC(=O)c1cc2c(Cl)nc(-c3ccc([N+](=O)[O-])cc3)nn2c1]

20 mL of phosphorus oxychloride was added to a mixture of compound IIIa (4.74 g, 15.1 mmol) and 4-dimethylamino pyridine (4.34 g, 35.6 mmol) and refluxed for 5 hours. After the reaction mixture was cooled, a portion of phosphorus oxychloride was distilled off under the reduced pressure. The residue was poured into crushed ice, filtered and dried to give yellow solid (4.6 g, 91.8%). m.p. 218-223° C. ¹H NMR (300 MHz, CDCl₃): δ 8.54 (d, J=8.9 Hz, 2H), 8.36 (s, 1H), 8.34 (d, J=8.9 Hz, 2H), 7.46 (d, J=1.3 Hz, 1H), 3.96 (s, 3H). MS (EI) m/z (%): 332 (M⁺, 100), 334 (M+2, 33).

7. Preparation of Compound 9

Methyl 2-(p-nitrophenyl)-4-(morpholinyl)-pyrrolo[2,1-f][1,2,4]triazine-6-carboxylate (9a)

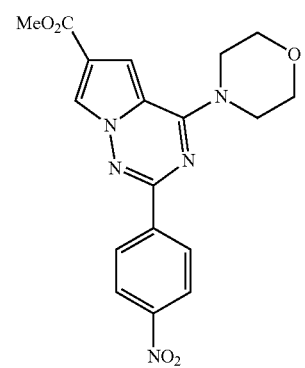

Compound 8 (4.6 g, 13.8 mmol) was suspended in 150 mL of tetrahydrofuran, 3.6 mL of morpholine was added dropwise and reacted for 5 hours at room temperature. 3.9 g of solid was obtained by filteration, and the filtrate was separated through a column chromatography with dichloromethane to give 1.1 g of yellow compound 9a (94.3%). m.p. 296-300° C. ¹H NMR (300 MHz, CDCl₃): δ 8.45 (d, J=8.7 Hz, 2H), 8.29 (d, J=8.7 Hz, 2H), 8.14 (d, J=1.3 Hz, 1H), 7.23 (d, J=1.3 Hz, 1H), 4.17 (t, J=4.8 Hz, 4H), 3.91 (t, J=4.8 Hz, 7H). LC-MS: 384 (M+1).

Methyl 4-(8-oxa-3-azabicylclo[3.2.1]octan-3-yl)-2-(p-nitrophenyl)pyrrolo[2,1-f][1,2,4]triazine-6-carboxylate (9b)

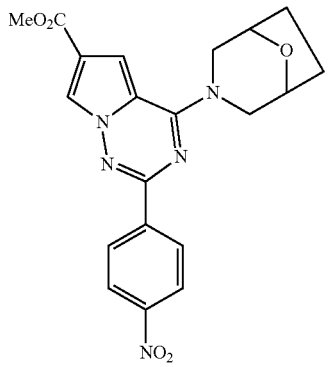

Compound 8 (100 mg, 0.3 mmol) was suspended in 15 mL of tetrahydrofuran, and 8-oxa-3-azabicylclo[3.2.1]octane hydrochloride (54 mg, 0.36 mmol) and one drop of triethylamine were added and reacted for 3-4 h at room temperature. The solvent was removed under the reduced pressure. The residue was washed with water, dried and purified through column chromatography with dichloromethane, so as to give 109 mg of yellow solid 9b (88.6%). m.p. 278-280° C. $^1$H NMR (300 MHz, CDCl$_3$): δ 8.45 (d, J=9.0 Hz, 2H), 8.29 (d, J=9.0 Hz, 2H), 8.13 (d, J=1.3 Hz, 1H), 7.21 (d, J=1.3 Hz, 1H), 4.60 (br s, 4H), 3.91 (s, 3H), 3.63 (br, s, 2H), 2.08-2.04 (m, 2H), 1.91-1.84 (m, 2H). LC-MS: 410 (M+1).

8. General Preparation Method of Compound 10

A mixed solvent of methanol and chloroform (500 mL, 1:1), and 10 wt % palladium on carbon of starting material (10% Pd-Carbon) were added to compound 9 (13 mmol) and reduced for 24 hours under hydrogen atmosphere at room temperature. Palladium-carbon was filtrated off by celite, and the filtrate was concentrated under reduced pressure to quantitatively obtain Compound 10.

Methyl 2-(p-aminophenyl)-4-(morpholinyl)pyrrolo[2,1-f][1,2,4]triazine-6-carboxylate (10a)

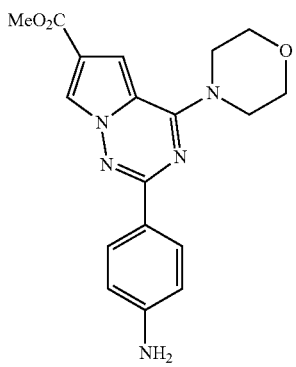 [SMILES: COC(=O)c1cc2c(N3CCOCC3)nc(-c3ccc([N+](=O)[O-])cc3)nn2c1]

10a was prepared from 9a according to the general preparation method of compound 10. White solid, m.p. 238-240° C. $^1$H NMR (300 MHz, DMSO-d$_6$): δ 8.13 (d, J=1.6 Hz, 1H), 7.93 (d, J=8.5 Hz, 2H), 7.31 (d, J=1.6 Hz, 1H), 6.62 (d, J=8.5 Hz, 2H), 5.70 (br, s, 2H), 4.04 (t, J=4.5 Hz, 4H), 3.80 (s, 3H), 3.77 (t, J=4.5 Hz, 4H). MS (EI) m/e (%): 353 (M$^+$, 100).

Methyl 2-(p-aminophenyl)-4-(8-oxa-3-azabicylclo[3.2.1]octan-3-yl)pyrrolo[2,1-f][1,2,4]triazine-6-carboxylate (10b)

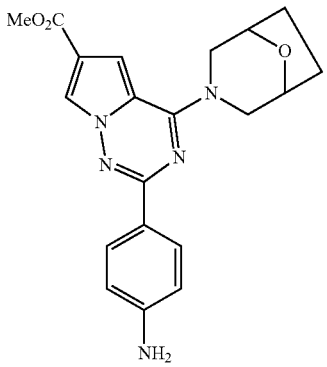 [SMILES: COC(=O)c1cc2c(N3CC4CCC(C3)O4)nc(-c3ccc(N)cc3)nn2c1]

10b was prepared from 9b according to the general preparation method of compound 10. Yellow solid. m.p. 254-256° C. $^1$H NMR (300 MHz, DMSO-d$_6$): δ 8.21(s, 1H), 8.19 (d, J=8.7 Hz, 2H), 7.34 (s, 1H), 7.22 (d, J=8.7 Hz, 2H), 4.53 (br s, 4H), 3.81 (s, 3H), 3.49 (br, s, 2H), 1.89-1.85 (m, 2H), 1.78-1.75 (m, 2H). LC-MS: 380 (M+1).

9. Preparation Method of Compound 11

2-(p-aminophenyl)-4-(morpholinyl)pyrrolo[2,1-f][1,2,4]triazine-6-carboxylic acid (11a)

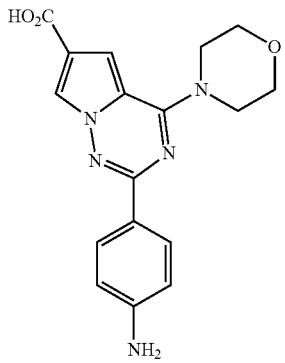

Compound 10a (14 mmol) was suspended in 150 mL of ethanol, and 30 mL of 2 M aqueous sodium hydroxide solution was added. The reaction mixture was refluxed to be a clear solution and the reaction was substantially completed. 2 mL of acetic acid was added. Most of the solvent was distilled off under reduced pressure, and the precipitates were filtered to give compound 11a (3.25 g, 68.5%). m.p.>300° C. $^1$H NMR (300 MHz, DMSO-d$_6$): δ 7.91(d, J=8.8 Hz, 2H), 7.71 (d, J=1.2 Hz, 1H), 6.99 (d, J=1.2 Hz, 1H), 6.59 (d, J=8.8 Hz, 2H), 5.49 (s, 2H), 4.02 (t, J=4.4 Hz, 4H), 3.77 (t, J=4.4 Hz, 4H). MS (EI) m/e (%): 339 (M⁺, 100).

2-(p-aminophenyl)-4-(8-oxa-3-azabicylclo[3.2.1]octan-3-yl)pyrrolo[2,1-f][1,2,4]triazine-6-carboxylic acid (11b)

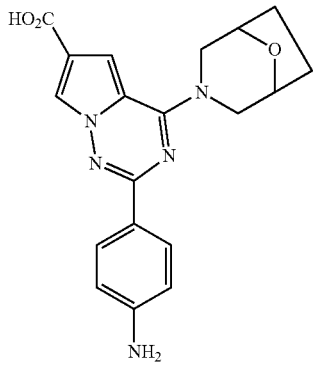 [SMILES: Nc1ccc(-c2nc(N3CC4CCC(C3)O4)c3cc(C(=O)O)cn3n2)cc1]

According to the same procedure as the preparation of compound 11a, 360 mg of 10b (0.95 mmol) as the starting material was hydrolyzed to give compound 11b (270 mg, 77.9%). m.p. 278-280° C. ¹H NMR (300 MHz, DMSO-d₆): δ 12.46 (s, 1H), 8.04 (d, J=1.7 Hz, 1H), 7.92 (d, J=8.8 Hz, 2H), 7.22 (d, J=1.7 Hz, 1H), 6.60 (d, J=8.8 Hz, 2H), 5.55 (br s, 2H), 4.51 (br s, 4H), 3.48 (br, s, 1H), 3.44(br, s, 1H), 1.88-1.85 (m, 2H), 1.79-1.75 (m, 2H). LC-MS: 366 (M+1).

10. General Preparation Method of Compound 12

2-(p-aminophenyl)-N,N-dimethyl-4-morpholinopyrrolo[2,1-f][1,2,4]triazine-6-carboxamide (12a)

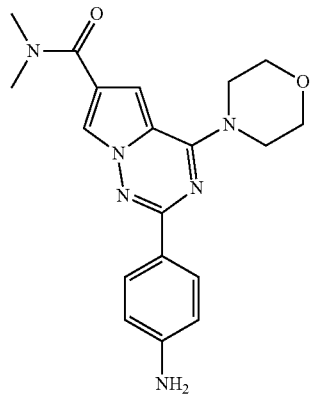 [SMILES: CN(C)C(=O)c1cc2c(N3CCOCC3)nc(-c3ccc(N)cc3)nn2c1]

Dimethylamine hydrochloride (686 mg, 8.4 mmol) was added to 30 mL of anhydrous N,N-dimethylformamide, and potassium carbonate (3.48 g, 25.2 mmol) was added and stirred for 30 minutes at room temperature. Then compound 11a (4.2 mmol), HBTU (benzotriazole-N,N,N',N'-tetramethyluronium hexafluorophosphate, 4.77 g, 12.6 mmol), and triethylamine (2.9 mL, 21 mmol) were added and reacted overnight at room temperature under nitrogen atmosphere. The reaction mixture was poured into water and filtered. The filtrate was extracted once with ethyl acetate, dried over anhydrous sodium sulfate, filtered and concentrated to dryness. The residue was combined with the filter cake. The crude product was purified by column chromatography (dichloromethane:methanol=100:1) to give white compound 12a (922 mg, 60.0%). m.p. 238-239° C. ¹H NMR (300 MHz, CDCl₃): δ 8.08 (d, J=8.6 Hz, 2H), 7.82 (d, J=1.4 Hz, 1H), 7.02 (d, J=1.4 Hz, 1H), 6.73 (d, J=8.6 Hz, 2H), 4.11 (t, J=4.4 Hz, 4H), 3.86 (t, J=4.4 Hz, 4H), 3.20 (br, s, 6H). MS (EI) m/e (%): 366 (M⁺, 100).

(2-(p-aminophenyl)-4-morpholinopyrrolo[2,1-f][1,2,4]triazin-6-yl)(4-(methylsulfonyl)piperazin-1-yl)methanone (12b)

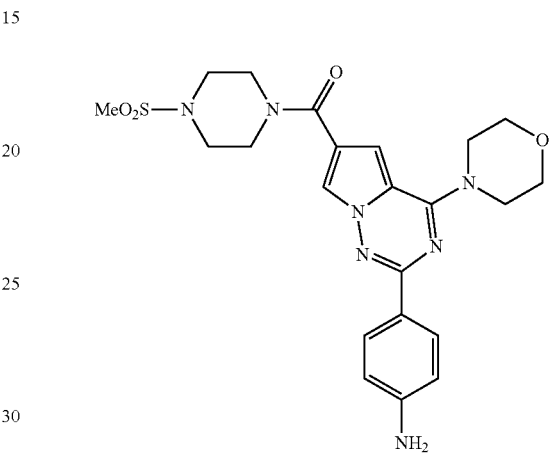

A white solid 12b (540 mg, 31.4%) was obtained according to the same procedure as the preparation of compound 12a, wherein 1.2 g of compound 11a (3.54 mmol) was used as starting material and methylsulfonylpiperazine trifluoromethanesulfonate (1.85 g, 7.1 mmol) was used instead of dimethylamine hydrochloride. m.p. 185-186° C. ¹H NMR (300 MHz, CDCl₃): δ 8.07 (d, J=8.6 Hz, 2H), 7.75 (d, J=1.5 Hz, 1H), 6.93 (d, J=1.5 Hz, 1H), 6.71 (d, J=8.6 Hz, 2H), 4.09 (t, J=4.8 Hz, 4H), 3.90 (t, J=4.8 Hz, 4H), 3.86 (t, J=4.8 Hz, 4H), 3.27 (t, J=4.8 Hz, 4H), 2.80 (s, 3H). LC-MS: 508 (M+23).

(2-(p-aminophenyl)-4-(8-oxa-3-azabicylclo[3.2.1]octan-3-yl)pyrrolo[2,1-f][1,2,4]triazin-6-yl)(4-(methylsulfonyl)piperazin-1-yl)methanone (12c)

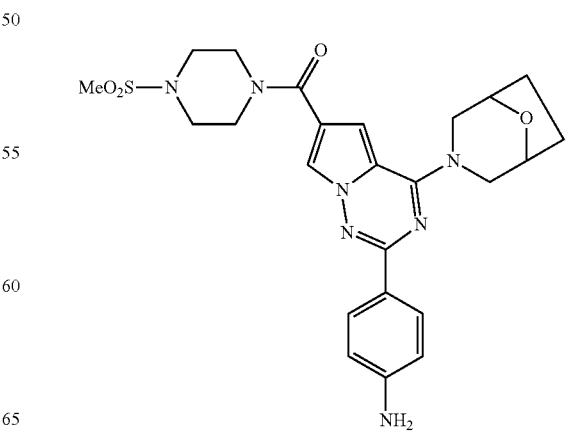

183 mg of compound 11b (0.5 mmol) was used instead of compound 11a, and compound 12c (120 mg, 46.8%) was obtained according to the same manner as the preparation of compound 12b. m.p.>300° C. $^1$H NMR (300 MHz, DMSO-$d_6$): δ 7.96 (s, 1H), 7.91 (d, J=8.5 Hz, 2H), 7.06 (s, 1H), 6.61 (d, J=8.5 Hz, 2H), 5.53 (s, 2H), 4.51 (br, s, 4H), 3.75 (t, J=4.5 Hz, 4H), 3.48 (br s, 1H), 3.43 (br s, 1H), 3.18 (t, J=4.5 Hz, 4H), 2.91 (s, 3H), 1.90-1.75 (m, 4H). LC-MS: 511 (M$^+$), 512 (M+1).

11. General Preparation Method of Compound 13

2-(p-aminophenyl)-6-(dimethylaminomethyl)-4-morpholinopyrrolo[2,1-f][1,2,4]triazine (13a)

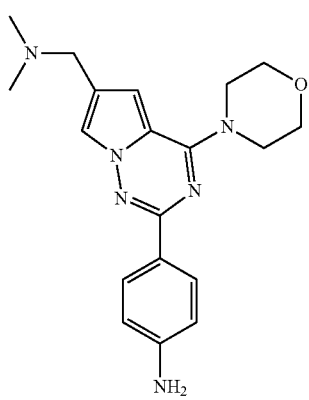 [SMILES: CN(C)Cc1cc2c(N3CCOCC3)nc(-c3ccc(N)cc3)nn2c1]

1 g of compound 12a (2.7 mmol) and 50 mL of tetrahydrofuran or dioxane were added into a 150 mL two-neck flask and refluxed under nitrogen atmosphere. 2 M of borane-dimethyl sulfide solution (10.8 mmol) was slowly added dropwise and refluxed for 2 hours. The reaction mixture was quenched with methanol and purified by column chromatography with dichloromethane to give white solid 13a (930 mg, 96.7%). m.p. 205° C. (decomposition). $^1$H NMR (300 MHz, DMSO-$d_6$): δ 7.92 (d, J=8.5 Hz, 2H), 7.86 (s, 1H), 7.05 (s, 1H), 6.60 (d, J=8.5 Hz, 2H), 5.48 (br s, 2H), 4.02 (t, J=4.5 Hz, 4H), 3.92 (s, 2H), 3.77 (t, J=4.5 Hz, 4H), 2.42 (s, 6H). MS (EI) m/e (%): 352 (M$^+$, 24).

2-(p-aminophenyl)-6-[((4-methylsulfonyl)piperazin-1-yl)methyl]-4-morpholinopyrrolo[2,1-f][1,2,4]triazine (13b)

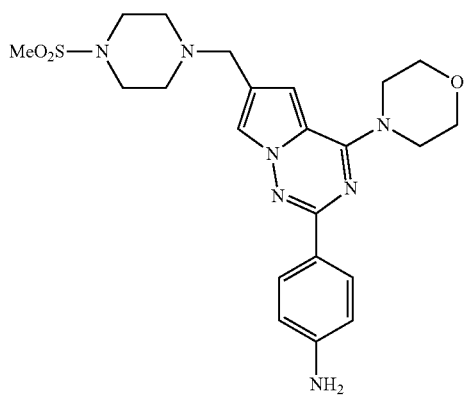 [SMILES: CS(=O)(=O)N1CCN(Cc2cc3c(N4CCOCC4)nc(-c4ccc(N)cc4)nn3c2)CC1]

Compound 12b (540 mg, 1.1 mmol) was used instead of compound 12a as starting material, and compound 13b (288 mg, 55.0%, white solid) was prepared according to the same preparation procedure of compound 13a. m.p. 199-200° C. $^1$H NMR (300 MHz, DMSO-$d_6$): δ 7.92 (d, J=8.6 Hz, 2H), 7.85 (d, J=1.4 Hz, 1H), 7.03 (d, J=1.4 Hz, 1H), 6.60 (d, J=8.6 Hz, 2H), 5.47 (s, 2H), 4.08 (s, 2H), 4.03 (t, J=4.6 Hz, 4H), 3.78 (t, J=4.6 Hz, 4H), 3.49-3.35 (m, 4H), 2.95 (s, 3H), 2.89 (t, J=5.7 Hz, 4H). MS (EI) m/e (%): 471 (M$^+$, 12).

4-(4-(8-oxa-3-azabicylclo[3.2.1]octan-3-yl)-6-((4-(methylsulfonyl)piperazin-1-yl)methyl) pyrrolo[2,1-f][1,2,4]triazin-2-yl)aniline (13c)

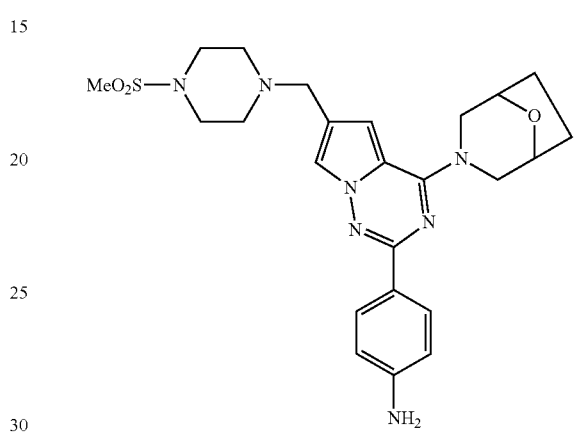

Compound 12c (100 mg, 0.195 mmol) was used instead of compound 12a as raw material, and compound 13c was prepared according to the same preparation procedure of compound 13a as a light yellow solid (39 mg, 40.1%). $^1$H NMR (300 MHz, DMSO-$d_6$): δ 7.89(d, J=8.4 Hz, 2H), 7.61 (s, 1H), 6.78 (s, 1H), 6.59 (d, J=8.4 Hz, 2H), 5.46 (br s, 2H), 4.50 (br, s, 4H), 3.56 (s, 2H), 3.43 (br s, 1H), 3.39 (br s, 1H), 3.30 (br s, 4H), 3.11 (br s, 4H), 2.86 (s, 3H), 1.88-1.85 (m, 2H), 1.78-1.75 (m, 2H). MS (EI) m/e (%): 497 (M$^+$, 12).

12. General Preparation Method of Compound I (1-13, 17-20)

1-ethyl-3-[4-(6-(dimethylaminomethyl)-4-morpholinopyrrolo[2,1-f][1,2,4]triazin-2-yl)phenyl]urea (I-1)

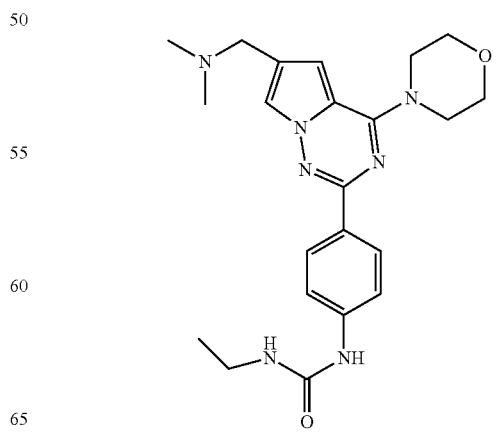

Compound 13a (0.15 mmol) was dissolved in 10 mL of anhydrous dichloromethane, and 3 equiv of ethyl isocyanate was added and stirred at room temperature overnight. The target compound was obtained by filtration.

White solid (22 mg, 34.6%). m.p. 222-224° C. $^1$H NMR (300 MHz, DMSO-d$_6$): δ 8.65 (s, 1H), 8.09 (d, J=8.8 Hz, 2H), 7.93 (s, 1H), 7.48 (d, J=8.8 Hz, 2H), 7.11 (s, 1H), 6.16 (t, J=5.8 Hz, 1H), 4.05 (t, J=4.5 Hz, 4H), 3.94 (s, 2H), 3.78 (t, J=4.5 Hz, 4H), 3.12 (quint, J=5.8, 7.1 Hz, 2H), 2.43 (s, 6H), 1.06 (t, J=7.1 Hz, 3H). ESI-MS: 424 (M+1).

1-propyl-3-[4-(6-(dimethylaminomethyl)-4-morpholinopyrrolo[2,1-f][1,2,4]triazin-2-yl)phenyl]urea (I-2)

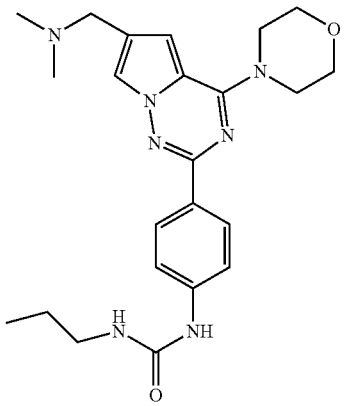 [SMILES: CCCNC(=O)Nc1ccc(-c2nc(N3CCOCC3)c3cc(CN(C)C)cn3n2)cc1]

The preparation process was identical with the preparation of I-1, except that ethyl isocyanate was replaced by propyl isocyanate. White solid (23 mg, 35.1%). m.p. 224-225° C. $^1$H NMR (300 MHz, DMSO-d$_6$): δ 8.64 (s, 1H), 8.09 (d, J=8.9 Hz, 2H), 7.93 (s, 1H), 7.48 (d, J=8.9 Hz, 2H), 7.11 (s, 1H), 6.20 (t, J=5.8 Hz, 1H), 4.05 (t, J=5.1 Hz, 4H), 3.94 (s, 2H), 3.78 (t, J=5.1 Hz, 4H), 3.05 (q, J=5.8, 7.2 Hz, 2H), 2.43 (s, 6H), 1.44 (sext, J=7.2 Hz, 2H), 0.88 (t, J=7.2 Hz, 3H). ESI-MS: 438 (M+1).

1-tert-butyl-3-[4-(6-(dimethylaminomethyl)-4-morpholinopyrrolo[2,1-f][1,2,4]triazin-2-yl)phen yl]urea (I-3)

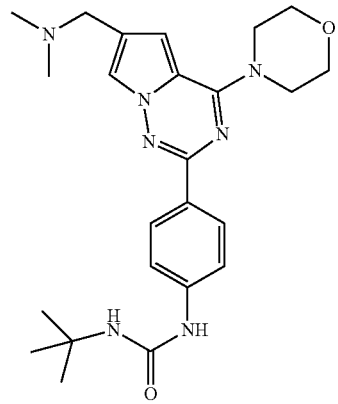 [SMILES: CN(C)Cc1cc2c(N3CCOCC3)nc(-c3ccc(NC(=O)NC(C)(C)C)cc3)nn2c1]

The preparation process was identical with the preparation of I-1, except that ethyl isocyanate was replaced by tert-butyl isocyanate. White solid (11 mg, 16.3%). m.p. 220-224° C. $^1$H NMR (300 MHz, DMSO-d$_6$): δ 8.49 (s, 1H), 8.08 (d, J=8.8 Hz, 2H), 7.93 (d, J=1.0 Hz, 1H), 7.44 (d, J=8.8 Hz, 2H), 7.11 (d, J=1.0 Hz, 1H), 6.07 (s, 1H), 4.05 (t, J=4.4 Hz, 4H), 3.94 (s, 2H), 3.78 (t, J=4.4 Hz, 4H), 2.42 (s, 6H), 1.30 (s, 9H). ESI-MS: 452 (M+1).

1-[4-(6-dimethylaminomethyl-4-morpholinopyrrolo[2,1-f][1,2,4]triazin-2-yl)phenyl]-3-(p-fluorophenyl)urea (I-4)

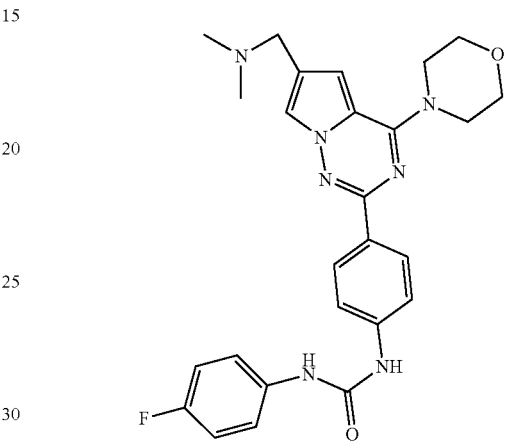

The preparation process was identical with the preparation of I-1, except that ethyl isocyanate was replaced by p-fluorophenyl isocyanate. White solid (30 mg, 40.9%). m.p. 217-219° C. $^1$H NMR (300 MHz, DMSO-d$_6$): δ 8.90 (s, 1H), 8.75 (s, 1H), 8.15 (d, J=8.7 Hz, 2H), 7.95 (s, 1H), 7.55 (d, J=8.7 Hz, 2H), 7.47 (dd, J=4.6, 8.8 Hz, 2H), 7.13 (t, J=8.8 Hz, 2H), 7.13 (s, 1H), 4.06 (t, J=4.6 Hz, 4H), 3.94 (s, 2H), 3.79 (t, J=4.6 Hz, 4H), 2.43 (s, 6H). ESI-MS: 490 (M+1).

1-[4-(6-dimethylaminomethyl-4-morpholinopyrrolo[2,1-f][1,2,4]triazin-2-yl)phenyl]-3-(p-chlorophenyl)urea (I-5)

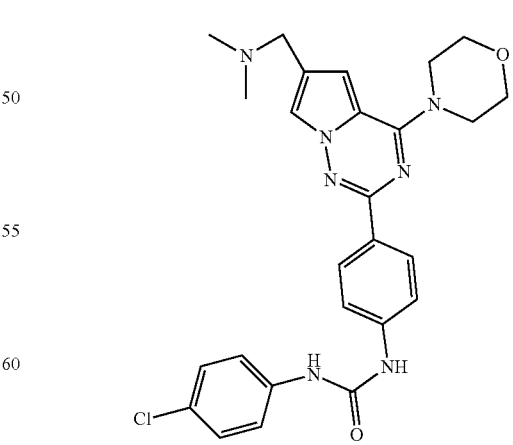

The preparation process was identical with the preparation of I-1, except that ethyl isocyanate was replaced by p-chlorophenyl isocyanate. White solid (43 mg, 56.8%).

m.p. 237° C. (decomposition). ¹H NMR (300 MHz, DMSO-d₆): δ 8.95 (s, 1H), 8.87 (s, 1H), 8.15 (d, J=8.5 Hz, 2H), 7.95 (s, 1H), 7.55 (d, J=8.5 Hz, 2H), 7.50 (d, J=8.7 Hz, 2H), 7.34 (d, J=8.7 Hz, 2H), 7.13 (s, 1H), 4.06 (t, J=4.5 Hz, 4H), 3.94 (s, 2H), 3.79 (t, J=4.5 Hz, 4H), 2.43 (s, 6H). ESI-MS: 506 (M+1), 508 (M+2+1).

1-(3-chlorophenyl)-3-(4-(6-((dimethylamino)methyl)-4-morpholinopyrrolo[2,1-f][1,2,4]triazin-2-yl)phenyl)urea (I-6)

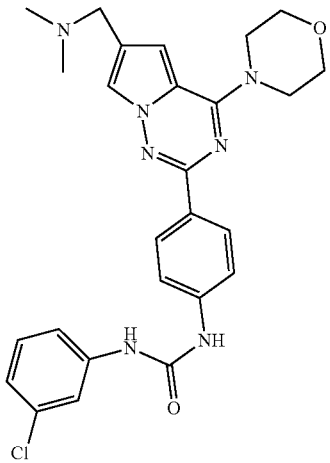 [SMILES: CN(C)Cc1cc2c(N3CCOCC3)nc(-c3ccc(NC(=O)Nc4cccc(Cl)c4)cc3)nn2c1]

The preparation process was identical with the preparation of I-1, except that ethyl isocyanate was replaced by m-chlorophenyl isocyanate. White solid (25 mg, 33.0%). m.p. 173-176° C. ¹H NMR (300 MHz, DMSO-d₆): δ 9.00 (s, 1H), 8.94 (s, 1H), 8.16 (d, J=8.8 Hz, 2H), 7.95 (d, J=1.3 Hz, 1H), 7.73 (t, J=1.9 Hz, 1H), 7.56 (d, J=8.8 Hz, 2H), 7.34-7.25 (m, 2H), 7.13 (d, J=1.3 Hz, 1H), 7.03 (dt, J=1.9, 7.0 Hz, 1H), 4.07 (t, J=4.6 Hz, 4H), 3.94 (s, 2H), 3.79 (t, J=4.6 Hz, 4H), 2.43 (s, 6H). ESI-MS: 506 (M+1), 508 (M+2+1).

1-(2,4-dichlorophenyl)-3-(4-(6-((dimethylamino)methyl)-4-morpholinopyrrolo[2,1-f][1,2,4]triazin-2-yl)phenyl)urea (I-7)

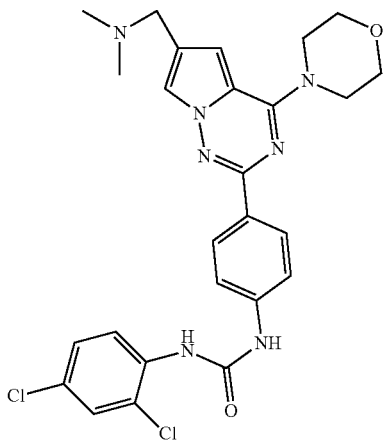 [SMILES: CN(C)Cc1cc2c(N3CCOCC3)nc(-c3ccc(NC(=O)Nc4ccc(Cl)cc4Cl)cc3)nn2c1]

The preparation process was identical with the preparation of I-1, except that ethyl isocyanate was replaced by 2,4-dichlorophenyl isocyanate. White solid (29 mg, 35.8%). m.p. 225° C. (decomposition). ¹H NMR (300 MHz, DMSO-d₆): δ 9.66 (s, 1H), 8.45 (s, 1H), 8.22 (d, J=9.0 Hz, 1H), 8.18 (d, J=8.8 Hz, 2H), 7.95 (d, J=1.4 Hz, 1H), 7.64 (d, J=2.4 Hz, 1H), 7.57 (d, J=8.8 Hz, 2H), 7.40 (dd, J=2.4, 9.0 Hz, 1H), 7.13 (d, J=1.4 Hz, 1H), 4.07 (t, J=4.7 Hz, 4H), 3.95 (s, 2H), 3.79 (t, J=4.7 Hz, 4H), 2.43 (s, 6H). ESI-MS: 540 (M+1), 542 (M+2+1).

1-(4-(6-((dimethylamino)methyl)-4-morpholinopyrrolo[2,1-f][1,2,4]triazin-2-yl)phenyl) 3-(3-(trifluoromethyl)phenyl)urea (I-8)

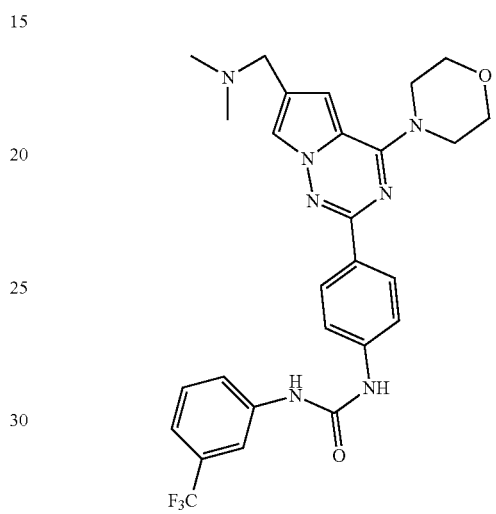

The preparation process was identical with the preparation of I-1, except that ethyl isocyanate was replaced by m-trifluorophenyl isocyanate. White solid (81 mg, 100%). m.p. 160-163° C. ¹H NMR (300 MHz, DMSO-d₆): δ 9.73 (s, 1H), 9.55 (s, 1H), 8.16 (d, J=8.8 Hz, 2H), 8.01 (s, 1H), 7.96 (d, J=1.1 Hz, 1H), 7.61 (d, J=8.6 Hz, 1H), 7.57 (d, J=8.8 Hz, 2H), 7.52 (t, J=7.5, 8.6 Hz, 1H), 7.31 (d, J=7.5 Hz, 1H), 7.12 (d, J=1.1 Hz, 1H), 4.07 (t, J=4.4 Hz, 4H), 3.94 (s, 2H), 3.79 (t, J=4.4 Hz, 4H), 2.43 (s, 6H). ESI-MS: 540 (M+1).

1-(4-(6-((dimethylamino)methyl)-4-morpholinopyrrolo[2,1-f][1,2,4]triazin-2-yl)phenyl)-3-(p-tolyl)urea (I-9)

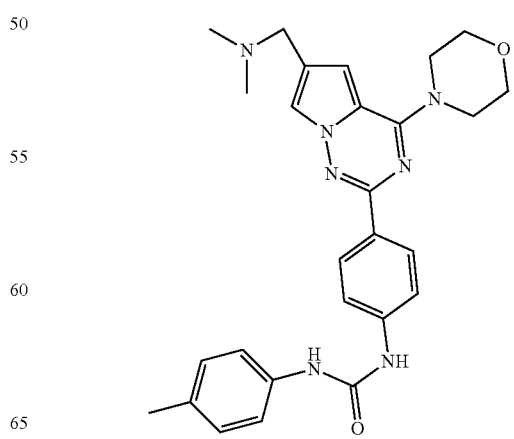

The preparation process was identical with the preparation of I-1, except that ethyl isocyanate was replaced by p-tolyl isocyanate. White solid (37 mg, 50.8%). m.p. 230° C. (decomposition). ¹H NMR (300 MHz, DMSO-d₆): δ 8.86 (s, 1H), 8.61 (s, 1H), 8.15 (d, J=8.8 Hz, 2H), 7.95 (d, J=1.2 Hz, 1H), 7.55 (d, J=8.8 Hz, 2H), 7.35 (d, J=8.6 Hz, 2H), 7.13 (d, J=1.2 Hz, 1H), 7.09 (d, J=8.6 Hz, 2H), 4.06 (t, J=4.6 Hz, 4H), 3.94 (s, 2H), 3.79 (t, J=4.6 Hz, 4H), 2.43 (s, 6H), 2.24 (s, 3H). ESI-MS: 486 (M+1).

1-(4-(6-((dimethylamino)methyl)-4-morpholinopyrrolo[2,1-f][1,2,4]triazin-2-yl)phenyl)-3-(4-methoxyphenyl)urea (I-10)

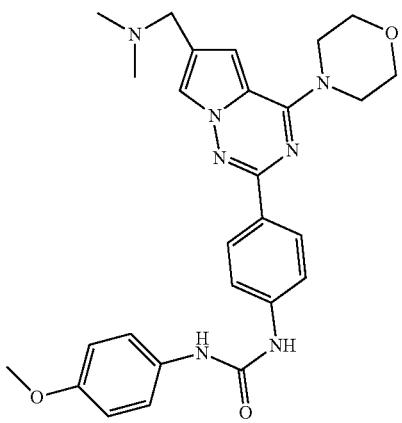 [SMILES: COc1ccc(NC(=O)Nc2ccc(-c3nc(N4CCOCC4)c4cc(CN(C)C)cn4n3)cc2)cc1]

The preparation process was identical with the preparation of I-1, except that ethyl isocyanate was replaced by p-methoxylphenyl isocyanate. White solid (49 mg, 65.2%). m.p. 235° C. (decomposition). ¹H NMR (300 MHz, DMSO-d₆): δ 8.82 (s, 1H), 8.52 (s, 1H), 8.14 (d, J=8.8 Hz, 2H), 7.94 (s, 1H), 7.55 (d, J=8.8 Hz, 2H), 7.37 (d, J=8.8 Hz, 2H), 7.12 (s, 1H), 6.87 (d, J=8.8 Hz, 2H), 4.06 (t, J=4.5 Hz, 4H), 3.95 (s, 2H), 3.79 (t, J=4.5 Hz, 4H), 3.72 (s, 3H), 2.43 (s, 6H). ESI-MS: 502 (M+1).

1-(4-(6-((dimethylamino)methyl)-4-morpholinopyrrolo[2,1-f][1,2,4]triazin-2-yl)phenyl)-3-(4-fluorobenzyl)urea (I-11)

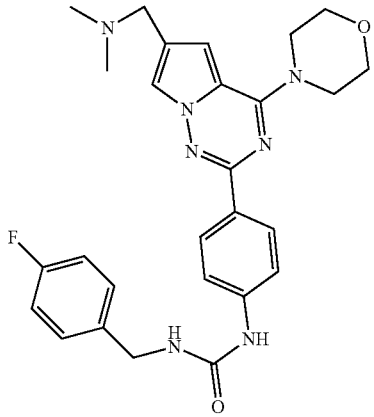 [SMILES: CN(C)Cc1cc2c(N3CCOCC3)nc(-c3ccc(NC(=O)NCc4ccc(F)cc4)cc3)nn2c1]

The preparation process was identical with the preparation of I-1, except that ethyl isocyanate was replaced by p-fluorobenzyl isocyanate. White solid (32 mg, 42.4%). m.p. 219-223° C. ¹H NMR (300 MHz, DMSO-d₆): δ 8.83 (s, 1H), 8.10 (d, J=8.8 Hz, 2H), 7.93 (s, 1H), 7.50 (d, J=8.8 Hz, 2H), 7.35 (dd, J=5.7, 8.6 Hz, 2H), 7.16 (t, J=8.6 Hz, 2H), 6.70 (t, J=5.5 Hz, 1H), 7.11 (s, 1H), 4.29 (d, J=5.5 Hz, 2H), 4.05 (t, J=4.4 Hz, 4H), 3.94 (s, 2H), 3.78 (t, J=4.4 Hz, 4H), 2.42 (s, 6H). ESI-MS: 504 (M+1).

1-(4-(6-((dimethylamino)methyl)-4-morpholinopyrrolo[2,1-f][1,2,4]triazin-2-yl)phenyl)-3-(3,5-dimethylisoxazol-4-yl)urea (I-12)

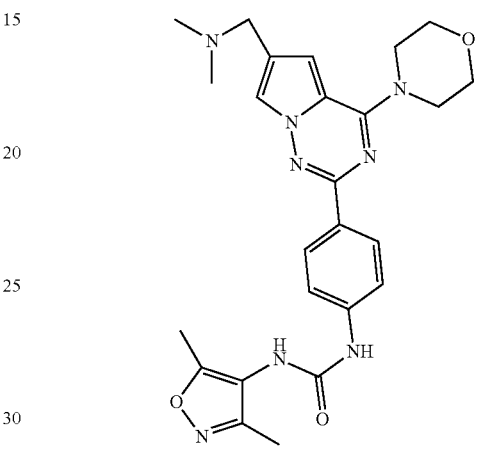

The preparation process was identical with the preparation of I-1, except that ethyl isocyanate was replaced by 3,5-dimethylisoxazoly-4-isocyanate. White solid (24 mg, 31.7%). m.p. 236° C. (decomposition). ¹H NMR (300 MHz, DMSO-d₆): δ 9.05 (s, 1H), 8.14 (d, J=8.8 Hz, 2H), 7.94 (d, J=1.6 Hz, 1H), 7.76 (s, 1H), 7.55 (d, J=8.8 Hz, 2H), 7.12 (d, J=1.6 Hz, 1H), 4.06 (t, J=4.5 Hz, 4H), 3.94 (s, 2H), 3.79 (t, J=4.5 Hz, 4H), 2.43 (s, 6H), 2.30 (s, 3H), 2.13 (s, 3H). ESI-MS: 505 (M+1).

Ethyl 4-(3-(4-(6-((dimethylamino)methyl)-4-morpholinopyrrolo[2,1-f][1,2,4]triazin-2-yl)phenyl)-ureido)benzoate (I-13)

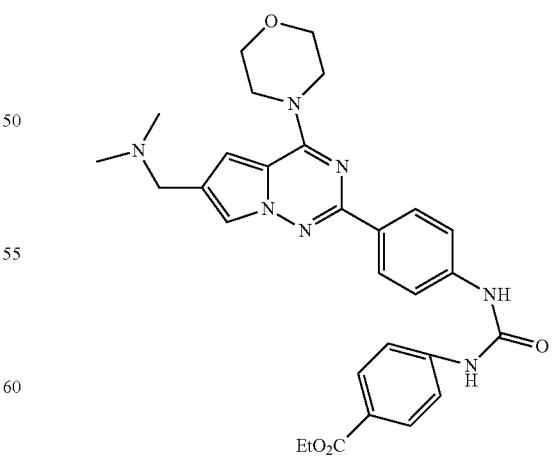

The preparation process was identical with the preparation of I-1, except that ethyl isocyanate was replaced by p-ethoxycarbonylphenyl isocyanate. White solid (47 mg, 57.7%). m.p. 175-176° C.

¹H NMR (300 MHz, DMSO-d₆): δ 8.24 (d, J=8.5 Hz, 2H), 8.01 (d, J=8.7 Hz, 2H), 7.68 (s, 1H), 7.49 (d, J=8.5 Hz, 2H), 7.42 (d, J=8.7 Hz, 2H), 6.92 (s, 1H), 6.78 (s, 1H), 6.70 (s, 1H), 4.36 (q, J=7.0 Hz, 2H), 4.10 (t, J=4.5 Hz, 4H), 4.03 (s, 2H), 3.89 (t, J=4.5 Hz, 4H), 2.58 (s, 6H), 1.39 (t, J=7.0 Hz, 3H). ESI-MS: 544 (M+1).

1-Ethyl-3-(4-(6-((4-(methylsulfonyl)piperazin-1-yl)methyl)-4-morpholinopyrrolo[2,1-f][1,2,4]triazin-2-yl)phenyl)urea (I-17)

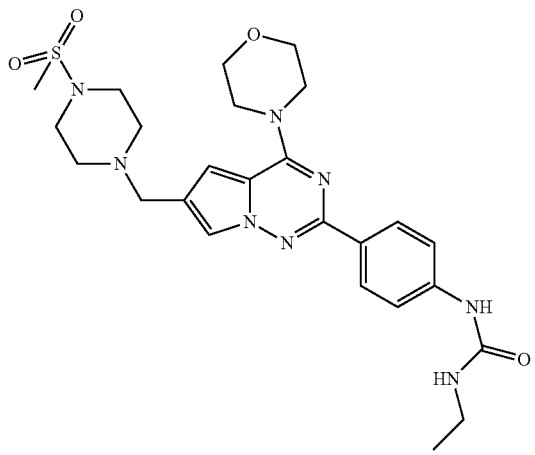 [SMILES: CCNC(=O)Nc1ccc(-c2nc(N3CCOCC3)c3cc(CN4CCN(S(C)(=O)=O)CC4)cn3n2)cc1]

The preparation process was identical with the preparation of I-1, except that 13a was replaced by compound 13b. White solid (34 mg, 41.8%). m.p. 200° C. (decomposition). ¹H NMR (300 MHz, DMSO-d₆): δ 8.92 (s, 1H), 8.08 (d, J=8.8 Hz, 2H), 7.92 (s, 1H), 7.49 (d, J=8.8 Hz, 2H), 7.09 (s, 1H), 6.36 (t, J=5.6 Hz, 1H), 4.10 (s, 2H), 4.05 (t, J=4.5 Hz, 4H), 3.79 (t, J=4.5 Hz, 4H), 3.49-3.37 (m, 4H), 3.11 (quint, J=5.6, 7.0 Hz, 2H), 2.96 (s, 3H), 2.89 (br, s, 4H), 1.05 (t, J=7.0 Hz, 3H). ESI-MS: 543 (M+1)

1-(4-fluorophenyl)-3-(4-(6-((4-(methylsulfonyl)piperazin-1-yl)methyl)-4-morpholinopyrrolo[2,1-f][1,2,4]triazin-2-yl)phenyl)urea (I-18)

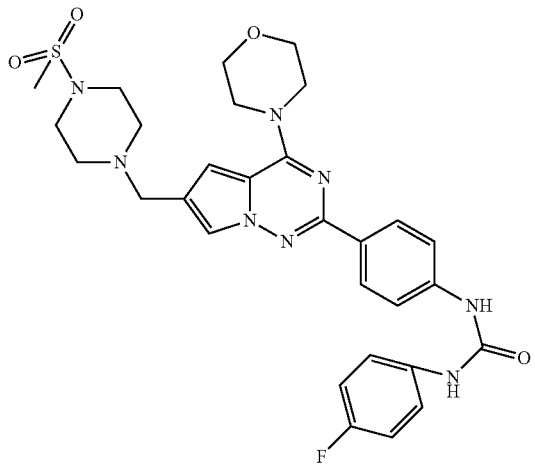 [SMILES: CS(=O)(=O)N1CCN(Cc2cc3c(N4CCOCC4)nc(-c4ccc(NC(=O)Nc5ccc(F)cc5)cc4)nn3c2)CC1]

The preparation process was identical with the preparation of I-4, except that 13a was replaced by compound 13b. White solid (45 mg, 49.3%). m.p. 255-256° C. ¹H NMR (300 MHz, DMSO-d₆): δ 8.89 (s, 1H), 8.74 (s, 1H), 8.15 (d, J=8.8 Hz, 2H), 7.93 (s, 1H), 7.56 (d, J=8.8 Hz, 2H), 7.47 (dd, J=4.8, 8.8 Hz, 2H), 7.13 (t, J=8.8 Hz, 2H), 6.50 (s, 1H), 4.10 (s, 2H), 4.07 (br, s, 4H), 3.80 (br, s, 4H), 3.58-3.38 (m, 4H), 2.96 (s, 3H), 2.90 (br, s, 4H). ESI-MS: 609 (M+1).

1-(4-(4-(8-oxa-3-azabicyclo[3.2.1]octan-3-yl)-6-((4-(methylsulfonyl)piperazin-1-yl)methyl)-pyrrolo[2,1-f][1,2,4]triazin-2-yl)phenyl)-3-(4-fluorophenyl)urea (I-19)

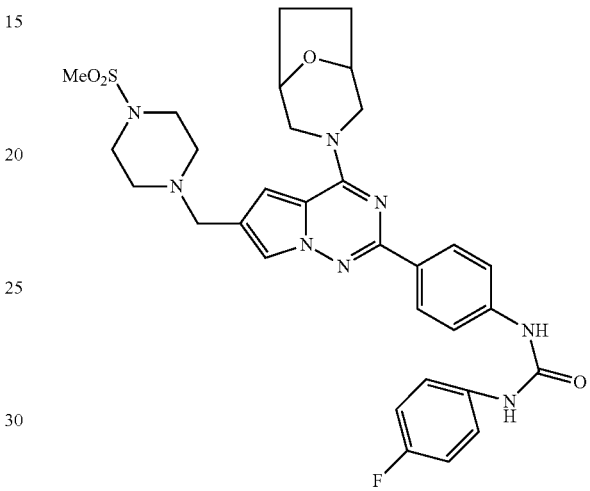

The preparation process was identical with the preparation of I-4, except that 13a was replaced by compound 13c. White solid (31 mg, 32.6%). m.p. 266-267° C. ¹H NMR (300 MHz, DMSO-d₆): δ 8.89 (s, 1H), 8.75 (s, 1H), 8.13 (d, J=8.5 Hz, 2H), 7.70 (s, 1H), 7.54 (d, J=8.5 Hz, 2H), 7.47 (dd, J=5.0, 8.8 Hz, 2H), 7.13 (t, J=8.8 Hz, 2H), 6.84 (s, 1H), 4.51 (br, s, 4H), 3.57 (s, 2H), 3.47 (br s, 1H), 3.43 (br s, 1H), 3.32 (br s, 4H), 3.11 (t, J=4.0 Hz, 4H), 2.87 (s, 3H), 1.89-1.85 (m, 2H), 1.80-1.76 (m, 2H). ESI-MS: 635 (M+1).

Ethyl 4-(-3-(4-(6-((4-(methylsulfonyl)piperazin-1-yl)methyl)-4-morpholinopyrrolo[2,1-f][1,2,4]triazin-2-yl)phenyl)ureido)benzoate (I-20)

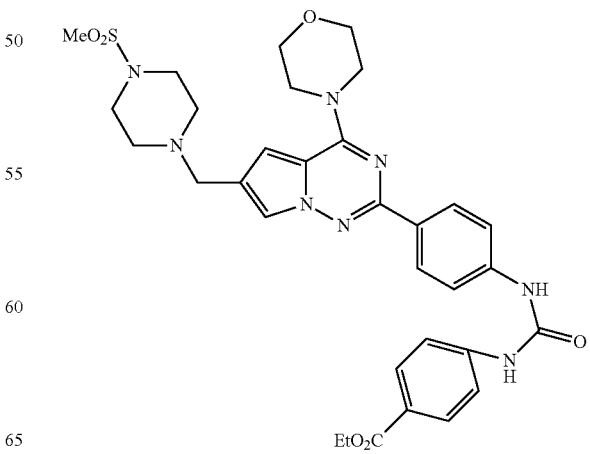

The preparation process was identical with the preparation of I-13, except that 13a was replaced by compound 13b. White solid (40 mg, 40.2%). m.p. 260-262° C. $^1$H NMR (300 MHz, DMSO-d$_6$): δ 9.15 (s, 1H), 9.02 (s, 1H), 8.16 (d, J=8.8 Hz, 2H), 7.90 (d, J=8.8 Hz, 2H), 7.72 (s, 1H), 7.62-7.56 (m, 4H), 6.90 (s, 1H), 6.52 (s, 3H), 4.28 (q, J=7.0 Hz, 2H), 4.05 (br s, 4H), 3.79 (br s, 4H), 3.58 (s, 2H), 3.11 (br s, 4H), 2.87 (br s, 4H), 1.31 (t, J=7.0 Hz, 3H). ESI-MS: 663 (M+1).

13. General Preparation Method for Compounds I-14~I-16

The corresponding carboxylic acid (0.5 mmol) was dissolved in anhydrous N,N-dimethylformamide and triethylamine (101 mg, 1 mmol), and diphenyl azidophosphate (165 mg, 0.6 mmol) was added and reacted at room temperature for 1 hour. The reaction mixture was poured into water and filtered, and the filter cake was dried in a vacuum oven at room temperature for 24 hours to give p-carbamoylbenzoyl azide. Compound 13 (0.1 mmol) and p-carbamoylbenzoyl azide (0.2 mmol) in anhydrous dioxane were refluxed for 3 hours. The solvent was distilled off under reduced pressure. The residue was dissolved in a mixed solvent of dichloromethane and methanol and purified by preparative thin layer chromatography (dichloromethane:methanol=8:1), so as to give a pure desired product.

4-(3-(4-(6-((dimethylamino)methyl)-4-morpholinopyrrolo[2,1-f][1,2,4]triazin-2-yl)phenyl)ureido)-N,N-dimethylbenzamide (I-14)

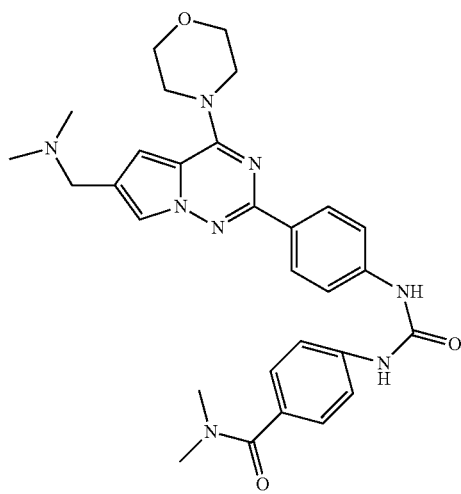 [SMILES: CN(C)Cc1cc2c(N3CCOCC3)nc(-c3ccc(NC(=O)Nc4ccc(C(=O)N(C)C)cc4)cc3)nn2c1]

According to the general method described in example 13, 4-(dimethylcarbamoyl)benzoic acid was used as starting material, and the resulting 4-(dimethylcarbamoyl)benzoyl azide reacted with 13a to give a light yellow solid (14 mg, 25.8%). m.p. 240° C. $^1$H NMR (300 MHz, DMSO-d$_6$): δ 9.59 (s, 2H), 8.16 (d, J=8.5 Hz, 2H), 7.99 (s, 1H), 7.58 (d, J=8.5 Hz, 2H), 7.52 (d, J=8.5 Hz, 2H), 7.36 (d, J=8.5 Hz, 2H), 7.19 (s, 1H), 4.25 (s, 2H), 4.08 (t, J=4.4 Hz, 4H), 3.80 (t, J=4.4 Hz, 4H), 2.96 (s, 6H), 2.69 (s, 6H). ESI-MS: 543 (M+1).

1-(4-(6-((dimethylamino)methyl)-4-morpholinopyrrolo[2,1-f][1,2,4]triazin-2-yl)phenyl)-3-(4-(4-methylpiperazine-1-carbonyl)phenyl)urea (I-15)

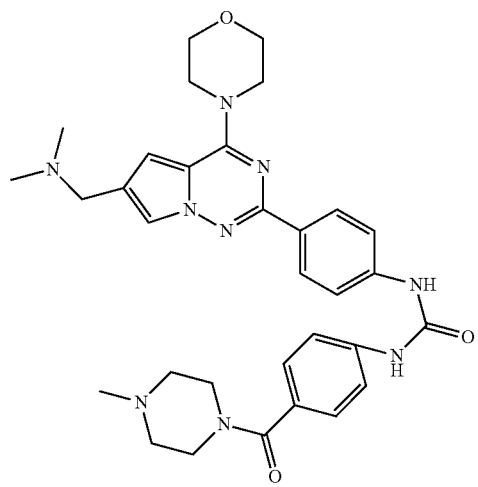 [SMILES: CN(C)Cc1cc2c(N3CCOCC3)nc(-c3ccc(NC(=O)Nc4ccc(C(=O)N5CCN(C)CC5)cc4)cc3)nn2c1]

According to the general methods described in example 13, 4-(4-methylpiperazine-1-carbonyl)benzoic acid was used as starting material, and the resulting 4-(4-methylpiperazine-1-carbonyl)benzoyl azide reacted with 13a to give a white solid (9 mg, 15.1%). $^1$H NMR (300 MHz, DMSO-d$_6$): δ 9.63 (br, s, 2H), 8.16 (d, J=8.9 Hz, 2H), 7.92 (s, 1H), 7.57 (d, J=8.9 Hz, 2H), 7.53 (d, J=8.5 Hz, 2H), 7.34 (d, J=8.5 Hz, 2H), 7.13 (s, 1H), 4.07 (br, s, 6H), 3.80 (br, s, 4H), 3.51 (br, s, 4H), 3.06 (br s, 2H), 2.55 (s, 6H), 2.38 (br s, 2H), 2.24 (s, 3H). ESI-MS: 598 (M+1).

1-(4-(6-((dimethylamino)methyl)-4-morpholinopyrrolo[2,1-f][1,2,4]triazin-2-yl)phenyl)-3-(4-(piperidine-1-carbonyl)phenyl)urea (I-16)

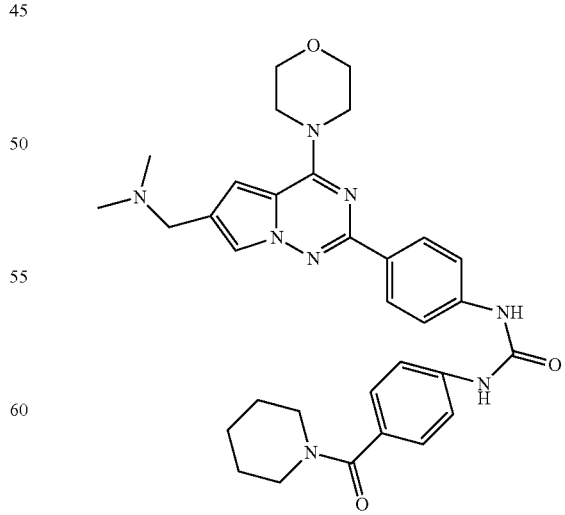

According to the general method described in example 13, 4-(piperidine-1-carbonyl)benzoic acid was used as starting material, and the resulting 4-(piperidine-1-carbonyl)benzoyl azide reacted with 13a to give a yellow solid (11 mg, 18.9%). m.p. 184-186° C. $^1$H NMR (300 MHz, DMSO-d$_6$): δ 9.57 (s, 2H), 8.15 (d, J=8.8 Hz, 2H), 7.93 (s, 1H), 7.57 (d, J=8.8 Hz, 2H), 7.52 (d, J=8.6 Hz, 2H), 7.31 (d, J=8.6 Hz, 2H), 7.13 (s, 1H), 4.07 (br, s, 6H), 3.79 (t, J=4.3 Hz, 4H), 3.38 (br, s, 4H), 2.58 (s, 6H), 1.60 (br, s, 2H), 1.50 (br, s, 4H). ESI-MS: 583 (M+1).

14. Preparation of 4-(3-(-4(6-((4-(methylsulfonyl)piperazin-1-yl)methyl)-4-morpholino pyrrolo [2,1-f][1,2,4]triazin-2-yl)phenyl)ureido)benzoic acid (14)

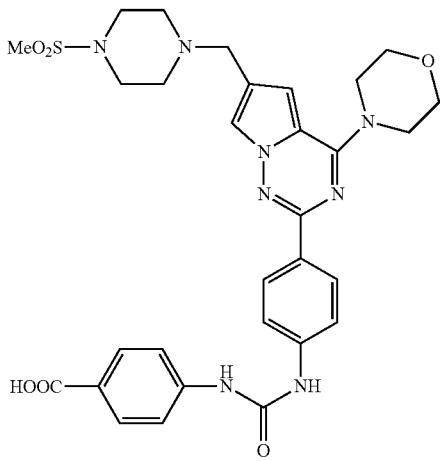 [SMILES: CS(=O)(=O)N1CCN(Cc2cc3c(N4CCOCC4)nc(-c4ccc(NC(=O)Nc5ccc(C(=O)O)cc5)cc4)nn3c2)CC1]

Compound I-20 (395 mg, 0.6 mmol) was suspended in 20 mL of tetrahydrofuran and 10 mL of methanol, and 4 mL of 1 M potassium hydroxide solution was added and refluxed for 3 hours. The reaction mixture was cooled and 2 mL of acetic acid was added to precipitate solids. After filtered, white solids (312 mg, 82.0%) were obtained. m.p. 207-209° C. $^1$H NMR (300 MHz, DMSO-d$_6$): δ 9.16 (s, 1H), 9.08 (s, 1H), 8.16 (d, J=8.7 Hz, 2H), 7.88 (d, J=8.7 Hz, 2H), 7.71 (s, 1H), 7.58 (d, J=7.9 Hz, 4H), 6.87 (s, 1H), 4.04 (br s, 4H), 3.79 (br s, 4H), 3.58 (s, 2H), 3.34 (br, s, 4H), 3.11 (br s, 4H), 2.87 (s, 3H). LC-MS: 635 (M+1).

15. General Preparation Methods for Compound I-21~I-23

Compound 14 (95 mg, 0.15 mmol), diisopropylethylamine (116 mg, 0.9 mmol), and HBTU (benzotriazol-N,N,N',N'-tetramethyluronium hexafluorophosphate, 284 mg, 0.75 mmol) were dissolved in 5 mL of N,N-dimethylformamide and stirred for 1 hour at room temperature. Each corresponding amine (0.6 mmol) was added and stirred at room temperature for 4-6 hours. The reaction mixture was poured into 50 mL of water and extracted with ethyl acetate. The resulting mixture was separated by a preparative plate (dichloromethane:methanol=10:1) to give a product.

N,N-dimethyl-4-(3-(4-(6-((4-(methylsulfonyl)piperazin-1-yl)methyl)-4-morpholinopyrrolo[2,1-f][1,2,4]triazin-2-yl)phenyl)ureido)benzamide (I-21)

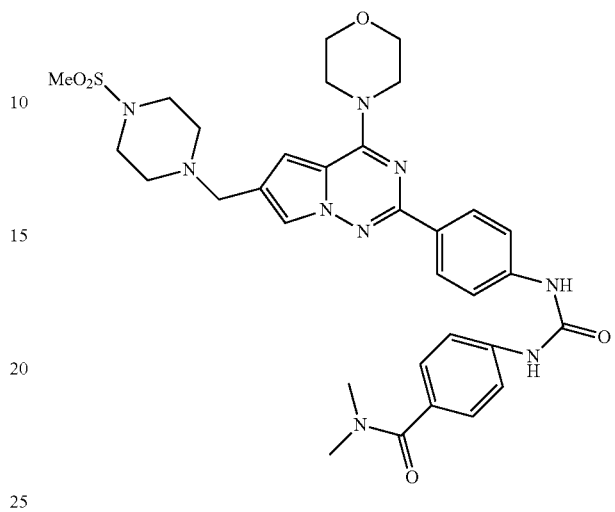

Light yellow solid (38 mg, 38.3%). m.p. 248-250° C. $^1$H NMR (300 MHz, DMSO-d$_6$): δ 9.40 (s, 2H), 8.15 (d, J=8.8 Hz, 2H), 7.72 (s, 1H), 7.57 (d, J=8.9 Hz, 2H), 7.52 (d, J=8.9 Hz, 2H), 7.36 (d, J=8.8 Hz, 2H), 6.89 (s, 1H), 4.05 (t, J=4.4 Hz, 4H), 3.79 (t, J=4.4 Hz, 4H), 3.59 (s, 2H), 3.32 (br s, 4H), 3.12 (br s, 4H), 2.96 (s, 6H), 2.87 (s, 3H). ESI-MS: 684 (M+23).

1-(4-(4-methylpiperazine-carbonyl)phenyl)-3-(4-(6-((4-(methylsulfonyl)piperazin-1-yl)methy 1)-4-morpholinopyrrolo[2,1-f][1,2,4]triazin-2-yl)phenyl)urea (I-22)

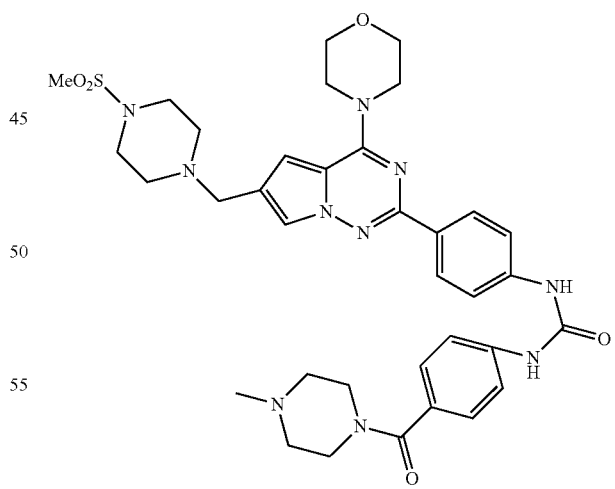

Light yellow solid (40 mg, 37.2%). m.p. 185-188° C. $^1$H NMR (300 MHz, DMSO-d$_6$): δ 9.03 (s, 1H), 9.02 (s, 1H), 8.15 (d, J=8.7 Hz, 2H), 7.71 (s, 1H), 7.58-7.52 (m, 4H), 7.34 (d, J=8.7 Hz, 2H), 6.89 (s, 1H), 4.04 (t, J=4.7 Hz, 4H), 3.79 (t, J=4.7 Hz, 4H), 3.59 (s, 2H), 3.50 (br s, 4H), 3.32 (br s, 4H), 3.12 (br s, 4H), 2.87 (s, 3H), 2.38 (br s, 4H), 2.24 (s, 3H). ESI-MS: 717 (M+1).

1-(4-(4-(dimethylamino)piperidine-1-carbonyl)phenyl)-3-(4-(6-((4-(methylsulfonyl)piperazin-1-yl)methyl)-4-morpholinopyrrolo [2,1-f][1,2,4]triazin-2-yl)phenyl)urea (I-23)

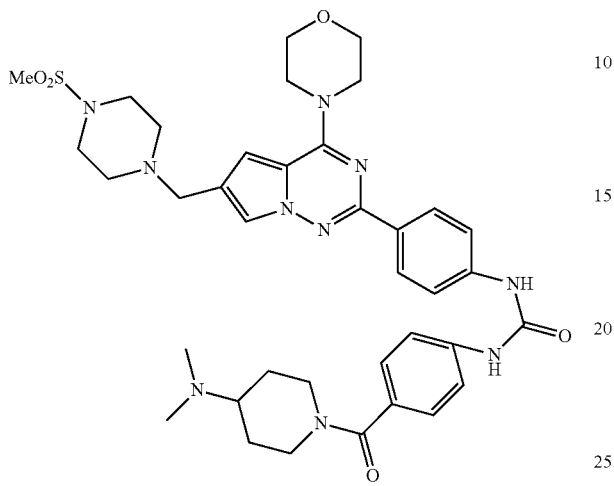

White solid (44 mg, 39.4%). m.p. 200-202° C. $^1$H NMR (300 MHz, DMSO): δ 9.12 (s, 2H), 8.15 (d, J=8.6 Hz, 2H), 7.71 (s, 1H), 7.58-7.53 (m, 4H), 7.37 (d, J=8.6 Hz, 2H), 6.90 (s, 1H), 4.05 (t, J=4.2 Hz, 4H), 3.79 (t, J=4.2 Hz, 4H), 3.59 (s, 2H), 3.32 (br s, 8H), 3.12 (br s, 4H), 2.87 (s, 3H), 2.94 (s, 1H), 2.68 (s, 6H), 2.05-1.91 (m, 2H), 1.63-1.48 (m, 2H). ESI-MS: 745 (M+1).

16. Preparation of methyl 2-(3-(acetoxymethyl)phenyl)-4-chloropyrrolo[2,1-f][1,2,4] triazine-6-carboxylate (15)

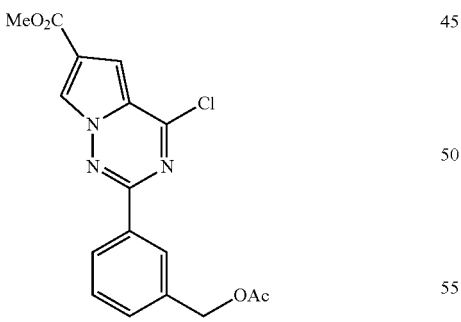

Compound 15 was prepared by the method which was identical with that for preparing compound 8, wherein compound IIIb (341 mg, 1 mmol) was used as the starting material. The crude product was purified by column chromatography (petroleum ether:ethyl acetate=5:1) to obtain white solid (197 mg, 54.8%). m.p. 154-155° C. $^1$H NMR (300 MHz, CDCl$_3$): δ 8.33-8.29 (m, 3H), 7.52-7.50 (m, 2H), 7.41 (d, J=1.3 Hz, 1H), 5.20 (s, 2H), 3.94 (s, 3H), 2.14 (s, 3H). LC-MS: 360 (M+1), 362 (M+2+1).

17. Preparation of methyl 2-(3-(acetoxymethyl)phenyl)-4-morpholinopyrrolo[2,1-f][1,2,4] triazine-6-carboxylate (16)

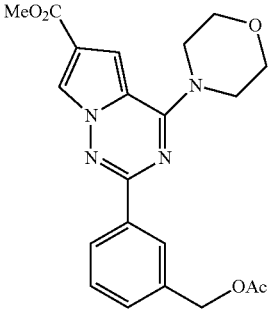 [SMILES: COC(=O)c1cc2c(N3CCOCC3)nc(-c3cccc(COC(C)=O)c3)nn2c1]

Compound 16 was prepared by the method which was identical with that for preparing compound 9, wherein compound 15 (180 mg, 0.5 mmol) was used as the starting material. White solid (177 mg, 86.3%). m.p. 204-205° C. $^1$H NMR (300 MHz, CDCl$_3$): δ 8.26-8.22 (m, 2H), 8.13 (s, 1H), 7.46 (d, J=4.5 Hz, 2H), 7.19 (s, 1H), 5.19 (s, 2H), 4.15 (t, J=4.8 Hz, 4H), 3.90 (s, 3H), 3.90 (t, J=4.8 Hz, 4H), 2.13 (s, 3H). LC-MS: 411 (M+1).

18. Preparation of 2-(3-(hydroxymethyl)phenyl)-4-morpholinopyrrolo[2,1-f][1,2,4] triazine-6-carboxylic acid (17)

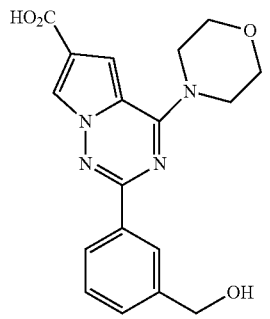 [SMILES: O=C(O)c1cc2c(N3CCOCC3)nc(-c3cccc(CO)c3)nn2c1]

Compound 17 was prepared by the method which was identical with that for preparing compound 11, wherein compound 16 (150 mg, 0.366 mmol) was used as the starting material. White solid (111 mg, 85.7%). m.p. 254° C. (decomposition). $^1$H NMR (300 MHz, DMSO-d$_6$): δ 12.64 (s, 1H), 8.21 (s, 1H), 8.19 (d, J=1.6 Hz, 1H), 8.13-8.10 (m, 1H), 7.44-7.42 (m, 2H), 7.36 (d, J=1.6 Hz, 1H), 5.30 (s, 1H), 4.58 (s, 2H), 4.10 (t, J=4.5 Hz, 4H), 3.80 (t, J=4.5 Hz, 4H). LC-MS: 355 (M+1).

19. Preparation of 2-(3-(hydroxymethyl)phenyl)-N,N-dimethyl-4-morpholinopyrrolo [2,1-f][1,2,4]triazine-6-carboxamide (18)

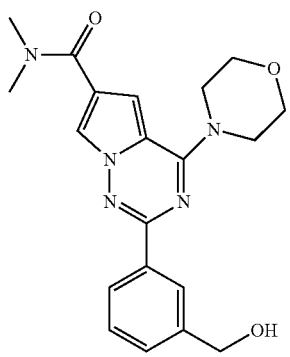 [SMILES: CN(C)C(=O)c1cc2c(N3CCOCC3)nc(-c3cccc(CO)c3)nn2c1]

Compound 18 was prepared by the method which was identical with that for preparing compound 12a, wherein compound 17 (92 mg, 0.26 mmol) was used as the starting material. White solid (80 mg, 80.8%). m.p. 170-171° C. $^1$H NMR (300 MHz, CDCl$_3$): δ 8.22 (s, 1H), 8.20-8.17 (m, 1H), 7.84 (d, J=1.5 Hz, 1H), 7.46-7.43 (m, 2H), 7.04 (d, J=1.5 Hz, 1H), 4.77 (s, 2H), 4.11 (t, J=4.7 Hz, 4H), 3.87 (t, J=4.7 Hz, 4H), 3.20 (br, s, 6H). LC-MS: 382 (M+1).

20. Preparation of (3-(6-((dimethylamino)methyl)-4-morpholinopyrrolo[2,1-f][1,2,4] triazin-2-yl)phenyl)methanol (I-24)

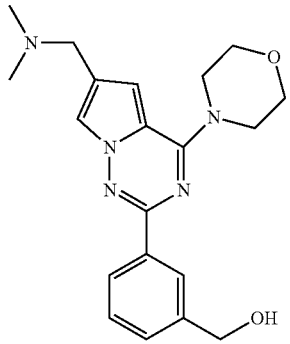 [SMILES: CN(C)Cc1cc2c(N3CCOCC3)nc(-c3cccc(CO)c3)nn2c1]

Compound I-24 was prepared by the method which was identical with that for preparing compound 13a, wherein compound 18 (70 mg, 0.184 mmol) was used as the starting material. White solid (100%). m.p. 163-165° C. $^1$H NMR (300 MHz, DMSO-d$_6$): δ 8.20 (s, 1H), 8.11 (dt, J=2.4, 6.0 Hz, 1H), 7.99 (d, J=1.3 Hz, 1H), 7.45-7.41 (m, 2H), 7.15 (d, J=1.3 Hz, 1H), 5.27 (t, J=5.8 Hz, 1H), 4.57 (d, J=5.8 Hz, 2H), 4.07 (t, J=4.6 Hz, 4H), 3.95 (s, 2H), 3.80 (t, J=4.6 Hz, 4H), 2.44 (s, 6H). MS (EI) m/e (%): 367 (M$^+$, 16).

21. Preparation of 3-(6-((dimethylamino)methyl)-4-morpholinopyrrolo[2,1-f][1,2,4] triazin-2-yl)benzyl methanesulfonate (19)

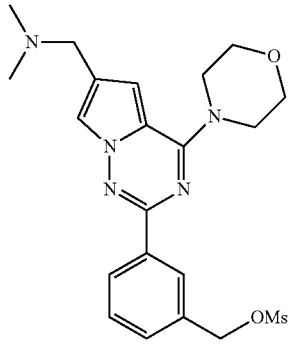 [SMILES: CN(C)Cc1cc2c(N3CCOCC3)nc(-c3cccc(COS(C)(=O)=O)c3)nn2c1]

Compound I-24 (36.7 mg, 0.1 mmol) was dissolved in 5 mL of anhydrous dichloromethane and cooled to 0° C. Methanesulfonyl chloride (14 μL, 0.12 mmol) and triethylamine (16 μL, 0.12 mmol) were added. The reaction was performed at 0° C. for 30 minutes. The reaction mixture was washed successively with saturated sodium bicarbonate solution and water, and the organic layer was dried over anhydrous sodium sulfate, and the solvent was removed under reduced pressure to give 45 mg of white solid (100%). m.p. 178-179° C. $^1$H NMR (300 MHz, CDCl$_3$): δ 8.33 (s, 1H), 8.31 (dd, J=1.8, 5.5 Hz, 1H), 7.70 (d, J=1.5 Hz, 1H), 7.51 (d, J=5.5 Hz, 2H), 6.72 (d, J=1.5 Hz, 1H), 5.34 (s, 2H), 4.14 (t, J=4.8 Hz, 4H), 4.04 (s, 2H), 3.91 (t, J=4.8 Hz, 4H), 2.95 (s, 3H), 2.56 (s, 6H). MS (EI) m/e (%): 350 (M-MeSO$_3$, 30).

22. Preparation of N,N-dimethyl-1-(2-(3-((methylsulfonyl)methyl)phenyl)-4-morpholino pyrrolo[2,1-f][1,2,4]triazin-6-yl)methanamine (I-25)

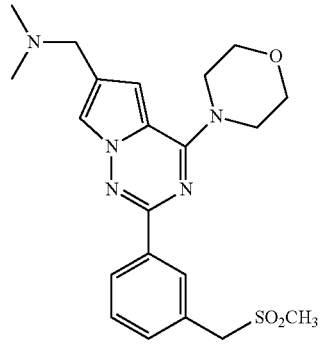 [SMILES: CN(C)Cc1cc2c(N3CCOCC3)nc(-c3cccc(CS(C)(=O)=O)c3)nn2c1]

Compound 19 (45 mg, 0.1 mmol) and sodium methylsulfinate (41 mg, 0.4 mmol) were dissolved in 2 mL N-methylpyrrolidone. The mixture was under microwave irradiation for 30 minutes at 120° C. with the power of 100 watts. After completion of the reaction, the reaction mixture was poured into water, extracted for three times with ethyl acetate, and extracted for three times with dichloromethane. The organic layers were combined and dried over anhydrous sodium sulfate. The solvent was concentrated under reduced pressure to a small volume. The crude product was purified by a preparative plate (dichloromethane:methanol=6:1) to obtain 12 mg of white solid (28.0%). m.p. 143-144° C., $^1$H NMR (300 MHz, CDCl$_3$): δ 8.32 (d, J=5.2 Hz, 1H), 8.29 (s, 1H), 7.63 (d, J=1.2 Hz, 1H), 7.50 (d, J=5.2 Hz, 2H), 6.78 (d, J=1.2 Hz, 1H), 4.34 (s, 2H), 4.11 (t, J=4.4 Hz, 4H), 3.88 (t, J=4.4 Hz, 4H), 3.66 (s, 2H), 2.78 (s, 3H), 2.36 (s, 6H). MS (EI) m/e (%): 429 (M$^+$, 12).

23. Preparation of 1-(2-(3-(aminomethyl)phenyl)-4-morpholinopyrrolo[2,1-f][1,2,4] triazin-6-yl)-N,N-dimethylmethanamine (20)

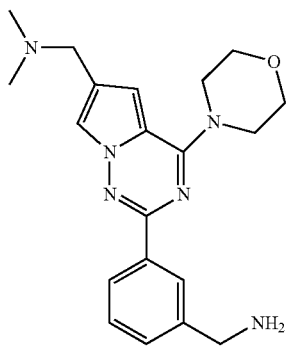 [SMILES: CN(C)Cc1cc2c(N3CCOCC3)nc(-c3cccc(CN)c3)nn2c1]

Compound 19 (80 mg, 0.18 mmol) was added to 20 mL of saturated ammonia solution of methanol. The reaction was carried out at 80° C. in a sealed tube for 8 h. After the reaction mixture was concentrated, it was purified by a preparative plate (dichloromethane:methanol=6:1) to obtain 37 mg of colourless oil (56.2%). $^1$H NMR (300 MHz, CDCl$_3$): δ 8.20 (s, 1H), 8.17-8.13 (m, 1H), 7.64 (s, 1H), 7.41-7.39 (m, 2H), 6.86 (s, 1H), 4.11 (t, J=4.7 Hz, 4H), 3.97 (s, 2H), 3.87 (t, J=4.7 Hz, 4H), 3.69 (s, 2H), 2.41 (s, 6H). LC-MS: 367 (M+1).

24. Preparation of N-(3-(6-((dimethylamino)methyl)-4-morpholinopyrrolo[2,1-f][1,2,4] triazin-2-yl)benzyl)methanesulfonamide (I-26)

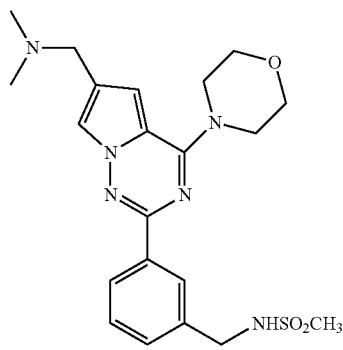

Compound I-26 was prepared by the method which was identical with that for preparing compound 19, wherein compound 20 (37 mg, 0.1 mmol) was used as the starting material. Light yellow solid (12 mg, 26.7%) were obtained by a preparative plate (dichloromethane:methanol=8:1). m.p. 238-240° C. $^1$H NMR (300 MHz, CDCl$_3$): δ 8.20 (s, 1H), 8.19 (d, J=7.1 Hz, 1H), 7.60 (s, 1H), 7.47-7.38 (m, 2H), 6.88 (s, 1H), 4.41 (s, 2H), 4.02 (br, s, 4H), 3.81 (t, J=4.4 Hz, 4H), 2.95 (s, 2H), 2.94 (s, 3H), 2.87 (s, 1H), 2.51 (s, 6H). MS (EI) m/e (%): 444 (M$^+$, 16).

25. Preparation of methyl 4-chloro-2-(6-pivalamido-4-(trifluoromethyl)pyridin-3-yl)pyrrolo [2,1-f][1,2,4]triazine-6-carboxylate (21)

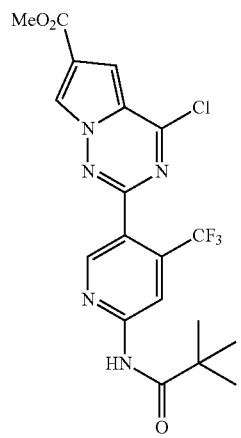 [SMILES: COC(=O)c1cc2c(Cl)nc(-c3cnc(NC(=O)C(C)(C)C)cc3C(F)(F)F)nn2c1]

Compound 21 was prepared by the method which was identical with that for preparing compound 8, wherein IIIc (300 mg, 0.686 mmol) was used as the starting material. Light yellow solid (290 mg, 92.9%). m.p. 172-173° C. $^1$H NMR (300 MHz, CDCl$_3$): δ 8.79 (s, 1H), 8.77 (s, 1H), 8.33 (d, J=1.6 Hz, 1H), 8.30 (s, 1H), 7.47 (d, J=1.6 Hz, 1H), 3.94 (s, 3H), 1.36 (s, 9H). LC-MS: 478 (M+23), 480 (M+2+23).

26. Preparation of Compounds 22

The preparation of compounds 22 was identical with that for compound 9.

Methyl 4-morpholino-2-(6-pivalamido-4-(trifluoromethyl)pyridin-3-yl)pyrrolo[2,1-f][1,2,4] triazine-6-carboxylate (22a)

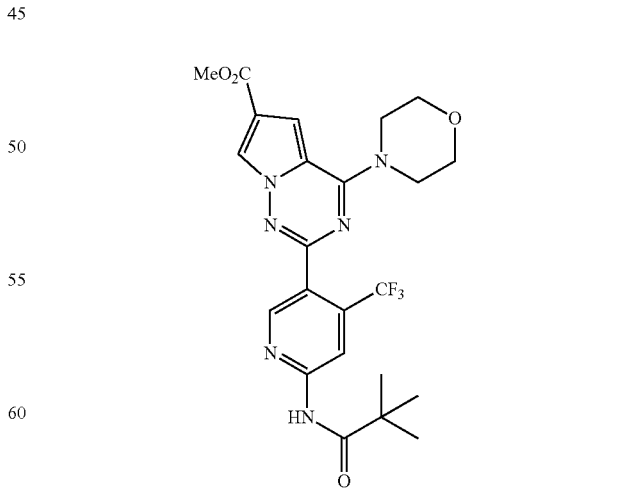

Compound 22a was prepared from 100 mg of compound 21 (0.22 mmol). White solid (73 mg, 65.8%). m.p. 205° C. $^1$H NMR (300 MHz, DMSO-d$_6$): δ 10.53 (s, 1H), 8.79 (s, 1H), 8.57 (s, 1H), 8.30 (d, J=1.2 Hz, 1H), 7.46 (d, J=1.2 Hz, 1H), 4.03 (t, J=4.2 Hz, 4H), 3.83 (s, 3H), 3.75 (t, J=4.2 Hz, 4H), 1.27 (s, 9H). LC-MS: 507 (M+1).

Methyl-4-(8-oxa-3-azabicyclo[3.2.1]octan-3-yl)-2-(6-pivalamido-4-(trifluoromethyl)pyridine yl)pyrrolo[2,1-f][1,2,4]triazine-6-carboxylate (22b)

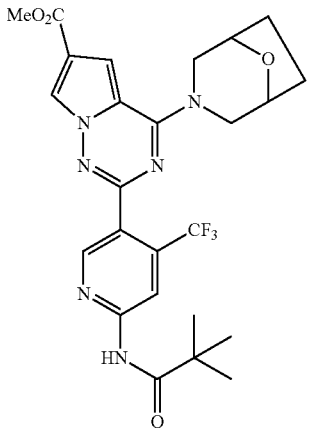 [SMILES: COC(=O)c1cc2c(N3CC4CCC(C3)O4)nc(-c3cnc(NC(=O)C(C)(C)C)cc3C(F)(F)F)nn2c1]

Compound 22b was prepared from 276 mg of compound 21 (0.61 mmol). Light yellow solid (274 mg, 84.8%). m.p. 175-176° C. ¹H NMR (300 MHz, CDCl₃): δ 8.71 (s, 1H), 8.70 (s, 1H), 8.27 (s, 1H), 8.09 (s, 1H), 7.21 (s, 1H), 4.52 (br s, 4H), 3.90 (s, 3H), 3.54 (br s, 2H), 2.04-1.99 (m, 2H), 1.89-1.78 (m, 2H), 1.36 (s, 9H). LC-MS: 533 (M+1).

(S)-methyl 4-(3-methylmorpholino)-2-(6-pivalamido-4-(trifluoromethyl)pyridin-3-yl) pyrrolo[2,1-f][1,2,4]triazine-6-carboxylate (22c)

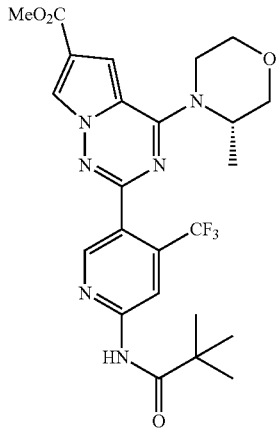 [SMILES: COC(=O)c1cc2c(N3CCOC[C@@H]3C)nc(-c3cnc(NC(=O)C(C)(C)C)cc3C(F)(F)F)nn2c1]

Compound 22c was prepared from 210 mg of compound 21 (0.46 mmol). Light yellow solid (145 mg, 60.4%). m.p. 225-226° C. ¹H NMR (300 MHz, DMSO-d₆): δ 10.53 (s, 1H), 8.79 (s, 1H), 8.57 (s, 1H), 8.29 (d, J=1.5 Hz, 1H), 7.42 (s, 1H), 4.92 (br, 1H), 4.61 (br, 1H), 4.03-3.96 (m, 1H), 3.83 (s, 3H), 3.81-3.64(m, 3H), 3.53 (t, J=11.4 Hz, 1H), 1.43-1.31 (m, 3H), 1.27 (s, 9H). LC-MS: 521 (M+1).

27. Preparation of Compounds 23

2-(6-amino-4-(trifluoromethyl)pyridin-3-yl)-4-morpholinopyrrolo[2,1-f][1,2,4]triazine-6-carboxylic acid (23a)

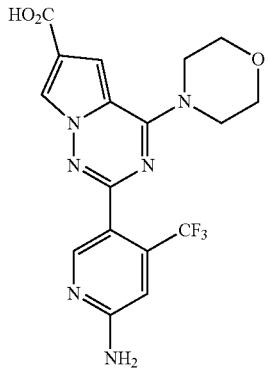 [SMILES: Nc1cc(C(F)(F)F)c(-c2nc(N3CCOCC3)c3cc(C(=O)O)cn3n2)cn1]

Compound 22a (300 mg, 0.59 mmol) was suspended in 10 mL of ethanol. 1.5 mL of 2 M potassium hydroxide solution was added and refluxed for 1 hour. The reaction is substantially completed. 2 mL of acetic acid was added. Most of the solvent was distilled off under reduced pressure to precipitate solids. The precipitated solids were filtered to give compound 23a. White solid (224 mg, 92.6%). m.p. 244-245° C. ¹H NMR (300 MHz, DMSO-d₆): δ 12.54 (s, 1H), 8.37 (s, 1H), 8.11 (s, 1H), 7.34 (s, 1H), 6.83 (s, 3H), 4.00 (t, J=4.0 Hz, 4H), 3.73 (t, J=4.0 Hz, 4H). LC-MS: 409 (M+1).

2-(6-amino-4-(trifluoromethyl)pyridin-3-yl)-4-(8-oxa-3-azabicyclo[3.2.1]octan-3-yl)pyrrolo[2,1-f][1,2,4]triazine-6-carboxylic acid (23b)

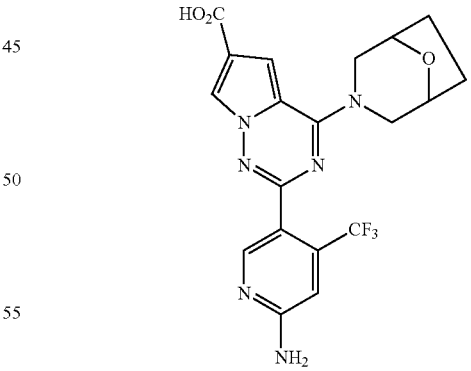

Compound 23b was prepared by the method which was identical with that for preparing compound 23a, wherein compound 22b (250 mg, 0.45 mmol) was used as the starting material. White solid (102 mg, 51.9%). m.p. 284-285° C. ¹H NMR (300 MHz, DMSO-d₆): δ 12.44 (br s, 1H), 8.36 (s, 1H), 8.11 (s, 1H), 7.30 (s, 1H), 6.82 (s, 3H), 4.47 (br s, 2H), 4.42 (br s, 2H), 3.32 (br s, 2H), 1.87-1.84 (m, 2H), 1.75-1.68 (m, 2H). LC-MS: 435 (M+1).

(S)-2-(6-amino-4-(trifluoromethyl)pyridin-3-yl)-4-(3-methylmorpholino)pyrrolo[2,1-f][1,2,4]tri azine-6-carboxylic acid (23c)

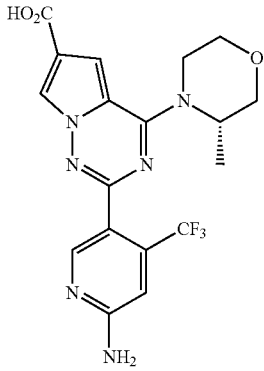 [SMILES: C[C@H]1COCCN1c1nc(-c2cnc(N)cc2C(F)(F)F)nn2cc(C(=O)O)cc12]

Compound 23c was prepared by the method which was identical with that for preparing compound 23a, wherein compound 22c (1.8 g, 3.46 mmol) was used as the starting material. White solid (1.33 g, 91.2%). m.p.>300° C. $^1$H NMR (400 MHz, DMSO-$d_6$): δ 12.76 (s, 1H), 8.36 (s, 1H), 8.11 (d, J=1.3 Hz, 1H), 7.30 (s, 1H), 6.85 (s, 2H), 6.82 (s, 1H), 4.89 (br, 1H), 4.52 (br, 1H), 3.97 (d, J=8.2 Hz, 1H), 3.76-3.63(m, 2H), 3.51 (t, J=10.7 Hz, 2H), 1.36(s, 3H). LC-MS: 423 (M+1).

28. Preparation of Compounds 24

The preparation of compounds 24 was identical with that for compound 12.

(2-(6-amino-4-(trifluoromethyl)pyridin-3-yl)-4-morpholinopyrrolo[2,1-f][1,2,4]triazin-6-yl)(4-(methylsulfonyl)piperazin-1-yl)methanone (24a)

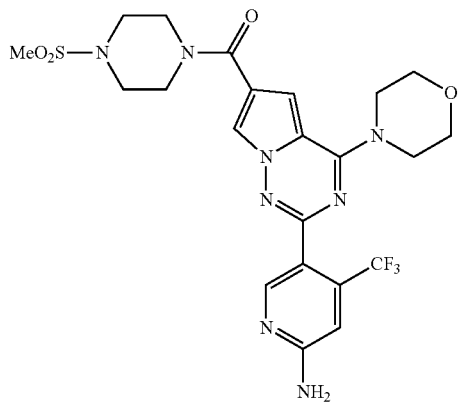 [SMILES: CS(=O)(=O)N1CCN(C(=O)c2cc3c(N4CCOCC4)nc(-c4cnc(N)cc4C(F)(F)F)nn3c2)CC1]

Compound 24a was prepared from 220 mg of compound 23a (0.54 mmol). White solid (253 mg, 84.7%). m.p. 197-198° C. $^1$H NMR (300 MHz, DMSO-$d_6$): δ 8.36 (s, 1H), 8.04 (s, 1H), 7.18 (s, 1H), 6.83 (s, 3H), 4.04-3.92 (m, 4H), 3.73 (br s, 8H), 3.20-3.11 (m, 4H), 2.91 (s, 3H). MS (EI) m/e (%): 554 (68, M$^+$).

(2-(6-amino-4-(trifluoromethyl)pyridin-3-yl)-4-(8-oxa-3-azabicyclo[3.2.1]octan-3-yl)pyrrolo[2,1-f][1,2,4]triazin-6-yl)(4-(methylsulfonyl)piperazin-1-yl)methanone (24b)

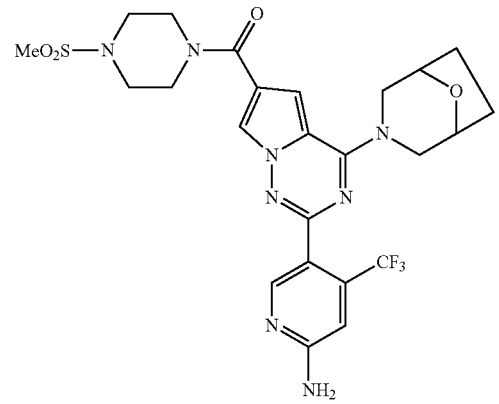 [SMILES: CS(=O)(=O)N1CCN(C(=O)c2cc3c(N4CC5CCC(C4)O5)nc(-c4cnc(N)cc4C(F)(F)F)nn3c2)CC1]

Compound 24b was prepared from 90 mg of compound 23b (0.21 mmol). White solid (113 mg, 93.8%). m.p. 175° C. $^1$H NMR (300 MHz, CDCl$_3$): δ 8.52 (s, 1H), 7.77 (d, J=1.7 Hz, 1H), 6.96 (d, J=1.7 Hz, 1H), 6.81 (s, 1H), 4.86 (s, 2H), 4.49 (br s, 4H), 3.91 (t, J=4.6 Hz, 4H), 3.55 (br s, 2H), 3.28 (t, J=4.6 Hz, 4H), 2.81 (s, 3H), 2.04-1.95 (m, 2H), 1.89-1.79 (m, 2H). LC-MS: 581 (M+1).

(S)-(2-(6-amino-4-(trifluoromethyl)pyridin-3-yl)-4-(3-methylmorpholino)pyrrolo[2,1-f][1,2,4]triazin-6-yl)(4-(methylsulfonyl)piperazin-1-yl)methanone (24c)

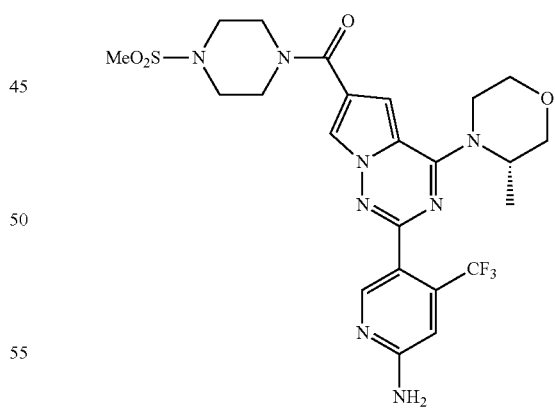

Compound 24c was prepared from 2.42 g of compound 23c (4.86 mmol) as the starting material. Light yellow solid (3 g, 92.2%). m.p. 200-202° C. 1H NMR (300 MHz, CDCl3): δ 8.52 (s, 1H), 7.78 (d, J=1.7 Hz, 1H), 6.97 (d, J=1.7 Hz, 1H), 6.81 (s, 1H), 4.90 (s, 3H), 4.81-4.40 (m, 1H), 4.03 (d, J=7.4 Hz, 1H), 3.91 (t, J=4.8 Hz, 4H), 3.83-3.72 (m, 2H), 3.66-3.56 (m, 2H), 3.28 (t, J=4.8 Hz, 4H), 2.81 (s, 3H), 1.48 (d, J=6.2 Hz, 3H). LC-MS: 569 (M+1).

29. Preparation of 5-(6-((4-(methylsulfonyl)piperazin-1-yl)methyl)-4-morpholinopyrrolo[2,1-f][1,2,4]triazin-2-yl)-4-(trifluoromethyl)pyridin-2-amine (I-27)

Compound I-27 was prepared from 200 mg of compound 24a (0.36 mmol) as the starting material. The preparation process was similar to that of compound 13. A preparative plate (dichloromethane:methanol=20:1) was used for purification. Light yellow solid (43 mg, 22.0%). m.p. 122-123° C. 1H NMR (300 MHz, CDCl3): δ 8.51 (s, 1H), 7.59 (s, 1H), 6.80 (s, 1H), 6.67 (s, 1H), 4.89 (s, 2H), 4.04(t, J=4.4 Hz, 4H), 3.82(t, J=4.4 Hz, 4H), 3.64 (s, 2H), 3.27 (br s, 4H), 2.78 (s, 3H), 2.62 (br s, 4H). MS (EI) m/e (%): 540 (M+, 5).

30. Preparation of 1-(4-fluorophenyl)-3-(5-(6-((4-(methylsulfonyl)piperazin-1-yl)methyl)-4-morpholinopyrrolo[2,1-f][1,2,4]triazin-2-yl)-4-(trifluoromethyl)pyridin-2-yl)urea (I-28)

I-28 was prepared from 30 mg I-27 (0.055 mmol) as the starting material. The preparation process was the same as the synthesis of compound I-1. A preparative plate (dichloromethane:methanol=10:1) was used for purification. White solid (7 mg, 18.6%). m.p. 204-205° C. 1H NMR (300 MHz, CDCl3): δ 11.38 (s, 1H), 9.37 (s, 1H), 8.75 (s, 1H), 7.62 (s, 1H), 7.57 (dd, J=8.5, 4.4 Hz, 2H), 7.33 (s, 1H), 7.06 (t, J=8.5 Hz, 2H), 6.72 (s, 1H), 4.10-4.01 (m, 4H), 3.89-3.81 (m, 4H), 3.67 (s, 2H), 3.30 (br s, 4H), 2.79 (s, 3H), 2.64 (br s, 4H). ESI-MS: 678 (M+1).

31. Preparation of 5-(4-(8-oxa-3-azabicyclo[3.2.1]octan-3-yl)-6-((4-(methylsulfonyl) piperazin-1-yl)methyl)pyrrolo[2,1-f][1,2,4]triazin-2-yl)-4-(trifluoromethyl)pyridin-2-amine (I-29)

I-29 was prepared from 100 mg of compound 24b (0.17 mmol). The preparation process was the same as that of compound 13. A preparative plate (dichloromethane:methanol=20:1) was used for purification. White solid (17 mg, 17.4%). m.p. 138° C. 1H NMR (300 MHz, CDCl3): δ 8.50 (s, 1H), 7.57 (d, J=1.2 Hz, 1H), 6.79 (s, 1H), 6.63 (d, J=1.2 Hz, 1H), 4.92 (s, 2H), 4.48 (br s, 4H), 3.61 (s, 2H), 3.52 (br s, 1H), 3.47 (br s, 1H), 3.26 (t, J=4.8 Hz, 4H), 2.77 (s, 3H), 2.60 (t, J=4.8 Hz, 4H), 2.00-1.96 (m, 2H), 1.89-1.79 (m, 2H). MS (EI) m/e (%): 566 (M+, 5).

32. Preparation of 1-ethyl-3-(5-(6-((4-(methylsulfonyl)piperazin-1-yl)methyl)-4-morpholino pyrrolo[2,1-f][1,2,4]triazin-2-yl)-4-(trifluoromethyl)pyridin-2-yl)urea (I-30)

Ethyl isocyanate (85 mg, 1.2 mmol) was added to the solution of I-27 (110 mg, 0.2 mmol) and 1,8-diazacyclo[5.4.0]undec-7-ene (DBU, 183 mg, 1.2 mmol) in dichloromethane and stirred for two days at room temperature. Diethyl ether was used for recrystallization and 74 mg (60.5%) of white solid was obtained. m.p. 208° C. (decomposition). 1H NMR (300 MHz, DMSO-d6): δ 9.99 (br s, 1H), 8.62 (s, 1H), 8.18 (s, 1H), 7.78 (br s, 1H), 7.73 (s, 1H), 6.95 (s, 1H), 3.98 (br s, 4H), 3.73 (br s, 4H), 3.59 (s, 2H), 3.33 (br s, 2H), 3.16 (q, J=7.5 Hz, 2H), 3.11 (br s, 4H), 2.86 (s, 3H), 1.62 (br s, 2H), 1.09 (t, J=7.5 Hz, 3H). LC-MS: 612 (M+1).

33. Preparation of Compounds (I-31~I-33)

General preparation method: To the solution of I-27 (54 mg, 0.1 mmol) and triethylamine (101 mg, 1 mmol) in chloroform was added the corresponding chloroformate (0.3 mmol). The reaction mixture was stirred at room temperature for four days. The crude product was purified by column chromatography with dichloromethane/methanol (10:1).

Phenyl (5-(6-((4-(methylsulfonyl)piperazin-1-yl)methyl)-4-morpholinopyrrolo[2,1-f][1,2,4]triazin-2-yl)-4-(trifluoromethyl)pyridin-2-yl)carbamate (I-31)

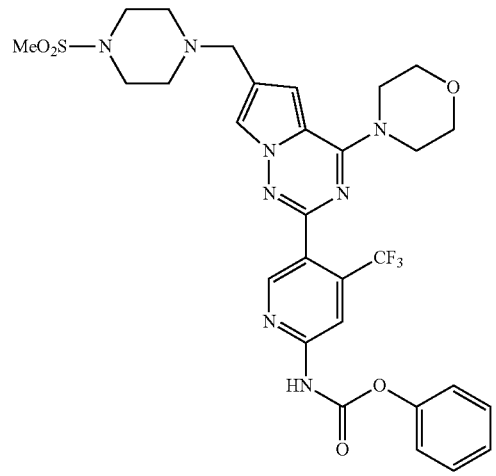 [SMILES: CS(=O)(=O)N1CCN(Cc2cc3c(N4CCOCC4)nc(-c4cnc(NC(=O)Oc5ccccc5)cc4C(F)(F)F)nn3c2)CC1]

Light yellow solid. Yield 37.1%. m.p. 108-110° C. 1H NMR (300 MHz, DMSO-d6): δ 11.42 (s, 1H), 8.79 (s, 1H), 8.27 (s, 1H), 7.76 (s, 1H), 7.49-7.44 (m, 2H), 7.32-7.27 (m, 3H), 6.98 (s, 1H), 3.99 (br s, 4H), 3.74 (br s, 4H), 3.60 (s, 2H), 3.31 (br s, 4H), 3.12 (br s, 4H), 2.87 (s, 3H). LC-MS: 661 (M+1).

Ethyl (5-(6-((4-(methylsulfonyl)piperazin-1-yl)methyl)-4-morpholinopyrrolo[2,1-f-][1,2,4]triazin-2-yl)-4-(trifluoromethyl)pyridin-2-yl)carbamate (I-32)

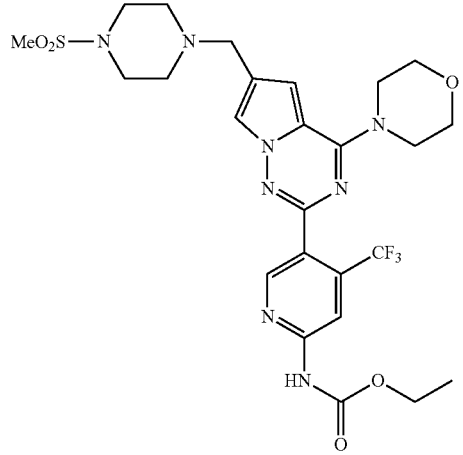 [SMILES: CCOC(=O)Nc1cc(C(F)(F)F)c(-c2nc(N3CCOCC3)c3cc(CN4CCN(S(C)(=O)=O)CC4)cn3n2)cn1]

White solid. Yield 50.7%. m.p. 211-213° C. 1H NMR (300 MHz, CDCl3): δ 8.71 (s, 1H), 8.41 (s, 1H), 7.92(s, 1H), 7.60 (s, 1H), 6.67 (s, 1H), 4.30 (q, J=7.2 Hz, 2H), 4.05 (t, J=4.5 Hz, 4H), 3.83 (t, J=4.5 Hz, 4H), 3.63 (s, 2H), 3.26 (br s, 4H), 2.78 (s, 3H), 2.61 (br s, 4H), 1.36 (t, J=7.2 Hz, 3H). LC-MS: 613 (M+1).

Methyl (5-(6-((4-(methylsulfonyl)piperazin-1-yl)methyl)-4-morpholinopyrrolo[2,1-f][1,2,4]triazin-2-yl)-4-(trifluoromethyl)pyridin-2-yl)carbamate (I-33)

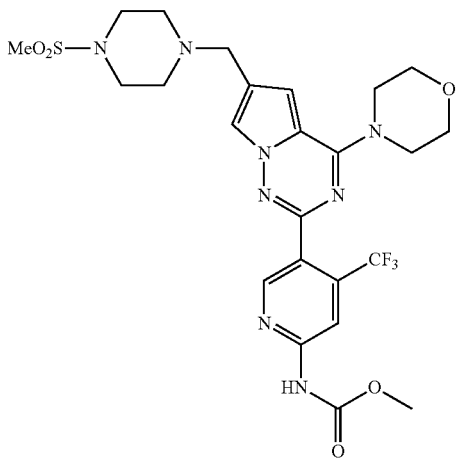 [SMILES: COC(=O)Nc1cc(C(F)(F)F)c(-c2nc(N3CCOCC3)c3cc(CN4CCN(S(C)(=O)=O)CC4)cn3n2)cn1]

White solid (43.4%). m.p. 212-214° C. 1H NMR (300 MHz, CDCl3): δ 8.70 (s, 1H), 8.40 (s, 1H), 7.60 (d, J=1.5 Hz, 1H), 6.67 (s, 1H), 4.05 (t, J=4.5 Hz, 4H), 3.85 (s, 3H), 3.83 (t, J=4.5 Hz, 4H), 3.63 (s, 2H), 3.27 (br s, 4H), 2.78 (s, 3H), 2.61 (br s, 4H). LC-MS: 599 (M+1).

34. Preparation of (S)-5-(4-(3-methylmorpholino)-6-((4-(methylsulfonyl)piperazin-1-yl) methyl)pyrrolo[2,1-f][1,2,4]triazin-2-yl)-4-(trifluoromethyl)pyridin-2-amine (I-34)

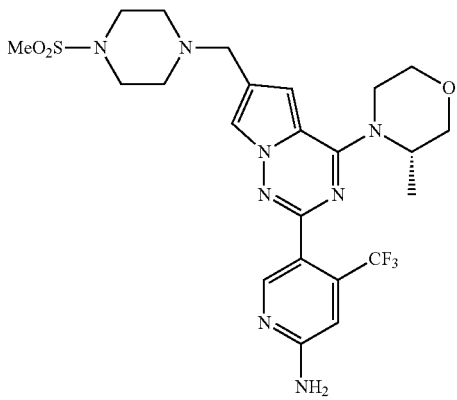 [SMILES: C[C@H]1COCCN1c1nc(-c2cnc(N)cc2C(F)(F)F)nn2cc(CN3CCN(S(C)(=O)=O)CC3)cc12]

At −40° C., 1 M borane-THF (80 mL) was added dropwise to the solution of compound 24c (1.8 g, 3.17 mmol) in 50 mL of tetrahydrofuran. After the reaction proceeded 0.5 hours at this temperature, the reaction system was refluxed for 2 hours, and then cooled to below 0° C. 100 mL of concentrated hydrochloric acid was added dropwise and afterwards refluxed for 1 hour. When most of hydrochloric acid was removed by rotation evaporation, the pH of the solution was adjusted to about 8 by using saturated sodium carbonate solution. After extracted for three times with ethyl acetate, the organic phase was dried over anhydrous sodium sulfate, and the solvent was removed under reduced pressure to give the crude product. The crude product was purified by colume chromatography with dichloromethane/methanol (40:1) to afford white solid (56.9%). m.p. 262° C. 1H NMR (300 MHz, DMSO-d6): δ 8.34 (s, 1H), 7.68 (s, 1H), 6.88 (s, 1H), 6.82 (s, 1H), 6.77 (s, 2H), 4.87 (br s, 1H), 4.47 (br s, 1H), 3.96 (br s, 1H), 3.77-3.41 (m, 8H), 3.11 (s, 6H), 2.87 (s, 3H), 1.32 (s, 3H). LC-MS: 555 (M+1).

35. Preparation of (S)-methyl (5-(4-(3-methylmorpholino)-6-((4-(methylsulfonyl)piperazin-1-yl) methyl)pyrrolo[2,1-f][1,2,4]triazin-2-yl)-4-(trifluoromethyl)pyridin-2-yl)carbamate (I-35)

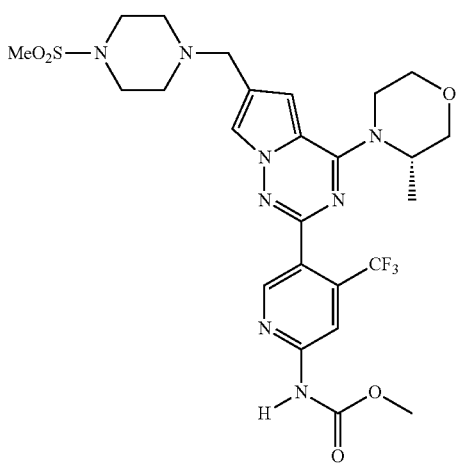 [SMILES: COC(=O)Nc1cc(C(F)(F)F)c(-c2nc(N3CCOC[C@@H]3C)c3cc(CN4CCN(S(C)(=O)=O)CC4)cn3n2)cn1]

At −40° C., methyl chloroformate (28.85 mmol) was added to the solution of I-34 (880 mg, 1.44 mmol) and triethylamine (1.5 g, 14.4 mmol) in chloroform and stirred for 2 h. The rude product was purified by column chromatography with dichloromethane/methanol (60:1) to afford white solid (44.2%). m.p. 150-152° C. 1H NMR (400 MHz, CDCl3): δ 8.70 (s, 1H), 8.41 (s, 1H), 8.22 (s, 1H), 7.60 (s, 1H), 6.67 (s, 1H), 4.92 (br s, 1H), 4.56 (br s, 1H), 4.03 (d, J=7.9 Hz, 1H), 4.00-3.52 (m, 9H), 3.27 (s, 4H), 2.78 (s, 3H), 2.62 (s, 4H), 1.47 (d, J=6.6 Hz, 3H). LC-MS: 613 (M+1).

36. Preparation of (S)-1-ethyl-3-(5-(4-(3-methylmorpholino)-6-((4-(methylsulfonyl) piperazin-1-yl) methyl)pyrrolo[2,1-f][1,2,4]triazin-2-yl)-4-(trifluoromethyl)pyridin-2-yl)urea (I-36)

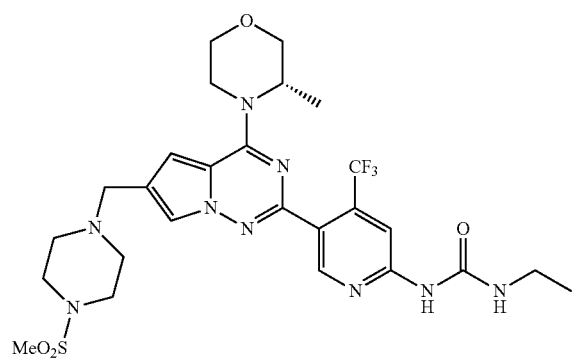 [SMILES: CCNC(=O)Nc1cc(C(F)(F)F)c(-c2nc(N3CCOC[C@@H]3C)c3cc(CN4CCN(S(C)(=O)=O)CC4)cn3n2)cn1]

Compound I-36 was prepared by the same preparation method as that of compound I-30. White solid, 1H NMR (300 MHz, CDCl3) δ 9.45 (s, 1H), 9.01 (br s, 1H), 8.63 (s, 1H), 7.59 (s, 1H), 7.30 (s, 1H), 6.67 (s, 1H), 4.93 (br s, 1H), 4.56 (br s, 1H), 4.03 (d, J=7.5 Hz, 1H), 3.89-3.69 (m, 2H), 3.64 (s, 2H), 3.44 (q, J=6.9 Hz, 2H), 3.39-3.11 (m, 6H), 2.78 (s, 3H), 2.62 (s, 4H), 1.47 (d, J=6.7 Hz, 3H), 1.26 (t, J=7.2 Hz, 3H).

37. 1-Ethyl-3-(5-(6-((4-(methylsulfonyl)piperazin-1-yl) methyl)-4-morpholinopyrrolo[2,1-f] [1,2,4]triazin-2-yl)-4-(trifluoromethyl)pyridin-2-yl)urea mesylate

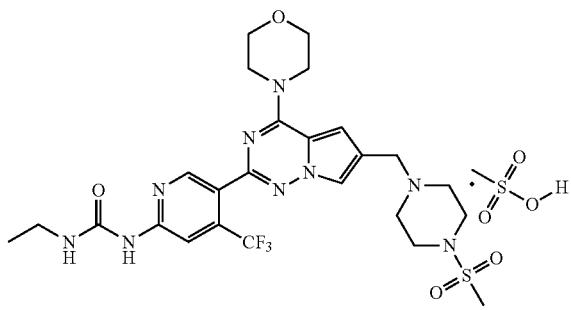

5% solution of methane sulfonic acid in tetrahydrofuran (600 μL, 0.47 mmol) was added to the solution of I-30 (220 mg, 0.36 mmol) in 10 mL chloroform and stirred for 1 h at room temperature. The pure product was obtained by filtration. White powder (99.0%). m.p. 220° C. (decomposition). 1H NMR (300 MHz, DMSO-d6): δ 9.83 (br s, 1H), 9.63 (s, 1H), 8.63 (s, 1H), 8.12 (s, 1H), 7.94 (s, 1H), 7.37 (s, 1H), 7.17 (s, 1H), 4.43 (s, 2H), 4.01 (s, 4H), 3.75 (s, 6H), 3.50 (s, 2H), 3.28-3.01 (m, 6H), 3.0 (s, 3H), 2.32 (s, 3H), 1.08 (t, J=7.2 Hz, 3H). 13C NMR (126 MHz, DMSO) δ 155.03, 154.57, 153.91, 153.00, 150.65, 136.78 (q, J=32.1 Hz, CF3C), 123.24 (q, J=274.8 Hz, CF3), 123.51, 121.78, 113.99, 113.09, 108.30 (q, J=5.2 Hz, CF3CCH), 107.81, 66.37, 52.23, 50.49, 46.00, 42.93, 35.55, 34.45, 15.67. 15.67.

38. Methyl (5-(6-((4-(methylsulfonyl)piperazin-1-yl)methyl)-4-morpholinopyrrolo[2,1-f][1,2,4]triazin-2-yl)-4-(trifluoromethyl)pyridin-2-yl)carbamate mesylate

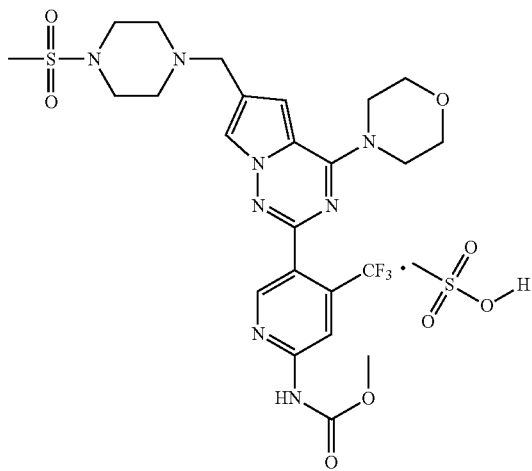

5% solution of methane sulfonic acid in tetrahydrofuran (978 μL, 0.77 mmol) was added to the solution of I-33 (300 mg, 0.50 mmol) in 15 mL of tetrahydrofuran and stirred for 5 h at room temperature. Diethyl ether was added to the system until a plenty of solids precipitated. The pure product was obtained by filtration. White solid (100%). m.p. 240° C. (decomposition). 1H NMR (300 MHz, DMSO-d6): δ 10.94 (s, 1 H), 9.82 (s, 1 H), 8.74 (s, 1 H), 8.32 (s, 1 H), 7.99 (s, 1 H), 7.19 (s, 1H), 4.46 (s, 2 H), 4.03 (t, J=4.8 Hz, 4 H), 3.78 (t, J=4.8 Hz, 4 H), 3.75 (s, 3 H), 3.67-3.43 (m, 4H), 3.27-3.05 (m, 4 H), 3.02 (s, 3 H), 2.33 (s, 3 H). 13C NMR (126 MHz, DMSO-d6): δ 154.58, 154.16, 153.88, 152.90, 151.07, 137.029 (q, J=31 Hz, CF3C), 125.19, 123.23 (q, J=274.9 Hz, CF3), 121.84, 113.99, 113.07, 108.60 (q, J=5 Hz, CF3CH), 107.88, 66.35, 52.78, 52.22, 50.49, 46.03, 42.95, 35.57, 25.59.

39. (S)-methyl (5-(4-(3-methylmorpholino)-6-((4-(methylsulfonyl)piperazin-1-yl)methyl) pyrrolo[2,1-f][1,2,4]triazin-2-yl)-4-(trifluoromethyl)pyridin-2-yl) carbamate mesylate

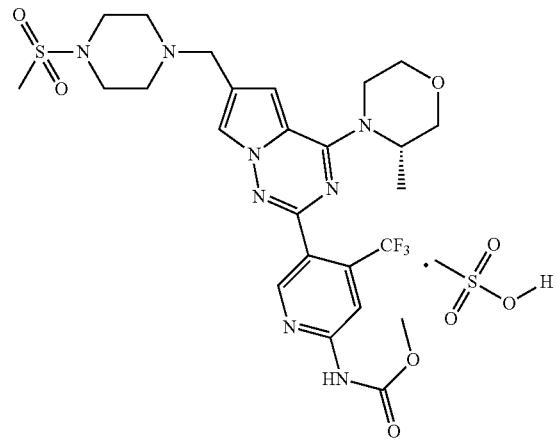

5% solution of methane sulfonic acid in tetrahydrofuran (589 μL, 0.46 mmol) was added to the solution of I-35 (231 mg, 0.38 mmol) in 15 mL tetrahydrofuran and stirred for 3 h at room temperature. Tetrahydrofuran was removed under the reduced pressure to give a jelly. A small amount of methanol was added to dissolve the jelly. And then diethyl ether was added dropwise until solid precipitated. The pure product was obtained by filtration. White powder (80.72%). m.p. 210° C. (decomposition). 1H NMR (300 MHz, DMSO-d6): δ 10.91 (s, 1H), 9.86 (s, 1H), 8.73 (s, 1H), 8.31 (s, 1H), 7.98 (s, 1H), 7.17 (s, 1H), 4.90 (br s, 1H), 4.45 (br s, 3H), 4.00 (d, J=7.9 Hz, 1H), 3.88-3.61 (m, 7H), 3.53 (s, 4H), 3.15 (br s, 4H), 3.01 (s, 3H), 2.41-2.26 (m, 3H), 1.39 (br s, 3H). 13C NMR (126 MHz, DMSO-d6): δ 154.60, 154.15, 153.68, 152.96, 151.09, 136.91 (q, J=32.5 Hz, CF3C), 125.26, 123.24 (q, J=274.9 Hz, CF3) 121.89, 114.05, 113.09, 108.60 (q, J=5.5 Hz, CF3CH), 107.95, 70.51, 66.46, 52.78, 52.20, 50.48, 42.93, 35.58, 31.17, 13.19.

Example 2

Biological Activity Analysis

1. Inhibition on PI3K Kinase Activity
Experimental Method
The activity of purified kinase was detected with Kinase-Glo® Plus kinase luminescent assay by measuring the amount of the remaining Kinase in the solution after the kinase reaction was completed. Kinase reaction was performed in a 384-well white plate (Greiner), 1 μL of tested compound or control DMSO was added into each well containing 5 μL reaction buffer [10 mM Tris-HCl pH 7.5, 50 mM NaCl, 3 mM MgCl2.1 mM DTT (dithiothreitol), 0.05% CHAPS (3-[(3-Cholamidopropyl)dimethylammonio]-1-propanesulfonate, 3-(3-cholaminopropyl)-dimethylamino-1-propanesulfonic acid), and the reaction buffer was supplemented with 12 μM of substrate, D-myo-Phosphatidylinositol-4,5-bisphosphate (4,5-phosphatidyl inositol diphosphate) and 2 μM ATP (adenosine triphosphate). And then 4 μL reaction buffer containing 62.5 nM PI3Kα or non-PI3Kα control was added to initiate the kinase reaction. After reaction was performed for 1 hour at room temperature, 10 μL of Kinase Glo-Plus mixture was added and incubated for 1 hour to quench the reaction. The chemiluminescence value was detected with EnVision 2104 multifunctional microplate reader (Perkinelmer).

Experimental Results

The experimental results (table 2) showed that the inhibitory activities of the following seven compounds of the present invention on PI3Kα were comparable to or more potent than that of PI-103. And they were I-22 (9.59 nM), I-27 (8.37 nM), I-28 (9.30 nM), I-30 (8.19 nM), I-32 (7.15 nM), I-33 (2.84 nM), and I-35 (5.67 nM), respectively.

TABLE 2

IC50 of pyrrolo[2,1-f][1,2,4]triazine compounds on PI3α

| Compound No. | X | $R_1$ | $R_2$ | $R_3$ | $R_4$ | $IC_{50}$ (nM) |
|---|---|---|---|---|---|---|
| PI-103 | | | | | | 9.79 |
| I-22 | C | 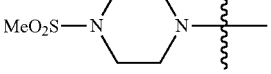 | H | 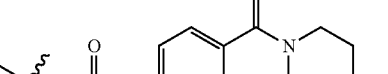 | 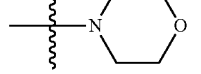 | 9.59 |
| I-27 | N | 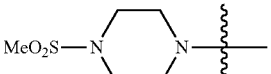 | $CF_3$ | $NH_2$ | 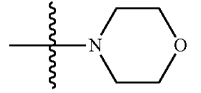 | 8.37 |
| I-28 | N | 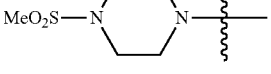 | $CF_3$ | 4-FPhNHCONH | 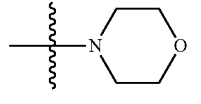 | 9.30 |
| I-30 | N | 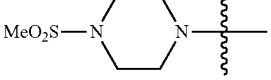 | $CF_3$ | EtNHCONH | 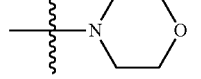 | 8.19 |
| I-32 | N |  | $CF_3$ | EtOCONH | 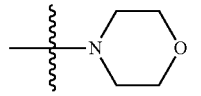 | 7.15 |
| I-33 | N | 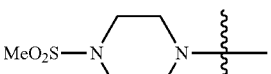 | $CF_3$ | MeOCONH | 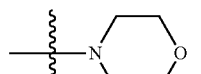 | 2.84 |
| I-35 | N | 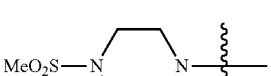 | $CF_3$ | MeOCONH | 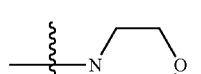 | 5.67 |

The Inhibitory Activity on the Proliferation of Human Rhabdomyosarcoma Rh30 Cells Rh30 cells were seeded in a 96-well plate at 3000 cells/well. After the cells adhered, tested compounds at concentration of 10, 3, 1, 0.3, or 0.1 μM were added, and incubated for 72 h. The culture media were discarded and cells were fixed with trichloroacetic acid. After washed with distilled water for five times and dried, sulfonylrhodamine B was added. After washed with 1% glacial acetic acid for five times and dried, trihydroxymethylaminomethane buffer was added. OD value was measured by using a microplate reader at a wavelength of 560 nm. The inhibitory rate was calculated and the results were shown in table 3. The above results showed that compounds of the present invention display potent inhibitory activity on Rh30 cell proliferation, wherein the 1050 values of I-24, I-25 and I-28 even reached tens of nanomolar.

TABLE 3

IC50s of pyrrolo[2,1-f][1,2,4]triazine compounds
against proliferation of Rh30 cells

| | Compound | | | | | | | | |
|---|---|---|---|---|---|---|---|---|---|
| | I-4 | I-5 | I-6 | I-9 | I-14 | I-22 | I-24 | I-25 | I-26 |
| IC50 (μM) | 0.4 | 1.24 | 1.36 | 0.99 | 0.5 | 0.54 | 0.074 | 0.039 | 0.24 |

| | Compound | | | | | | | |
|---|---|---|---|---|---|---|---|---|
| | I-27 | I-28 | I-29 | I-30 | I-31 | I-33 | I-34 | I-35 |
| IC50 (μM) | 0.73 | 0.074 | 3.42 | 0.82 | 5.06 | 2.52 | 0.53 | 0.47 |

TABLE 4

The inhibitory activity of I-30 and I-33 on a panel of human cancer cells

| | Compound | | |
|---|---|---|---|
| Cell line | GDC0941 (μM) | I-33 (μM) | I-30 (μM) |
| B-BT474 | 0.256 | 0.062 | 0.032 |
| B-MCF-7 | 0.519 | — | 2.51 |
| C-HCT-116 | 8.1 | 10 | 9.7 |
| C-LOVO | 0.517 | 1.33 | 0.493 |
| E-RL95-2 | 2.2 | 5.3 | 2 |
| G-MKN-45 | 1.67 | 3.4 | 1.55 |
| L-BEL-7402 | 3.2 | 4.9 | 3.2 |
| LG-NCI-H23 | 1.2 | 0.73 | 0.89 |
| LG-NCI-H460 | 1.66 | 1.52 | 0.66 |
| O-SKOV-3 | 0.316 | 0.277 | 0.046 |
| P-PC-3 | 0.636 | 1.58 | 0.601 |
| S-RH30 | 0.478 | 0.486 | 0.256 |

2. The Effects of I-33 on PI3K Signaling in Human Rhabdomyosarcoma Rh30 Cells and Human Glioma U87MG Cells Experimental Method Rh30 and U87MG cells were seeded in 12-well plates at 2×105 cells/well. On the next day, cells were incubated in fresh serum-free culture media subjected to starvation for 24 hours. Cells were then treated with different concentrations of compound I-33 for 1 h. After stimulated with IGF-1 for 10 minutes, the lysed cells were collected, and 4×SDS loading buffer [200 mM Tris.Cl (pH 6.8), 400 mM DTT, 8% SDS (sodium dodecyl sulfate), 0.4% bromophenol blue, 40% glycerol] was added. The cell lysates were boiled for 10 minutes. Aliquot was loaded on polyacrylamide gel and electrophoresis was performed in Tris-glycine electrophoresis buffer (25 mM Tris, 250 mM glycine, 0.1% SDS) at 80-100 V for 2-2.5 hours. The proteins were transformed from gel to nitrocellulose filter membrane by using semidry method. The filter membrane was blocked with blocking solution containing 5% skim milk powder (5% skim milk powder, 20 mM Tris-HCl (pH 7.2-7.4), 150 mM NaCl, 0.1% (v/v) Tween20) in a shaker at room temperature for 2 hours. Then specific primary antibody was added and hybridized at 4° C. overnight. The membrane was washed by washing buffer [20 mM Tris-HCl (pH 7.2-7.4), 150 mM NaCl, 0.1% (v/v) Tween20] for three times at room temperature, 15 minutes each time. A horseradish peroxidase-labeled secondary antibody was added, and the system was placed on a shaker and gently shaken at room temperature for 1 hour. After washed with washing buffer for three times, the membrane was incubated with SuperSignal West Dura Chemiluminescent Substrate (Pierce Inc, Rochford, Ill.). And then the membrane was exposed, developed, and fixed, and pictures were taken.

Experimental Results

The experimental results (FIG. 1) showed that I-33 significantly inhibited the transduction of PI3K signaling in human rhabdomyosarcoma Rh30 cells and human glioma U87MG cells.

Inhibitory Activity of I-30 and I-33 on the Proliferation of Human Cancer Cells from Various Tissues I-30 and I-33 were selected to test their activity on the proliferation of human cancer cells originated from different tissue types. The results were shown in table 4.

As shown in Table 4, the activity of compounds I-30 and I-33 are comparable to that of positive control GDC0941 (which was purchased from Shanghai han-xiang chemical co., LTD., dimesylate) against proliferation of various cell lines such as colon cancer cells C-HCT-116, colorectal cancer cells C-LOVO, endometrial cancer cells E-RL95-2, gastric cancer cells G-MKN-45, hepatoma cells L-BEL-7402, and rhabdomyosarcoma cells S-RH30. However, the activities of the compounds are significantly potent than the positive control in inhibiting the proliferation of B-BT474 cells.

3. The Inhibition Effects on the Growth of Human Neuroglioma U87-MG Xenograft Subcutaneously Transplanted in Nude Mouse Experimental Method Well-developed tumors in nude mice were cut into 1.5 mm3 fragments and transplanted s.c. into the right flank of nude mice under sterile conditions. The diameters of subcutaneously transplanted tumours in nude mice were measured with a vernier calipe. When the tumour reached a volume 100-200 mm3, the mice were randomly assigned into several groups: I-33 mesylate 50 mg/kg group and 25 mg/kg group; I-30 mesylate 50 mg/kg group; GDC0941 dimesylate 50 mg/kg group and control group. Control groups were given the same amount of blank solvent, and treatment groups received tested compounds (p.o.). Compounds were administrated once a day for three weeks. Throughout the experiment, the sizes of the tumours were measured twice per week and meanwile the body weights of mice were weighed. The tumour volume (TV) was calculated as follows: TV=½×a×b2, wherein a and b represent the length and width, respectively. The individual relative tumour volume (RTV) was calculated as follows: RTV=Vt/V0, where V0 is the volume at the beginning of the treatment and Vt is the volume measured every time. Evaluation index of antitumor activity was relative tumor proliferation rate T/C (%), the calculation formula of which was as follows: T/C (%)=(TRTV/CRTV)×100%, TRTV:RTV of treatment group; CRTV:RTV of negative control group.

Experimental Results

Figure 2:
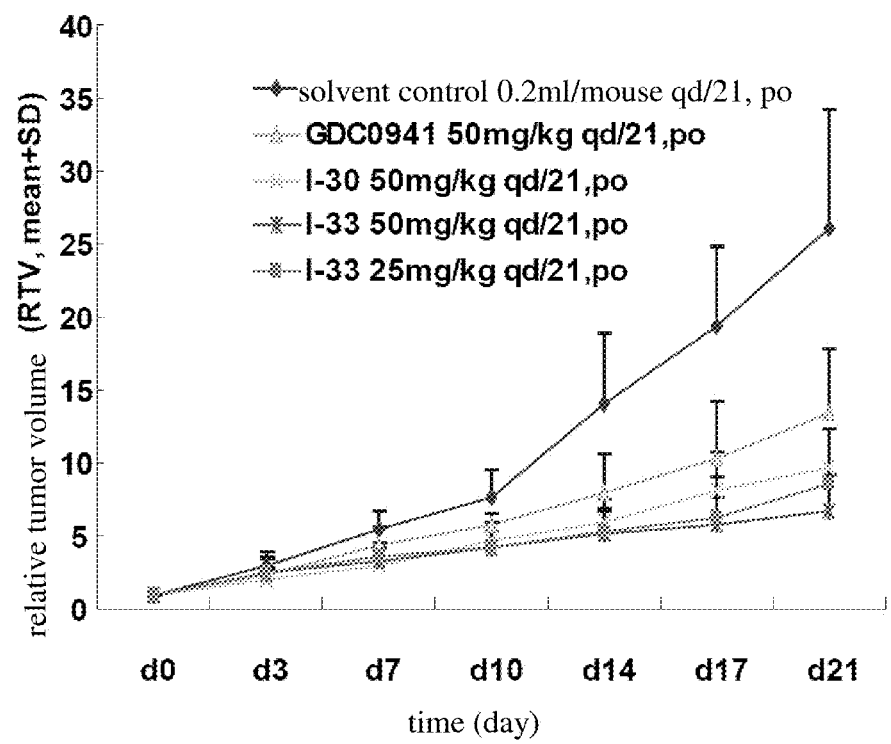
FIG. 2 shows the growth inhibition effects of I-30 and I-33 on subcutaneously transplanted tumors of human glioma U87MG in nude mice.

The experimental results were shown in table 5 and FIG. 2. I-33 mesylate was orally administrated at the dose of 50 mg/kg or 20 mg/kg every day. After one week, the growth of tumor in I-33 treated group significantly slowed down. After successively administrated for three weeks, I-33 mesylate significantly inhibited the growth of subcutaneously transplanted U87mG xenograft in nude mice (FIG. 2). The T/C value on the 21st day was 25.65% and 32.61%, respectively. I-33 mesylate displayed more potent activity than GDC0941 (50 mg/kg) in inhibiting the tumor growth. I-30 mesylate at 50 mg/kg also exhibited significant inhibitory effects on the tumor growth. The T/C value of I-30 mesylate at 50 mg/kg on the 21st day was 37.26%, while that of GDC0941 50 mg/kg group was 51.40%.

TABLE 5

Relative tumor growth rates of human neuroglioma U87-MG xenograft in nude mouse

| Group | Relative tumor proliferation rate T/C (%) | | | | | | |
|---|---|---|---|---|---|---|---|
| | d0 | d3 | d7 | d10 | d14 | d17 | d21 |
| GDC0941 50 mg/kg | 100.00 | 75.12 | 79.34 | 74.75 | 56.86 | 53.57 | 51.40 |
| I-30 (mesylate) 50 mg/kg | 100.00 | 67.89 | 54.35 | 60.45 | 42.46 | 41.64 | 37.26 |
| I-33 (mesylate) 50 mg/kg | 100.00 | 82.76 | 59.61 | 54.74 | 36.93 | 29.89 | 25.65 |
| I-33 (mesylate) 20 mg/kg | 100.00 | 84.69 | 65.90 | 55.24 | 37.48 | 31.92 | 32.61 |

Inhibition on Esophagus Cancer Cell

Compounds BYL719 (shown below), CYH33 (compound I-33) and I-27 were selected to test their activity on the proliferation of 11 species of human esophagus cancer cells. The results were shown in FIG. 3.

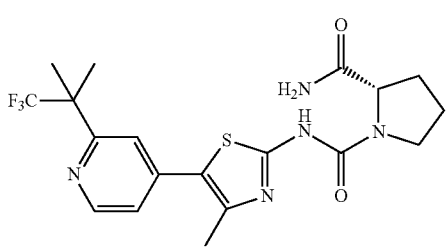

BYL719

Figure 3:
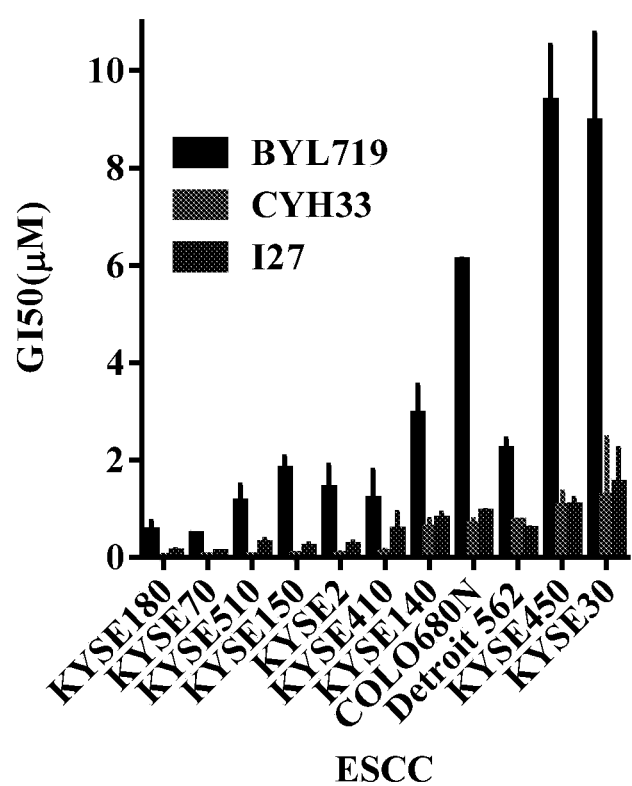
FIG. 3 shows the inhibitory effects of BYL719, CYH33 (compound I-33), and I-27 on proliferation of human esophagus cancer cells.

The results reported in FIG. 3 were the average GI50 value and SD value of three experiments. The results were arranged according to the GI50 value of CYH33. The results showed similar inhibitory activities of BYL719, CYH33 and I-27 toward the various species of esophagus cancer cells. The inhibition rate were not significantly over 100% for each of the esophagus cancer cell lines examined.

4. The Inhibition Effects on the Growth of Human Esophagus Cancer KYSE 410 Xenograft Subcutaneously Transplanted in Nude Mouse Experimental Method Well-developed tumors in nude mice were cut into 1.5 mm3 fragments and transplanted s.c. into the right flank of nude mice under sterile conditions. The diameters of subcutaneously transplanted tumours in nude mice were measured with a vernier calipe. When the tumour reached a volume 170 mm3, the mice were randomly assigned into two treatment groups: CYH33 50 mg/kg group or BYL-719 50 mg/kg group. Control groups were given the same amount of normal saline, and treatment groups received tested compounds (p.o). Compounds were administered orally once every day for 3 weeks. Evaluation index of antitumor activity was relative tumor proliferation rate T/C (%), the calculation formula of which was as follows: T/C (%)=(TRTV/CRTV)×100%, TRTV:RTV of treatment group; CRTV:RTV of negative control group.

Experimental Results

Figure 4:
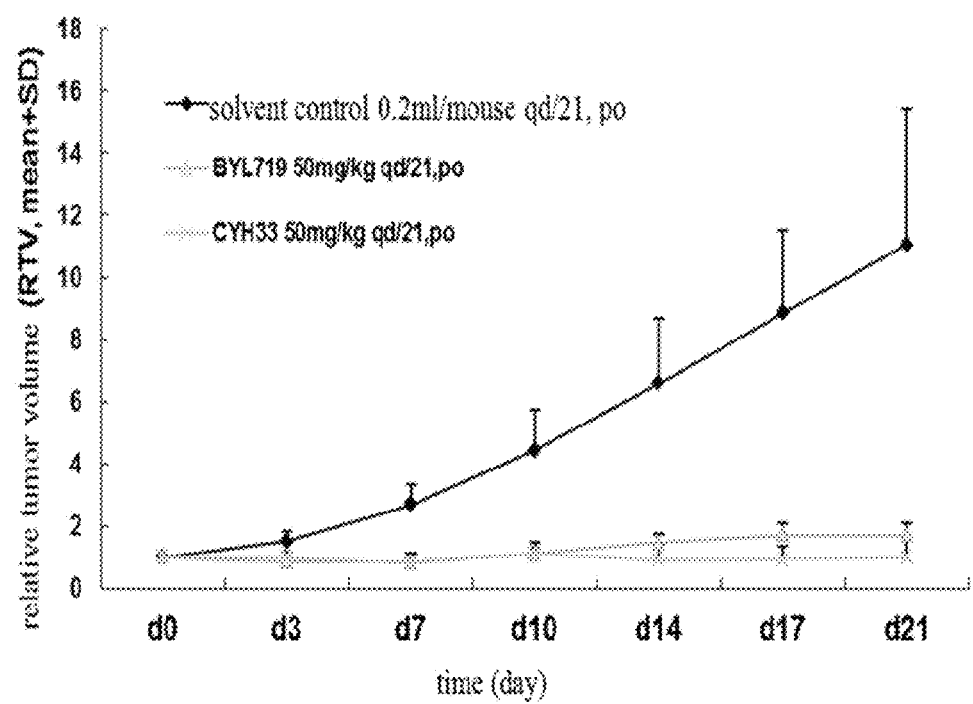
FIG. 4 shows the growth inhibition effects of CYH33 and BYL719 on subcutaneously transplanted tumors of human esophagus cancer KYSE 410 in nude mice.

The experimental results were shown in table 7 and FIG. 4. CYH33 was orally administrated at the dose of 50 mg/kg every day for 3 weeks. After one week, the growth of human esophagus cancer KYSE 410 xenograft in nude mice significantly slowed down. The T/C value on the 21st day was 9.13%. Positive control BYL-719 was orally administrated at the dose of 50 mg/kg every day for 3 weeks, and the growth of human esophagus cancer KYSE 410 xenograft in nude mouse significantly slowed down. The T/C value on the 21st day was 15.37%, which was slightly lower than CYH33 at the same dose.

TABLE 7

Relative tumor growth rates of human esophagus cancer KYSE 410 xenograft in nude mouse

| Group | Relative tumor proliferation rate T/C (%) | | | | | | |
|---|---|---|---|---|---|---|---|
| | d0 | d3 | d7 | d10 | d14 | d17 | d21 |
| BYL-719 50 mg/kg | 100.00 | 56.95 | 31.23 | 24.77 | 22.12 | 19.32 | 15.37 |
| CYH33 50 mg/kg | 100.00 | 65.56 | 30.11 | 25.23 | 13.79 | 10.51 | 9.13 |

What is claimed is:
1. A method for treating cancer, comprises:
administrating to a subject in need thereof an effective amount of a pharmaceutical composition comprising a

TABLE 6

The GI50 value to the proliferation of human esophagus cancer cells of CYH33, BYL719 and I27

| | GI$_{50}$ (μM) | | | | | | | | | | | |
|---|---|---|---|---|---|---|---|---|---|---|---|---|
| | BYL719 | | | | CYH33 | | | | I27 | | | |
| cell line | 1st | 2nd | 3rd | mean | 1st | 2nd | 3rd | mean | 1st | 2nd | 3rd | mean |
| KYSE180 | 0.354 | 0.740 | 0.553 | 0.549 | 0.001 | 0.011 | 0.016 | 0.009 | 0.100 | 0.169 | 0.077 | 0.115 |
| KYSE70 | 0.452 | 0.450 | 0.478 | 0.460 | 0.033 | 0.027 | 0.029 | 0.030 | 0.109 | 0.059 | 0.112 | 0.093 |
| KYSE510 | 1.529 | 0.835 | 1.031 | 1.132 | 0.055 | 0.006 | 0.038 | 0.033 | 0.247 | 0.390 | 0.204 | 0.280 |
| KYSE150 | 1.638 | 2.110 | 1.670 | 1.806 | 0.040 | 0.062 | 0.038 | 0.047 | 0.202 | 0.276 | 0.150 | 0.209 |
| KYSE2 | 1.444 | 0.911 | 1.874 | 1.410 | 0.024 | 0.028 | 0.097 | 0.050 | 0.255 | 0.165 | 0.310 | 0.243 |
| KYSE410 | 1.887 | 0.816 | 0.874 | 1.192 | 0.146 | 0.050 | 0.088 | 0.095 | 0.468 | 0.959 | 0.229 | 0.552 |
| KYSE140 | 2.446 | 3.611 | 2.740 | 2.932 | 0.484 | 0.804 | 0.492 | 0.593 | 0.898 | 0.638 | 0.792 | 0.776 |
| COLO680N | 6.122 | 6.054 | 6.104 | 6.093 | 0.743 | 0.530 | 0.701 | 0.658 | 0.959 | 0.915 | 0.917 | 0.930 |
| Detroit 562 | 1.970 | 2.297 | 2.385 | 2.217 | 0.718 | 0.707 | 0.769 | 0.731 | 0.580 | 0.527 | 0.607 | 0.571 |
| KYSE450 | 8.592 | 10.000 | 8.803 | 9.132 | 1.382 | 0.803 | 0.938 | 1.041 | 1.226 | 1.005 | 0.932 | 1.054 |
| KYSE30 | 10.000 | 6.832 | 10.000 | 8.944 | 2.640 | 0.566 | 0.531 | 1.246 | 2.354 | 1.098 | 1.071 | 1.508 | pharmaceutically acceptable carrier and a pyrrolo[2,1-f][1,2,4]triazine compound of formula I,

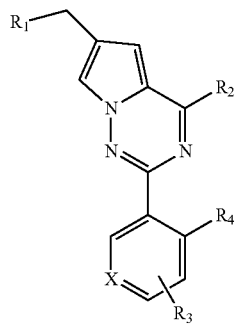

wherein,
X=CH or N;
$R_1$ is —$NR_5R_6$;
$R_2$ is

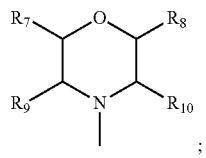
;

$R_3$ is —$NH_2$, —NHC(O)$NHR_{11}$, —NHC(O)$OR_{11}$, —NHC(O)$R_{11}$, —$CH_2OH$, —$CH_2S(O)_2R_{12}$ or —$CH_2NHS(O)_2R_{12}$;
$R_4$ is H or $CF_3$;
$R_5$ and $R_6$ are each independently a C1-C4 alkyl, or combined with the nitrogen atom to which they are attached to form an unsubstituted 5-8 membered saturated heterocycle or a 5-8 membered saturated heterocycle substituted by a substituent, the substituent is —$S(O)_2R_{12}$;
$R_7$, $R_8$, $R_9$ and $R_{10}$ are each independently H or a C1-C3 alkyl, alternatively, $R_7$ and $R_8$, or $R_9$ and $R_{10}$, with the carbon atoms to which they are attached as bridge carbon atoms, form bridged bicylco-heterocycle with morpholine ring;
$R_{11}$ is a C1-C4 alkyl, an unsubstituted C3-C6 cycloalkyl or a C3-C6 cycloalkyl substituted by one or more substituents, an unsubstituted benzyl or a benzyl substituted by one or more substituents, an unsubstituted phenyl or a phenyl substituted by one or more substituents, an unsubstituted isoxazolyl or an isoxazolyl substituted by one or more substituents, or an unsubstituted pyridyl or a pyridyl substituted by one or more substituents, and the one or more substituents are selected from halogen, a C1-C3 alkyl, or a C1-C3 alkoxyl, —$CF_3$, —C(O)$OR_{12}$, —C(O)$NR_{12}R_{15}$,

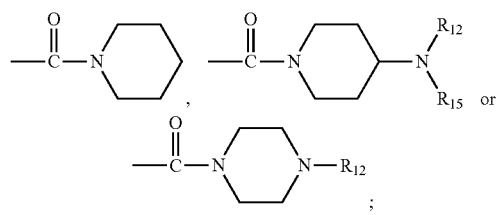

$R_{12}$ and $R_{15}$ are each independently a C1-C3 alkyl;
or a pharmaceutically acceptable salt, or hydrate thereof;
wherein the subject is a human patient having esophageal cancer.

2. The method of claim 1, wherein the compound is of formula A or formula B:

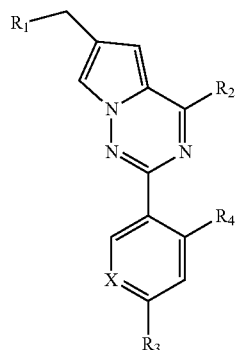

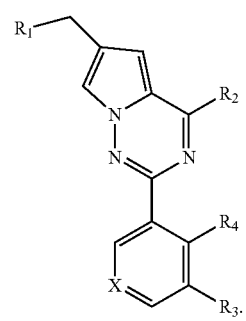

3. The method of claim 1, wherein,
$R_2$ is

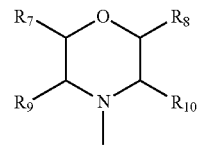
, in which $R_7$, $R_8$, $R_9$, and $R_{10}$ are as defined in claim 1;
$R_5$ and $R_6$ are combined with the nitrogen atom to which they are attached to form an unsubstituted saturated heterocycle or a saturated heterocycle substituted by a substituent, wherein the saturated heterocycle is pyrrolidyl, piperidinyl or piperazinyl, and the substituent is —$S(O)_2R_{12}$, in which $R_{12}$ is defined as in claim 1.

4. The method of claim 3, wherein,
$R_1$ is dimethylamino or 1-methylsulfonyl piperazinyl;
$R_2$ is

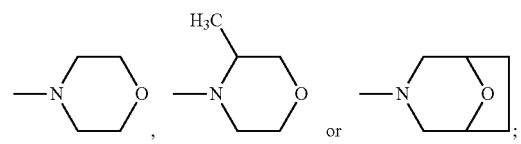

$R_{11}$ is a methyl, an ethyl, a propyl, a cyclopropyl, a tert-butyl, an iso-butyl, a 4-fluorobenzyl, an unsubstituted phenyl or a phenyl substituted by one or more substituents, an unsubstituted isoxazolyl or an isoxazolyl substituted by one or more substituents, or an unsubstituted pyridine ring or a pyridine ring substituted by one or more substituents, and the substituent is selected from a fluorine, a chlorine, a trifluoromethyl, a methyl, a methoxy, an ethoxycarbonyl, a dimethylaminocarbonyl, a 4-methyl-piperazine-1-carbonyl, a piperidine-1-carbonyl and a 4-dimethylamino-piperidine-1-carbonyl.

5. The method of claim 1, wherein the compound is selected from the group consisting of:

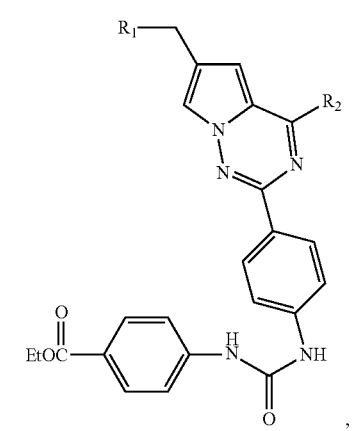

Ia

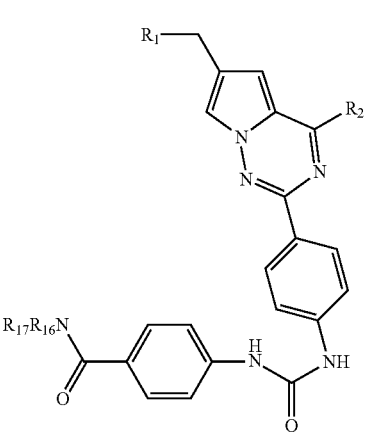

Ib

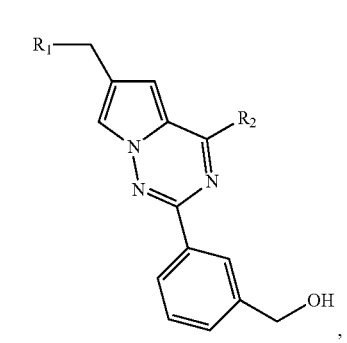

Ic

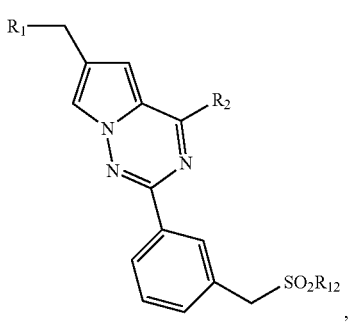

Id

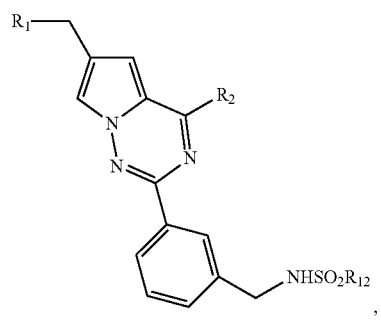

Ie

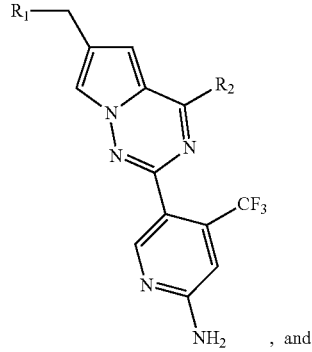

If

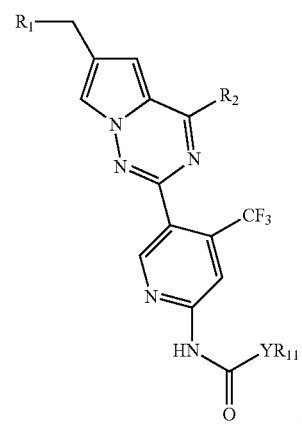

, and

Ig

Y = NH or O wherein, $R_1$, $R_2$, $R_{11}$ and $R_{12}$ are as defined in claim 1, $R_{16}$ and $R_{17}$ are identical or different, and each is independently a C1-C4 alkyl, or $R_{16}$ and $R_{17}$ are combined with the nitrogen atom to which they are attached to form a 4-methyl-piperazinyl, a 4-dimethylamino-piperidinyl, or piperidin-1-yl.

6. The method of claim 1, wherein the compound is selected from the group consisting of:

101
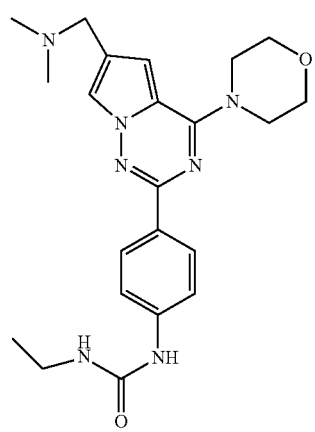
I-1
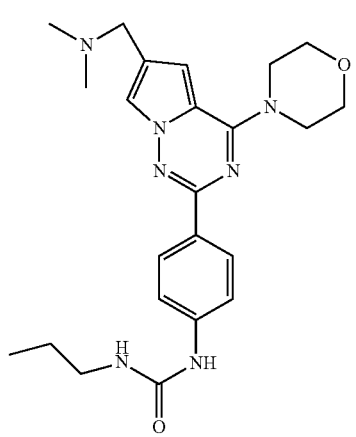
I-2
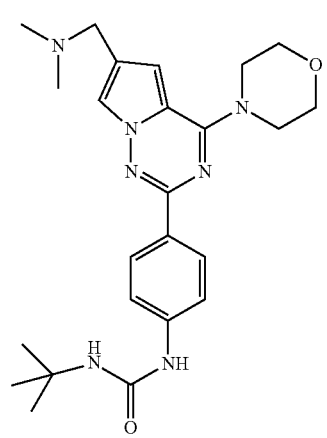
I-3
102
-continued
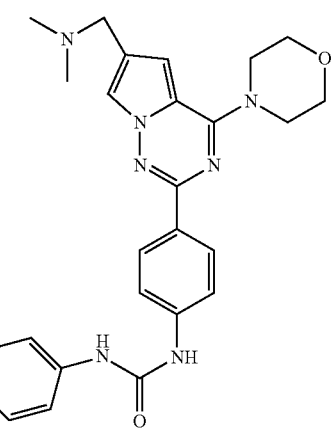
I-4
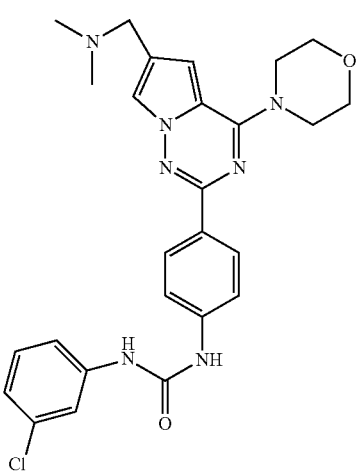
I-5
I-6

I-7
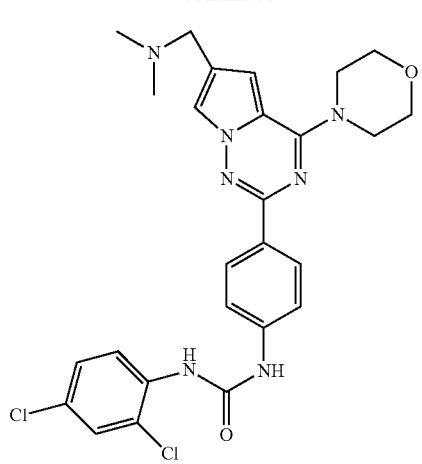
I-8
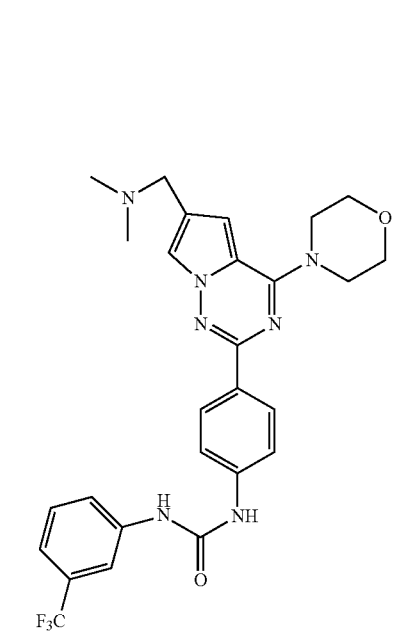
I-9
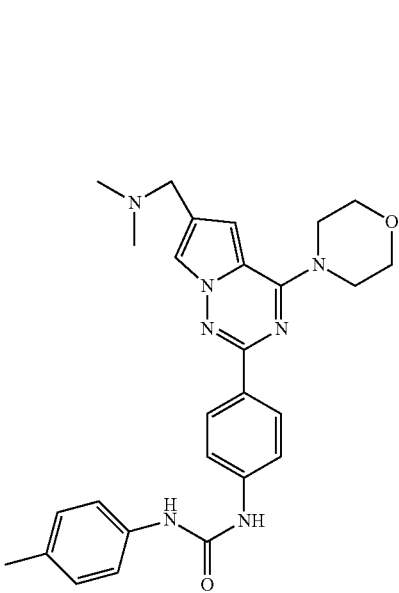
I-10
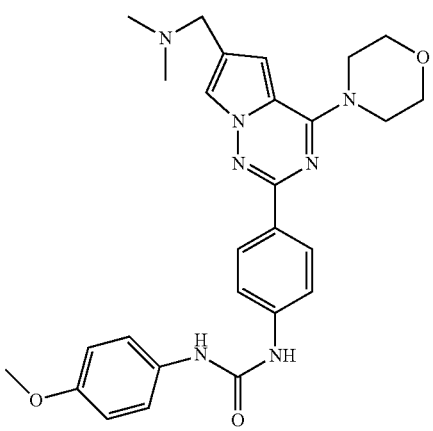
I-11
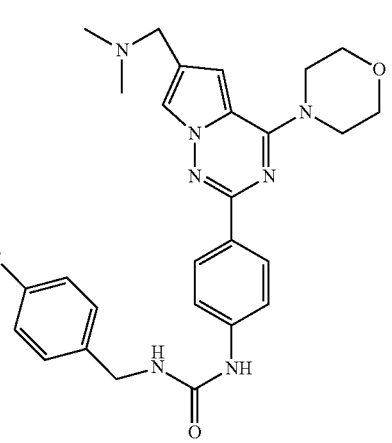
I-12
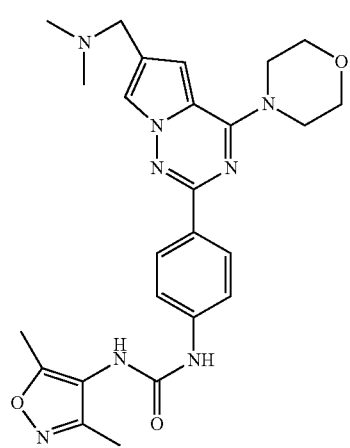

I-13
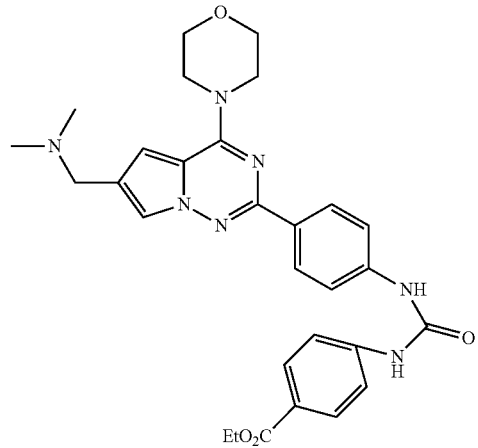
I-14
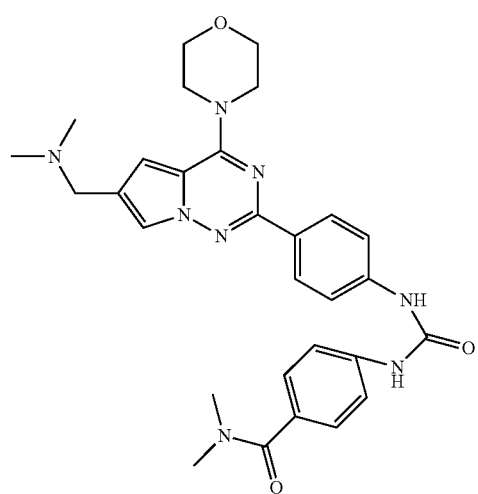
I-15
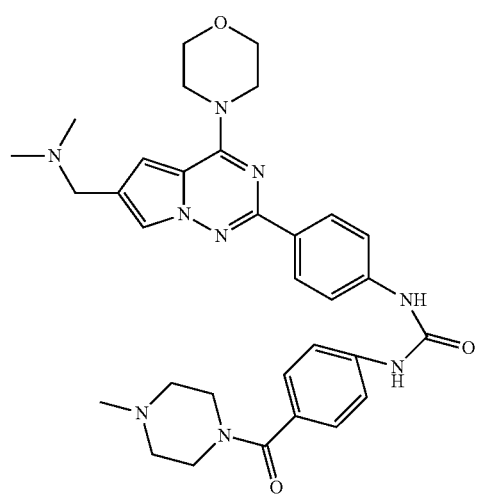
I-16
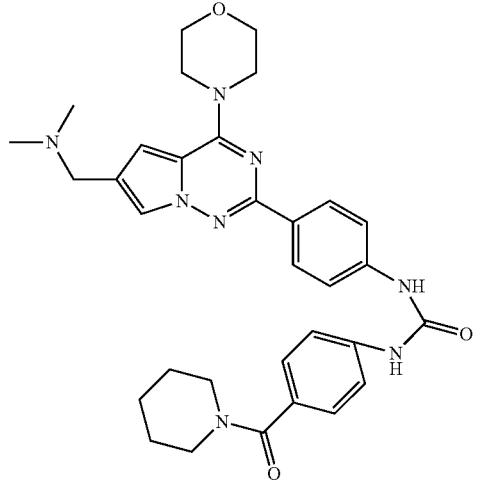
I-17
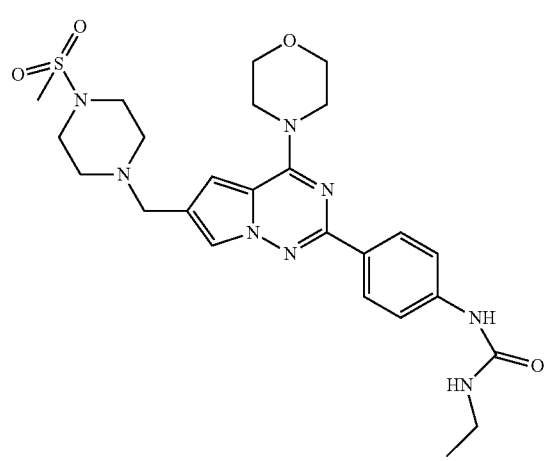
I-18
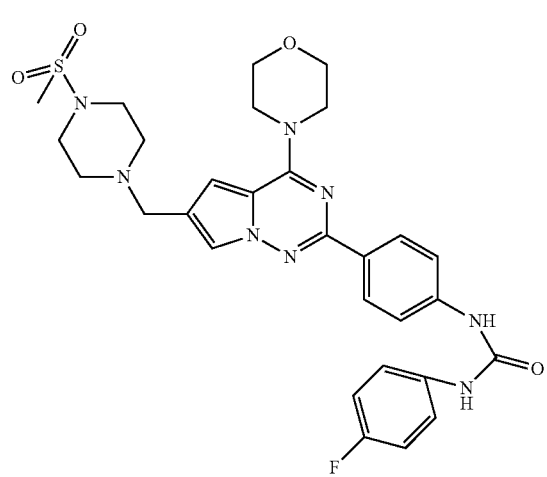

I-19
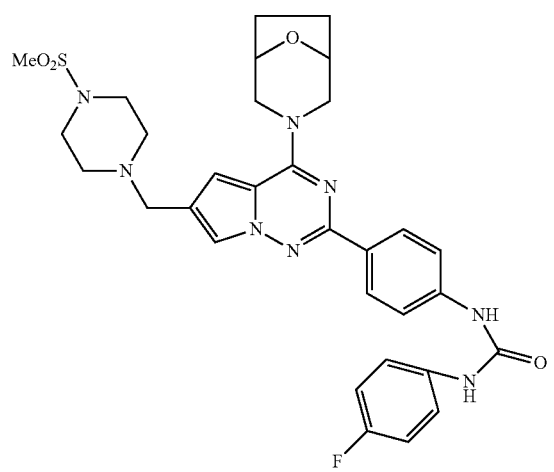
I-20
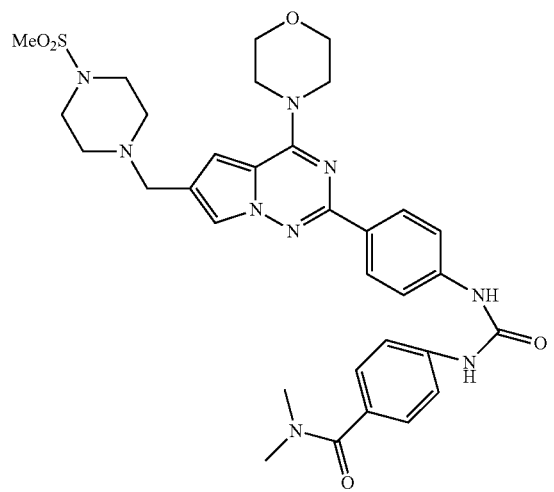
I-21
I-22
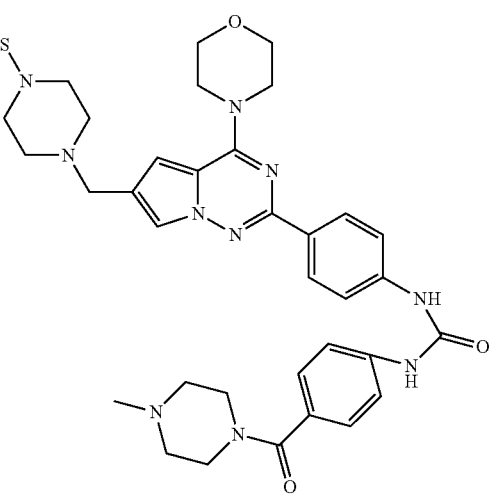
I-23
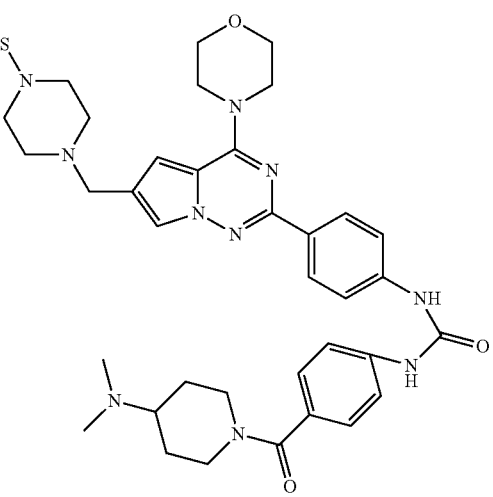
I-24
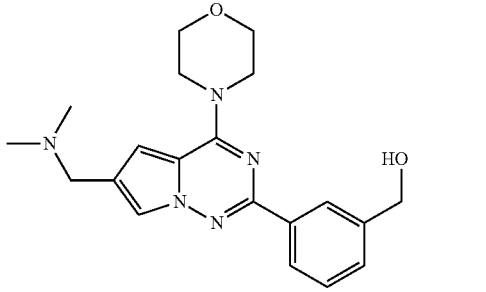
I-25
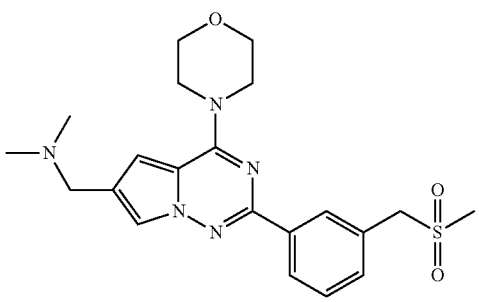

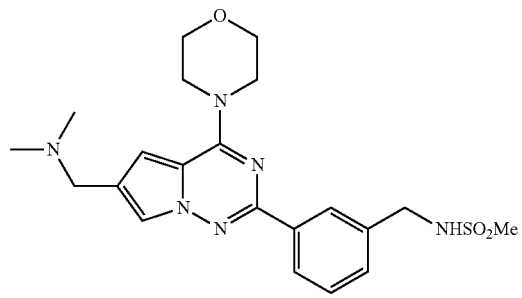
I-26
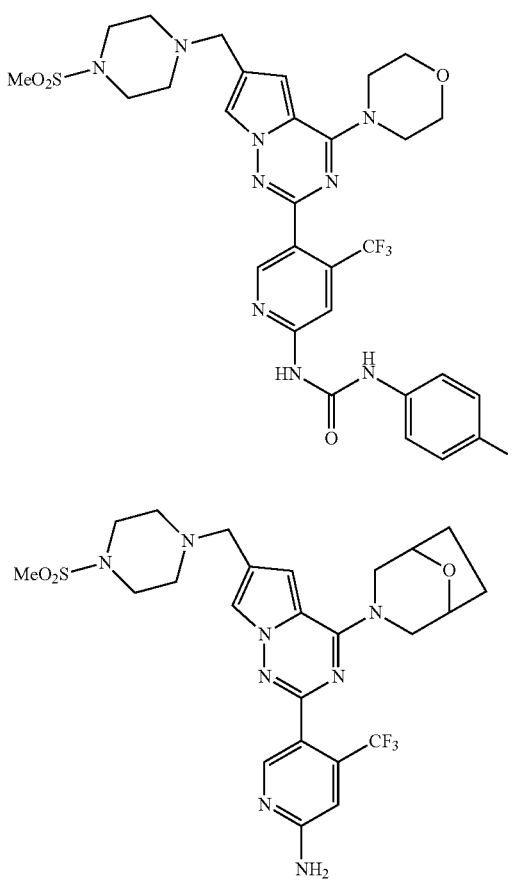
I-27
I-28
I-29
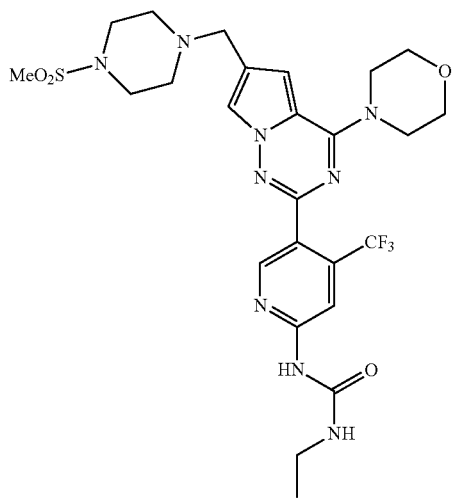
I-30
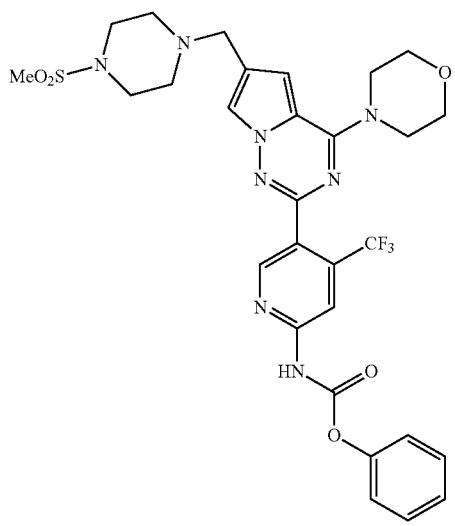
I-31
I-32

-continued

I-33
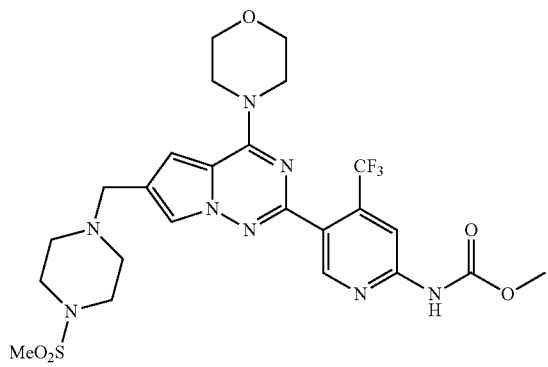

I-34
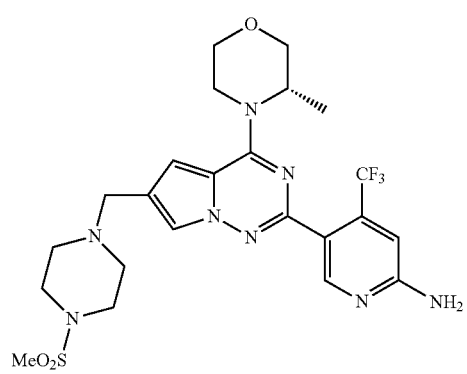

I-35
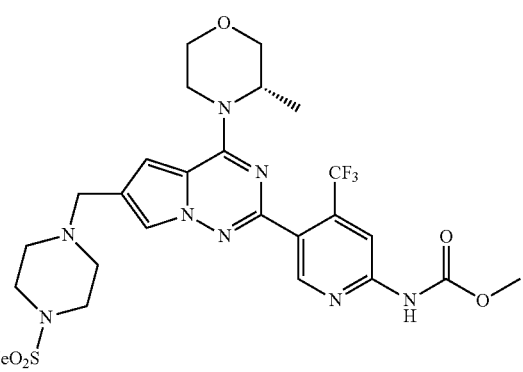

I-36
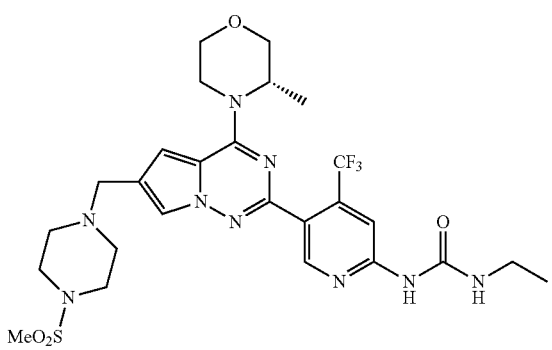

-continued
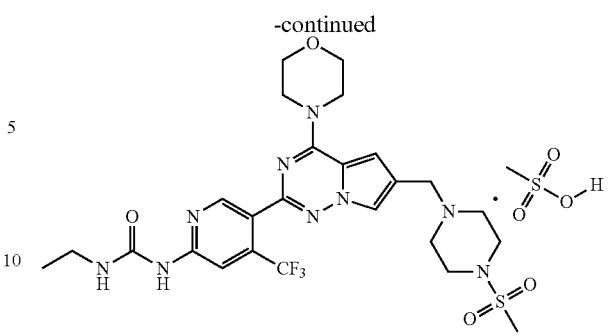

7. The method of claim 1, wherein the pharmaceutical composition has a dose of the compound ranging from 1 to 1000 mg.

8. The method of claim 7, wherein the dose of the compound in the pharmaceutical composition ranges from 10 to 500 mg.

9. The method of claim 1, wherein the pharmaceutical composition is in a form of capsule, tablet, pill, powder, granule, emulsion, solution, suspension, syrup or tincture.

10. The method of claim 1, wherein the pharmaceutically acceptable carrier is cellulose, gelatin, talc, solid lubricant, calcium sulfate, vegetable oil, polyol, emulsifier, wetting agent, coloring agent, flavoring agent, stabilizer, antioxidant, preservative, pyrogen-free water, suspending agent, sweetener, perfume, or a combinations thereof.

11. The method of claim 1, wherein the subject is administered with 1-1000 mg of the compound daily.

12. The method of claim 11, wherein the subject is administered with 30-500 mg of the compound daily.

13. A pharmaceutical composition, comprising a pyrrolo[2,1-f][1,2,4]triazine compound of formula I, a pharmaceutically acceptable salt, or hydrate thereof,

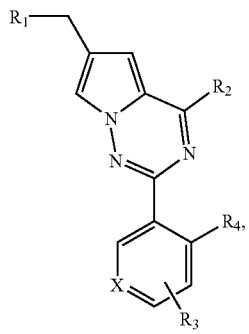

and a pharmaceutically acceptable carrier,
wherein in formula I,
X=CH or N;
$R_1$ is —$NR_5R_6$;
$R_2$ is

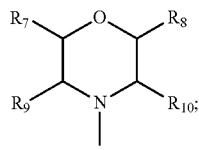

$R_3$ is —$NH_2$, —NHC(O)$NHR_{11}$, —NHC(O)$OR_{11}$, —NHC(O)$R_{11}$, —$CH_2OH$, —$CH_2S(O)_2R_{12}$ or —$CH_2NHS(O)_2R_{12}$;
$R_4$ is H or $CF_3$;
$R_5$ and $R_6$ are each independently a C1-C4 alkyl, or combined with the nitrogen atom to which they are attached to form an unsubstituted 5-8 membered saturated heterocycle or a 5-8membered saturated heterocycle substituted by a substituent, the substituent is —$S(O)_2R_{12}$;
$R_7$, $R_8$, $R_9$ and $R_{10}$ are each independently H or a C1-C3 alkyl, alternatively, $R_7$ and $R_8$, or $R_9$ and $R_{10}$, with the carbon atoms to which they are attached as bridge carbon atoms, form bridged bicylco-heterocycle with morpholine ring;
$R_{11}$ is a C1-C4 alkyl, an unsubstituted C3-C6 cycloalkyl or a C3-C6 cycloalkyl substituted by one or more substituents, an unsubstituted benzyl or a benzyl substituted by one or more substituents, an unsubstituted phenyl or a phenyl substituted by one or more substituents, an unsubstituted isoxazolyl or an isoxazolyl substituted by one or more substituents, or an unsubstituted pyridyl or a pyridyl substituted by one or more substituents, and the one or more substituents are selected from halogen, a C1-C3 alkyl, or a C1-C3 alkoxyl, —$CF_3$, —C(O)$OR_{12}$, —C(O)$NR_{12}R_{15}$,

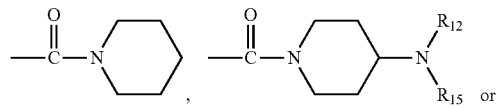

-continued

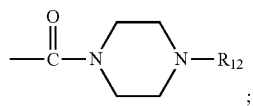

and
$R_{12}$ and $R_{15}$ are each independently a C1-C3 alkyl.

14. The pharmaceutical composition of claim 13, wherein the compound is selected from the group consisting of:

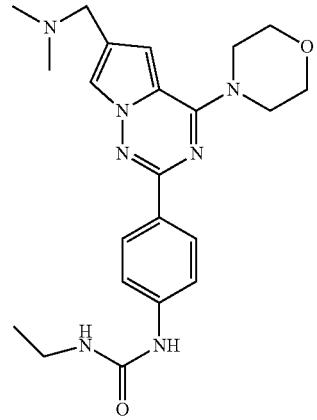

I-1

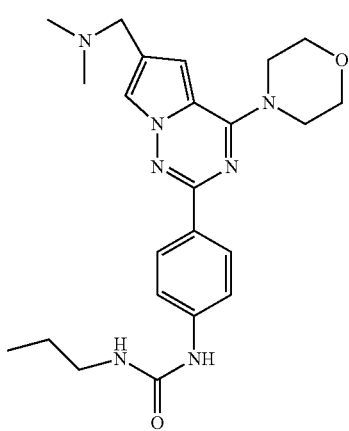

I-2

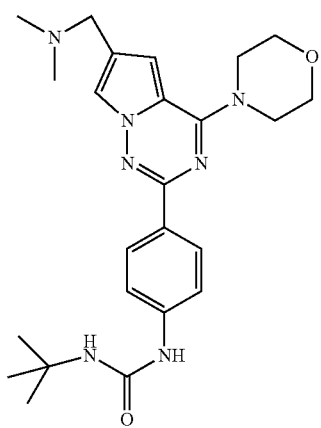

I-3

I-4
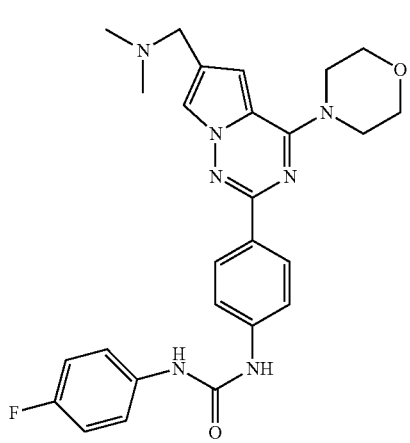
I-5
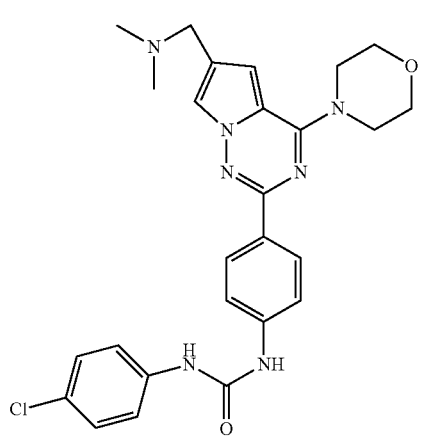
I-6
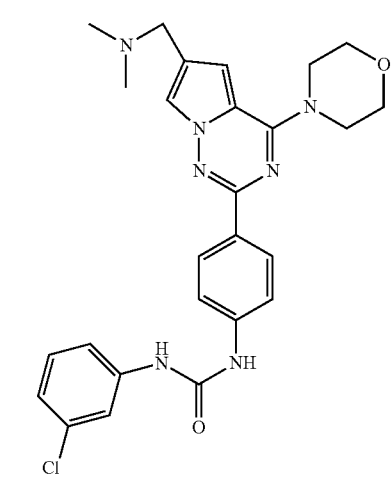
I-7
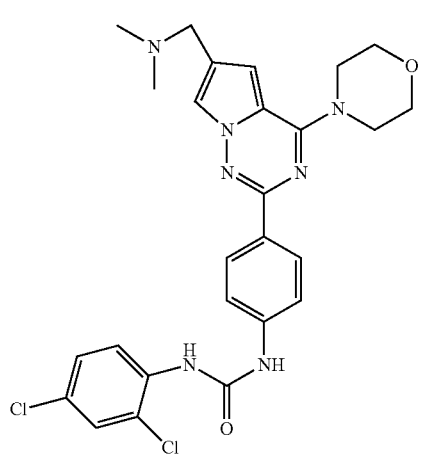
I-8
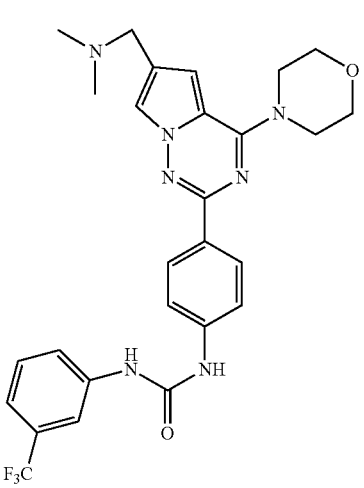
I-9
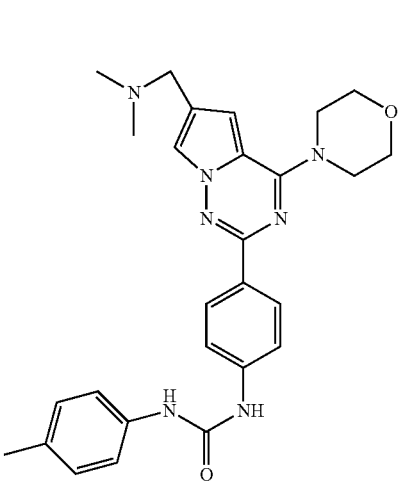

-continued
I-10
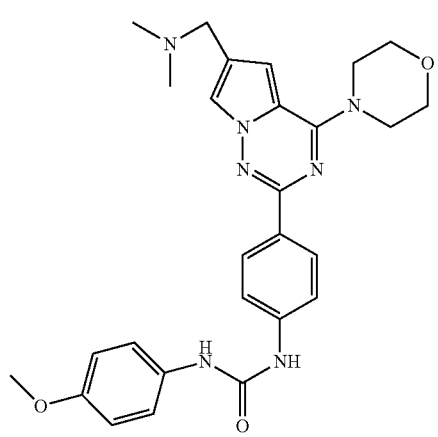
I-11
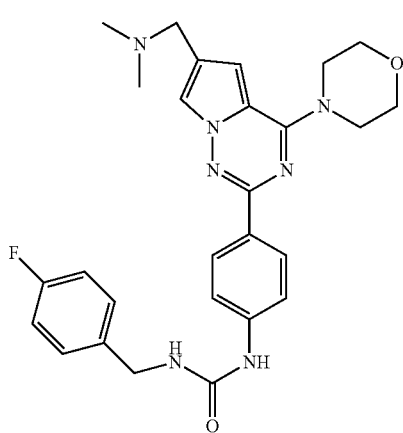
I-12
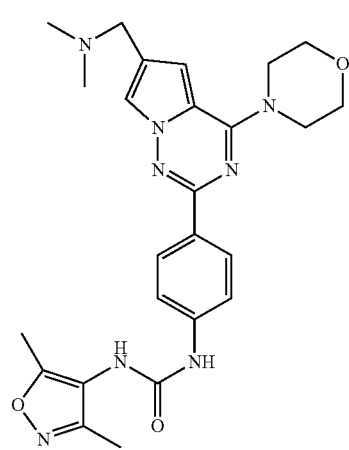
-continued
I-13
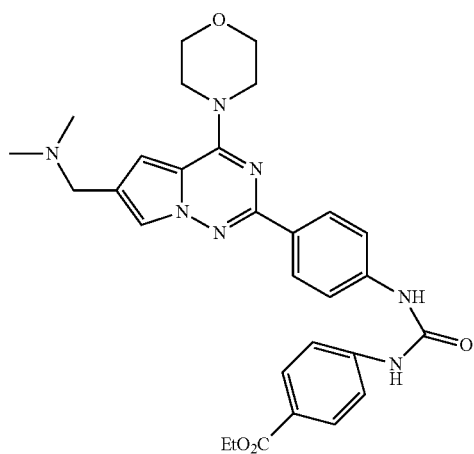
I-14
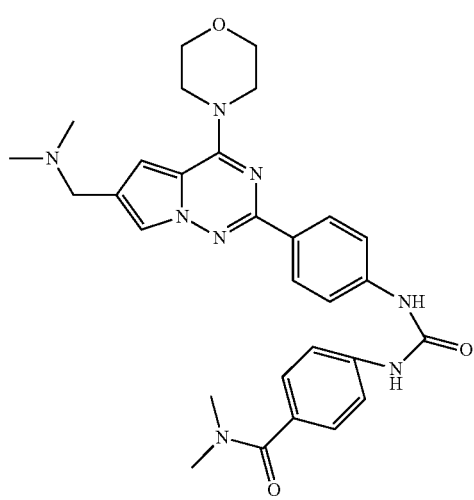
I-15

I-16
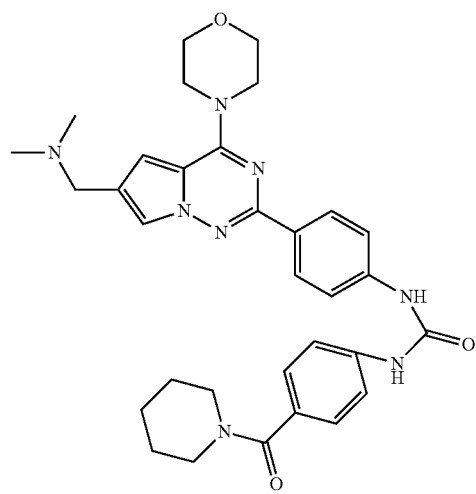
I-17
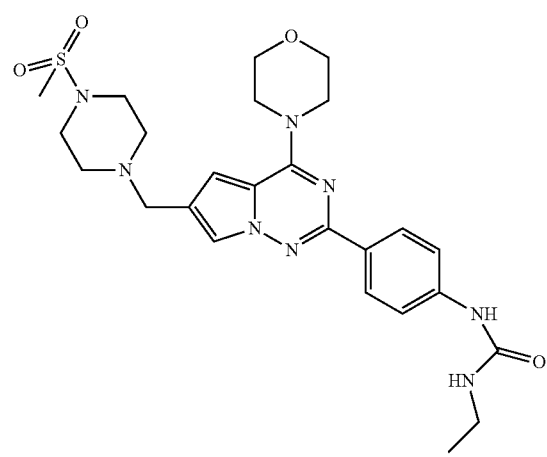
I-18
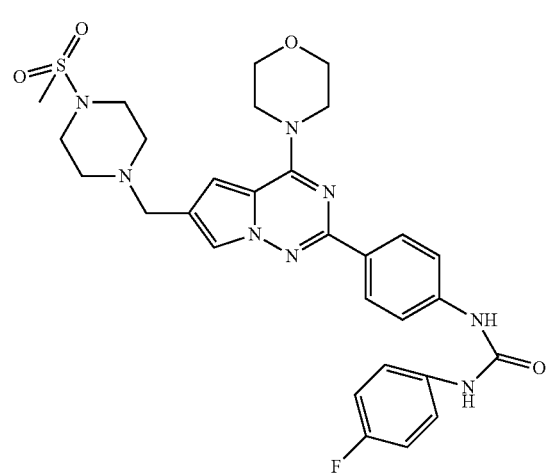
I-19
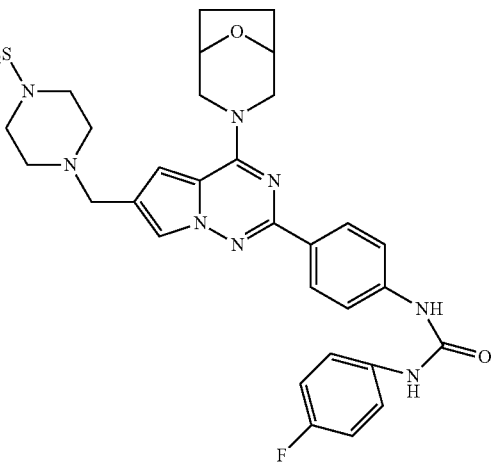
I-20
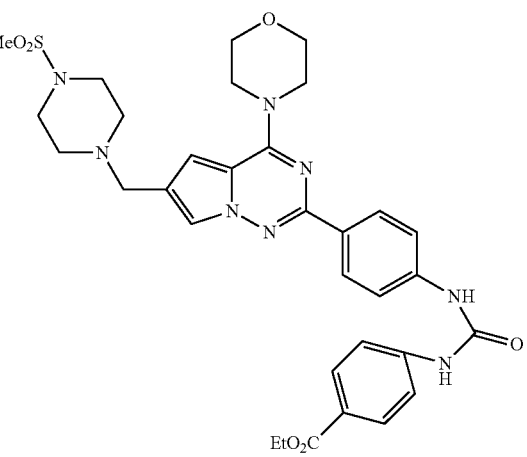
I-21
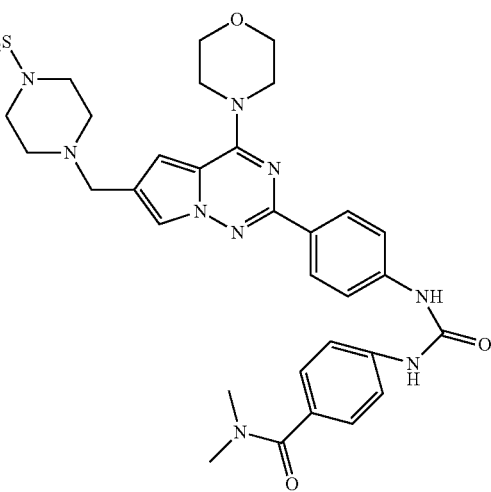

I-22
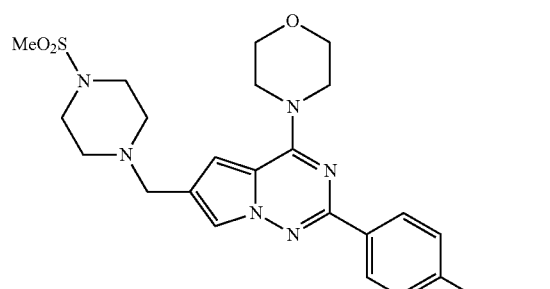
I-23
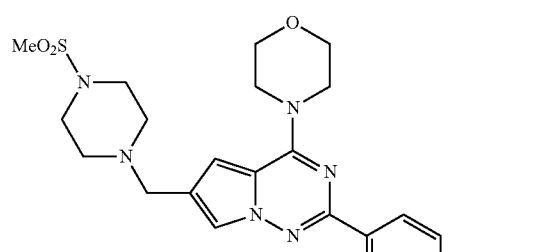
I-24
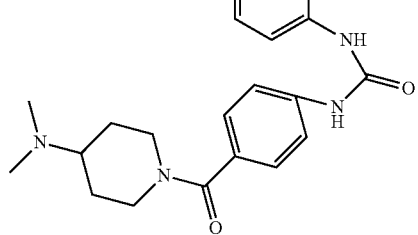
I-25
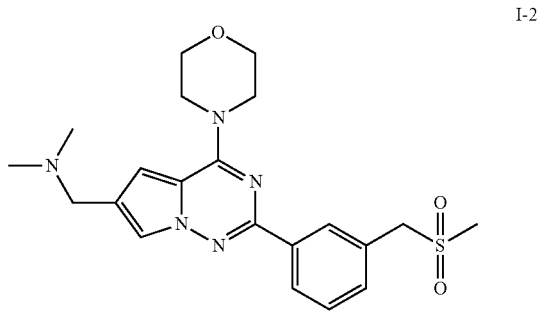
I-26
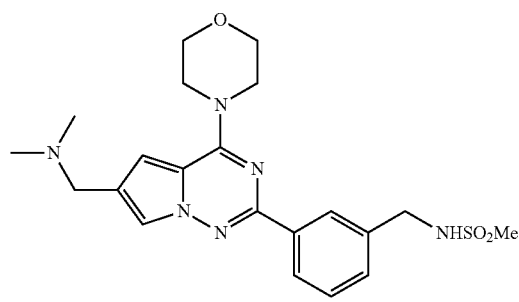
I-27
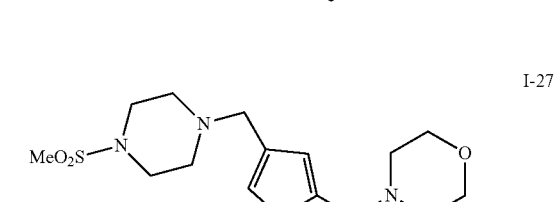
I-28
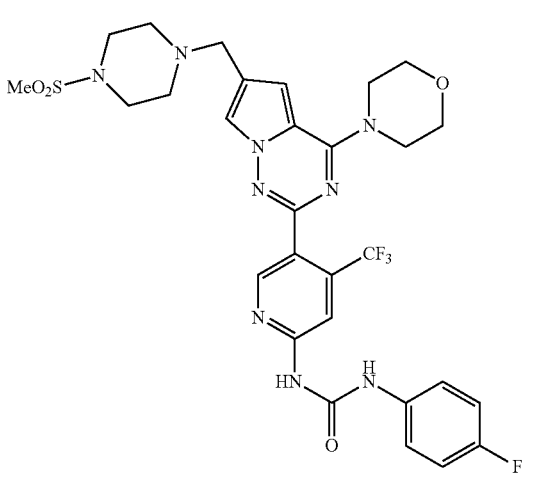
I-29
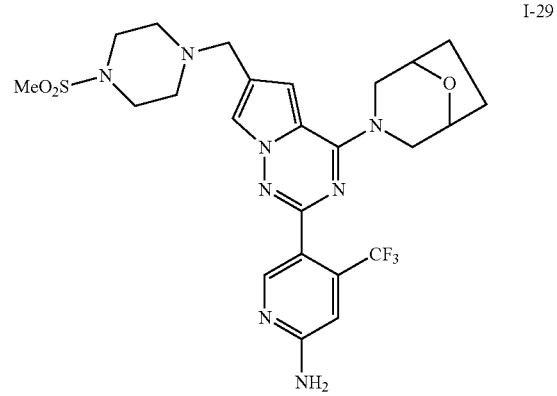

I-30
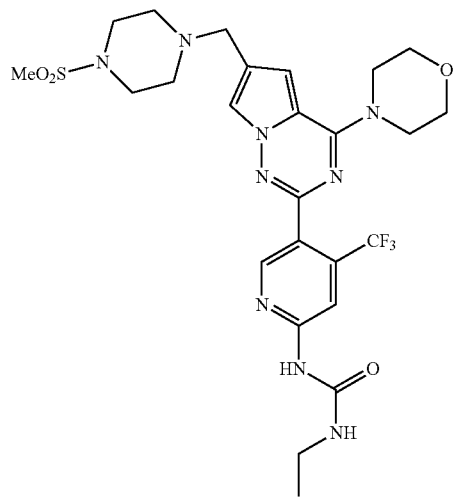
I-31
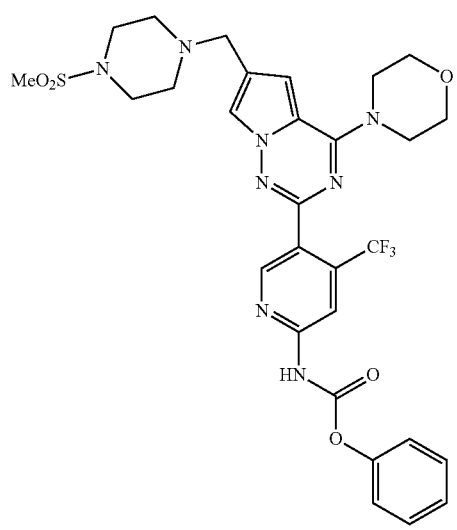
I-32
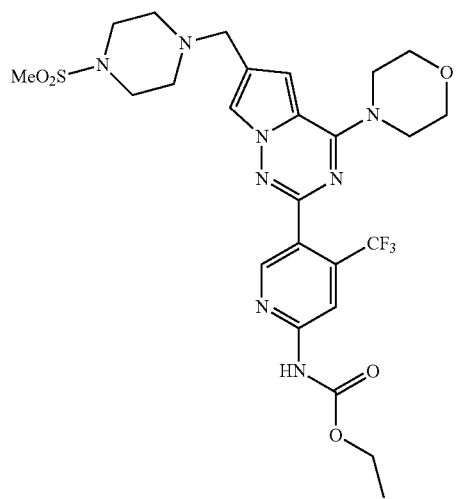
I-33
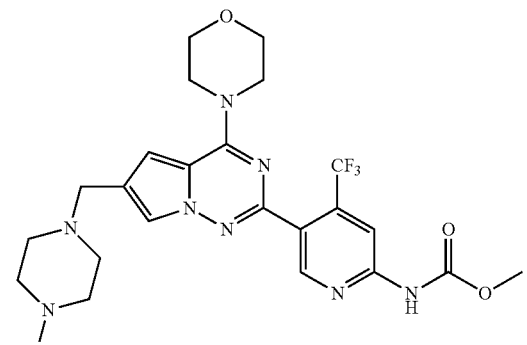
I-34
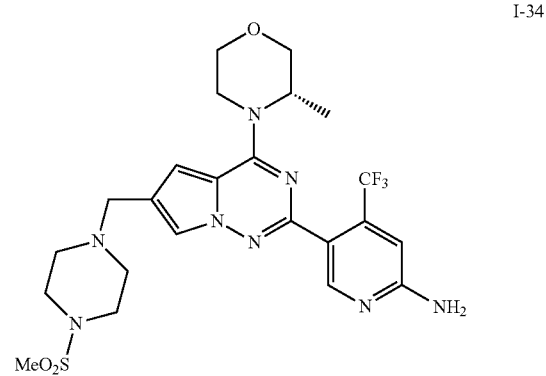
I-35
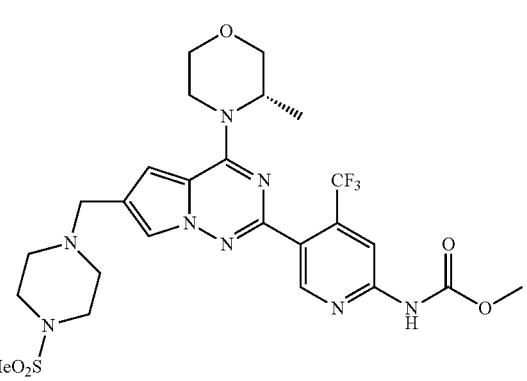
I-36
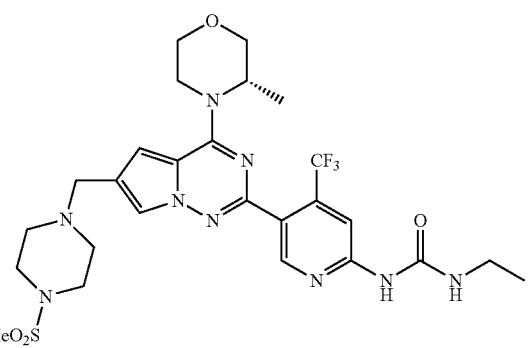

-continued

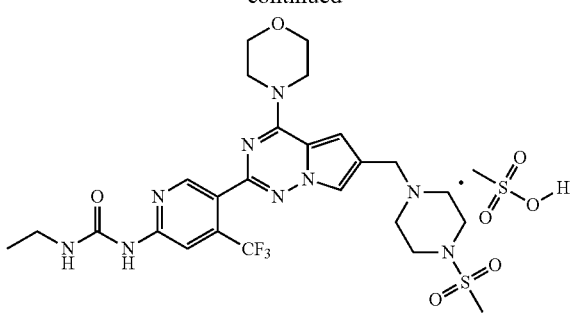

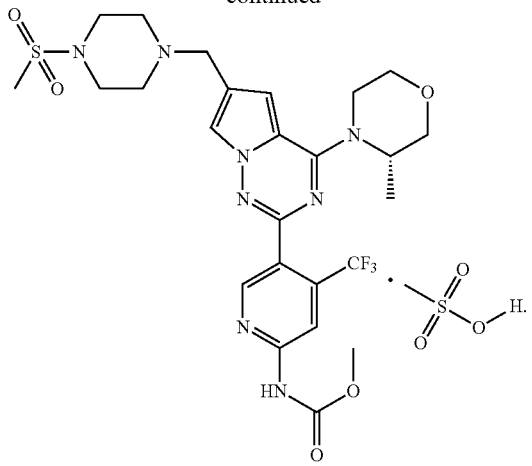

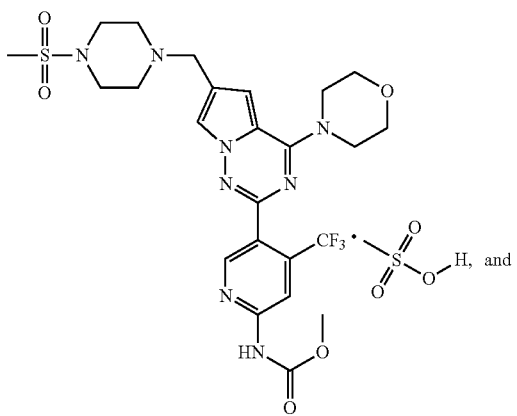

15. The pharmaceutical composition of claim 13, wherein the amount of the compound in the pharmaceutical composition is 1-1000 mg.

16. The pharmaceutical composition of claim 15, wherein the amount of the compound in the pharmaceutical composition is 10-500 mg.

17. The pharmaceutical composition of claim 13, wherein the pharmaceutical composition is in a form of a capsule, tablet, pill, powder, granule, emulsion, solution, suspension, syrup or tincture.

18. The pharmaceutical composition of claim 13, wherein the pharmaceutically acceptable carrier is cellulose, gelatin, talc, solid lubricant, calcium sulfate, vegetable oil, polyol, emulsifier, wetting agent, coloring agent, flavoring agent, stabilizer, antioxidant, preservative, pyrogen-free water, suspending agent, sweetener, flavoring agent, perfume, or a combination thereof.

* * * * *

UNITED STATES PATENT AND TRADEMARK OFFICE
CERTIFICATE OF CORRECTION

PATENT NO. : 9,724,352 B2  
APPLICATION NO. : 15/269069  
DATED : August 8, 2017  
INVENTOR(S) : Chunhao Yang et al.

It is certified that error appears in the above-identified patent and that said Letters Patent is hereby corrected as shown below:

On the Title Page

Item (54) "PYRROLO[2,1-F[1,2,4]TRIAZINE COMPOUNDS, PREPARATION METHODS AND APPLICATIONS THEREOF" should be -- PYRROLO[2,1-F][1,2,4]TRIAZINE COMPOUNDS, PREPARATION METHODS AND APPLICATIONS THEREOF --.

Item (72) "Jian Ding, Shaghai (CN)" should be -- Jian Ding, Shanghai (CN) --.

Signed and Sealed this  
Twenty-third Day of April, 2019

Andrei Iancu  
*Director of the United States Patent and Trademark Office*